(12) United States Patent
Goncalves et al.

(10) Patent No.: US 11,242,359 B2
(45) Date of Patent: Feb. 8, 2022

(54) BIOCOMPATIBLE MODULAR TETRAZINE PLATFORM

(71) Applicants: Centre national de la recherche scientifique, Paris (FR); Université de Bourgogne, Dijon (FR)

(72) Inventors: Victor Goncalves, Dijon (FR); Franck Denat, Quetigny (FR); Claire Bernhard, Fauverney (FR); Coline Canovas, Dijon (FR)

(73) Assignees: CENTRE NATIONAL DE LA RECHERCHE SCIENTIFIQUE, Paris (FR); UNIVERSITÉ DE BOURGOGNE, Dijon (FR)

( * ) Notice: Subject to any disclaimer, the term of this patent is extended or adjusted under 35 U.S.C. 154(b) by 0 days.

(21) Appl. No.: 16/496,387

(22) PCT Filed: Mar. 23, 2018

(86) PCT No.: PCT/EP2018/057520
§ 371 (c)(1),
(2) Date: Sep. 20, 2019

(87) PCT Pub. No.: WO2018/172543
PCT Pub. Date: Sep. 27, 2018

(65) Prior Publication Data
US 2020/0354381 A1 Nov. 12, 2020

(30) Foreign Application Priority Data

Mar. 24, 2017 (FR) ..................................... 17 52451
Oct. 19, 2017 (FR) ..................................... 17 59851

(51) Int. Cl.
*C07D 403/12* (2006.01)
*C07D 403/14* (2006.01)
*C07D 405/14* (2006.01)
*A61K 39/00* (2006.01)
*C07F 5/02* (2006.01)
*C07D 405/12* (2006.01)

(52) U.S. Cl.
CPC ............ *C07F 5/022* (2013.01); *C07D 403/12* (2013.01); *C07D 403/14* (2013.01); *C07D 405/12* (2013.01)

(58) Field of Classification Search
CPC .. C07D 403/12; C07D 403/14; C07D 405/14; A61K 39/00
See application file for complete search history.

(56) References Cited

PUBLICATIONS

Benson, Scott C., et al. "Intramolecular inverse electron demand Diels-Alder reactions of tryptamine with tethered heteroaromatic azadienes." *Tetrahedron* 56.9 (2000): 1165-1180.
Glidewell, Christopher, et al. "The'inverse electron-demand'Diels-Alder reaction in polymer synthesis. Part 4. The preparation and crystal structures of some bis (1, 2, 4, 5-tetrazines)." *Journal of the Chemical Society, Perkin Transactions 2 (Physical Organic Chemistry)* 1997.6 (1997): 1167-1174.
Gong, Yong-Hua, et al. "Synthesis and Physical Chemistry of s-Tetrazines: Which Ones are Fluorescent and Why?." *European Journal of Organic Chemistry* 2009.35 (2009): 6121-6128.
Myers, Thomas W., et al. "Synthesis and Electrochemical Behavior of Electron-Rich s-Tetrazine and Triazolo-tetrazine Nitrate Esters." *Chemistry—A European Journal* 22.30 (2016): 10590-10596.
Quinton, Cassandre, et al. "Original electroactive and fluorescent bichromophores based on non-conjugated tetrazine and triphenylamine derivatives: towards more efficient fluorescent switches." *RSC Advances* 5.61 (2015): 49728-49738.
Rao, Boddu Venkateswara, et al. "A tetrazine templated method for the synthesis of ternary conjugates." *Chemical Communications* 49.92 (2013): 10808-10810.
Guermazi, Refka, et al. "Synthesis and Characterization of New Fluorinated Tetrazines Displaying a High Fluorescence Yield." *Journal of fluorescence* 26.4 (2016): 1349-1356.
Ribagnac, Philippe, et al. "Fluorescent Labeling of a Bisurea-Based Supramolecular Polymer." *The Journal of Physical Chemistry* B 117.6 (2013): 1958-1966.
Institut National de la Propriété Industrielle Search Report issued in French Application FR 1752451 dated Jun. 28, 2017.
International Search Report issued in International Application PCT/EP2018/057520 dated Jun. 19, 2018.

*Primary Examiner* — Bruck Kifle
(74) *Attorney, Agent, or Firm* — Knobbe, Martens, Olson & Bear, LLP

(57) ABSTRACT

A modular tetrazine platform, can be used as diagnostic, theragnostic agent and/or medicinal product. An inverse electron demand Diels-Alder reaction can be used for synthesizing bifunctionalized tetrazines, which can be obtained from monofunctionalised tetrazines.

13 Claims, 5 Drawing Sheets

BIOCOMPATIBLE MODULAR TETRAZINE PLATFORM

CROSS REFERENCE TO RELATED APPLICATIONS

This application is the U.S. National Phase under 35 U.S.C. § 371 of International Application No. PCT/EP2018/057520 filed Mar. 23, 2018, designating the U.S. and published in French as WO 2018/172543 A1 on Sep. 27, 2018, which claims priority to French Patent Application No. 1752451 filed Mar. 24, 2017 and French Patent Application No. 1759851 filed Oct. 19, 2017. Any and all applications for which a foreign or domestic priority claim is identified above and/or in the Application Data Sheet as filed with the present application are hereby incorporated by reference under 37 CFR 1.57.

FIELD OF THE INVENTION

The present invention concerns the field of medical imaging agents, in particular bimodal imaging agents and/or theragnostic agents. The invention particularly sets out to allow specific labelling of biomolecules by imaging probes.

In particular, the invention concerns a trifunctionalised platform of formula (I), such as described below, allowing the conjugation of a bioactive vectorising agent with at least one imaging probe, the third functionality of which can be a second imaging probe (application to bimodal imaging), a cytotoxic agent (application to theragnostics), an affinity agent or solubilising agent.

The invention relates to a method for synthesising these trifunctionalised platforms via inverse electron demand Diels-Alder reaction of a bifunctionalised tetrazine of formula (II) itself able to be obtained from a monofunctionalised tetrazine of formula (IV) (FIG. 1). The invention further concerns mono- and bi-functionalised intermediate tetrazine platforms of formulas (IV) and (II) respectively.

DESCRIPTION OF RELATED ART

The labelling of biomolecules such as proteins e.g. antibodies or peptides, with imaging probes and/or cytotoxic agents is rapidly expanding and is intended to provide powerful tools for chemical biology or human medicine.

Proteins labelled with biotin and fluorophores for example are daily used as probes for cell biology investigation. Peptides or antibodies conjugated with imaging probes are used as diagnostic agents in nuclear medicine units. Similarly, antibodies conjugated with cytotoxic agents (ADC—Antibody Drug Conjugate) show promising clinical results and are the focus of research in the pharmaceutical industry.

It has been shown that strict control of the conjugation site on the biomolecule is critical. The number and the siting of imaging probes or cytotoxic agents attached to a biomolecule can have a strong impact on the biodistribution thereof, on image quality or therapeutic action. In addition, random labelling of biomolecules can give rise to problems of reproducibility, in particular when moving onto large-scale production, and complicates the obtaining of marketing authorisations granted by regulatory bodies.

Recent progress in biochemistry has allowed the synthesising of double labelled biomolecules. Said conjugates, still difficult to obtain, open up new opportunities however. For example, Boerman et al. have developed bimodal imaging probes allowing full body diagnosis of a patient by nuclear imaging, followed by surgeon guidance given by fluorescent imaging of the intra-operative field (Lutje et al., Mol Imaging Biol, 2014, 16, 747-755; Hekman et al., Clin Cancer Res, 2016, 22, 4634-4642). Similarly, Maruani et al. specifically labelled an antibody with a cytotoxic agent and fluorophore, thereby obtaining an ADC having theragnostic potential (Maruani et al., Org Biomol Chem, 2016, 14, 6165-6178). Xu et al. for their part have developed hetero-bivalent agents for imaging and therapy, capable of targeting two receptors on the surface of a specific cell, to improve cell selectivity and drug absorption (Xu et al., PNAS, 2012, 109, 21295-21300).

The double labelling of biomolecules necessitates the development of novel methods which must be:
- easy to implement, i.e. not requiring advanced skills in organic chemistry and/or molecular biology;
- regioselective, to ensure reproducibility thereof, facilitate large-scale production and have the least possible effect on biomolecule activity;
- biocompatible, i.e. able to be produced under mild conditions to preserve the integrity of sensitive constituents such as proteins or fluorophores; and
- modular, to prepare a large variety of double-labelled biomolecules from one same intermediate using one same method.

Current methods for regioselective labelling of proteins are based on the genetic engineering of recombinant proteins, enzymatic modifications, chemical targeting of rare amino acids or the insertion of non-natural amino acids carrying reactive bio-orthogonal functions. The performing of regioselective modifications on two amino acids of a protein is feasible but requires advanced protein engineering technologies which are often difficult to adapt to large-scale production.

To overcome these problems, the present invention proposes a modular method using a trifunctional platform, allowing the regioselective binding of two labels to a biomolecule. For a protein, the amino acid via which it is coupled to the trifunctional platform can be a non-natural amino acid, or a cysteine inserted using well-known methods such as directed mutagenesis.

In addition, the present invention proposes a labelling method having excellent selectivity for the thiol functions of cysteines as opposed to the amine or hydroxy functions of lysines and serines respectively, or other potentially reactive functions contained on bioactive groups such as peptides or antibodies.

Some trifunctional platforms allowing the double labelling of proteins have been described, but the implementation thereof requires a large number of steps some of which are incompatible with fragile molecules such as near-infrared probes or proteins (Maruani et al., Org Biomol Chem, 2016, 14, 6165-6178; Beal et al., Angew Chem Int Ed, 2012, 51, 6320-6326; Maruani et al., Nat Commun, 2015, 6, 6645; Rhashidian et al., J Am Chem Soc, 2013, 135, 16388-16396). In addition, these syntheses are not modular since they generally start with a step to prepare the double-labelled probe: to vary the nature of one of the labels then requires repeating the complete synthesis and optionally adapting some synthesis steps.

There is therefore a need for novel trifunctional platforms allowing modular and biocompatible affording of double-labelled biomolecules i.e. labelled with an imaging probe and a second functionality possibly being a second imaging probe, a cytotoxic agent, an affinity agent or solubilising agent.

The method of the present invention is modular and gives access to the double-labelled biomolecule in only two or three synthesis steps. The biomolecule can be added at the last step, which allows limited degradation thereof at the intermediate steps if it is highly sensitive or if the biomolecule is scarcely stable. Alternatively, it can be added before the second labelling, thereby facilitating optimisation of the double labelling and allowing pre-targeting approaches.

As evidenced in the experimental section below, the synthesis method of the invention can be conducted under extremely mild conditions and in an aqueous medium, compatible with fragile biomolecules such as proteins or antibodies.

SUMMARY

The invention therefore concerns a compound of formula (I)

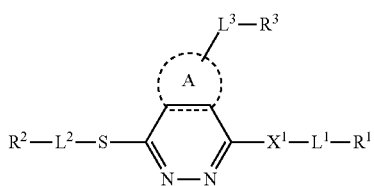

or one of the tautomers thereof, wherein the A ring, $X^1$, $L^1$, $L^2$, $L^3$, $R^1$, $R^2$ and $R^3$ are such as defined below, in particular $R^1$, $R^2$ and $R^3$ are each independently a detectable group, bioactive group, cytotoxic agent, affinity group or solubilising group; provided that at least one of $R^1$ and $R^2$ is a detectable group, and at least one of $R^2$ and $R^3$ is a bioactive group.

In one embodiment, in the compound of formula (I):
the detectable group is selected from among a fluorophore, chromophore, probe for nuclear imaging, MRI probe;
the bioactive group is selected from among an antibody, peptide, peptidomimetic, protein, small molecule such as folic acid, an aptamer, a nanoparticle or liposome;
the cytotoxic agent is selected from among monomethyl auristatin E, maytansinoid DM1, Duocarmycin, Calicheamicin, alpha-amanitin, a group carrying a radiometal, a silica nanoparticle or gold nanoparticle;
the affinity group is selected from among biotin, avidin, streptavidin and a hexa-histidine peptide; and
the solubilising group is selected from among linear or branched poly(ethylene glycol) chains, linear or branched poly(glutamic acid) chains and cholesterol.

The invention further concerns a pharmaceutical composition comprising a formula (I) compound of the invention and a pharmaceutically acceptable vehicle.

The invention also concerns the use of the formula (I) compound of the invention as medicinal product and/or for medical imaging.

The invention also concerns a method for synthesising a formula (I) compound of the invention, comprising the contacting of a bifunctionalised tetrazine of formula (II):

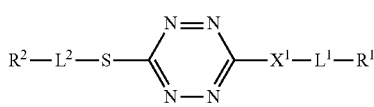

where $X^1$, $L^1$, $L^2$, $R^1$ and $R^2$ are such as defined below, in particular $R^1$ and $R^2$ are each independently a detectable group, bioactive group, cytotoxic agent, affinity group or solubilising group; provided that at least one of $R^1$ and $R^2$ is a detectable group;
with an alkyne or alkene of formula (III):

where the A ring, $L^3$ and $R^3$ are such as defined below, in particular $R^3$ is a detectable group, bioactive group, cytotoxic agent, affinity group or solubilising group; provided that at least one of $R^2$ and $R^3$ is a bioactive group.

In one embodiment, the synthesis method of the invention further comprises a preliminary step to form the bifunctionalised tetrazine of formula (II) by nucleophilic substitution on a monofunctionalised tetrazine of formula (IV):

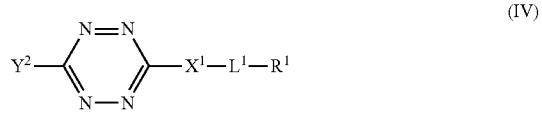

where $Y^2$, $X^1$, $L^1$ and $R^1$ are such as defined below, in particular $R^1$ is a detectable group, bioactive group, cytotoxic agent, affinity group or solubilising group;
in the presence of a thiol of formula (V):

where $L^2$ and $R^2$ are such as defined below, in particular $R^2$ is a detectable group, bioactive group, cytotoxic agent, affinity group or solubilising group; provided that at least one of $R^1$ and $R^2$ is a detectable group.

In one embodiment, the synthesis method of the invention further comprises a preliminary step to form the monofunctionalised tetrazine of formula (IV) by nucleophilic monosubstitution of a tetrazine of formula (VI):

where $Y^1$ and $Y^2$ are such as defined below,
in the presence of a nucleophile of formula (VII):

where $X^1$, $L^1$ and $R^1$ are such as defined below, in particular $R^1$ is a detectable group, bioactive group, cytotoxic agent, affinity group or solubilising group.

The invention further concerns an intermediate compound of formula (II):

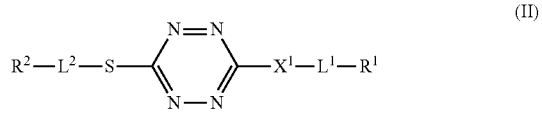

where $X^1$, $L^1$, $L^2$, $R^1$ and $R^2$ are such as defined below, in particular $R^1$ and $R^2$ are each independently a detectable group, bioactive group, cytotoxic agent, affinity group or solubilising group; provided that at least one $R^1$ and $R^2$ is a detectable group.

The invention further concerns an intermediate compound of formula (IV):

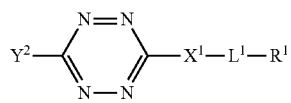

where $Y^2$, $X^1$, $L^1$ and $R^1$ are such as defined below, in particular $R^1$ is a detectable group, bioactive group, cytotoxic agent, affinity group or solubilising group.

The invention further concerns the use of the compound of formula (IV) where $X^1$ is S, to functionalise selectively the thiol functions of the cysteines of a biomolecule selected from among peptides, polypeptides, proteins or antibodies.

The invention also concerns the use of the compound of formula (II) or of a compound of formula (IV), as synthesis intermediate to obtain the compound of formula (I).

DEFINITIONS

In the present invention, the terms below are defined as follows:

The term «alkenyl» refers to any linear or branched hydrocarbon chain carrying at least one double bond, having 2 to 12 carbon atoms and preferably 2 to 6 carbon atoms, e.g. ethenyl, 2-propenyl, 2-butenyl, 3-butenyl, 2-pentenyl and the isomers thereof, 2-hexenyl and the isomers thereof, 2,4-pentadienyl.

The term «alkoxy» refers to an O-alkyl group.

The term «alkynyl» refers to any linear or branched hydrocarbon chain carrying at least one triple bond, having 2 to 12 carbon atoms and preferably 2 to 6 carbon atoms, e.g. ethynyl, 2-propynyl, 2-butynyl, 3-butynyl, 2-pentynyl and the isomers thereof, 2-hexynyl and the isomers thereof.

The term «chelating agent» refers to a polydentate molecule capable of forming coordination bonds with a metal ion to form a metal complex also called a chelate.

The term «alkylaryl» refers to an aryl group substituted by an alkyl group and can be written: -aryl-alkyl.

The term «alkyl» refers to any saturated, linear or branched hydrocarbon chain having 1 to 12 carbon atoms, preferably 1 to 6 carbon atoms, e.g. methyl, ethyl, n-propyl, isopropyl, n-butyl, sec-butyl, isobutyl, tertio-butyl, pentyl and the isomers thereof (e.g. n-pentyl, iso-pentyl), hexyl and the isomers thereof (e.g. n-hexyl, iso-hexyl).

The term «alkylheteroaryl» refers to a heteroaryl group substituted by an alkyl group and can be written: -heteroaryl-alkyl.

The term «antibody» refers to gamma globulin proteins found in the blood or other body fluids of vertebrates, and are used by the immune system to identify and neutralise foreign bodies such as bacteria and viruses. Antibodies are composed of two pairs of polypeptide chains called heavy chains and light chains, which are arranged in Y-shape. The term antibody» such as used herein comprises monoclonal antibodies, polyclonal antibodies, multispecific antibodies (e.g. bi-specific antibodies), antibody fragments, chimeric or hybrid antibodies, single domain antibodies, assembly products of dimer or trimer or minibody antibody fragments.

The term «arylalkyl» refers to an alkyl group substituted by an aryl group and can be written: -alkyl-aryl.

The term «aryl» refers to a polyunsaturated aromatic hydrocarbyl group having a single ring (e.g. phenyl) or several fused aromatic rings (e.g. naphthyl) or covalently bonded (e.g. biphenyl), typically having 5 to 15 carbon atoms, preferably 6 to 10, wherein at least one ring is aromatic. The aromatic ring can optionally include one to two additional rings (either cycloalkyl, heterocyclyl or heteroaryl) fused thereto. Nonlimiting examples of aryl groups comprise the groups phenyl, biphenylyl, biphenylenyl, 5 or 6 tetralinyl, naphthalene-1- or -2-yl, 4, 5, 6 or 7-indenyl, 1- 2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term «chelate» refers to a molecule comprising a metal ion. Chelation (or complexation) entails the formation or the presence of two or bond different coordination bonds between a polydentate molecule (allowing multiple bonds) and a single central metal atom. Polydentate molecules are often organic compounds and are called chelating agents, chelants, ligands or sequestering agents.

The term «strained», in the expression «strained cyclic alkyne or alkene» means that the alkyne or alkene in this ring undergoes stress called ring strain which increases the internal energy thereof making it more reactive than its acyclic equivalent.

The term «cycloalkene» refers to a non-aromatic cyclic or polycyclic alkene group, optionally bridged, optionally fused to one or more aryl groups; preferably a cyclooctyne, bicyclo[6.1.0]nonyne, norbornene, 5,6-dihydrodibenzo[a,e][8]annulene group.

The term «cycloalkyl» refers to a cyclic or polycyclic alkyl group, optionally bridged, optionally fused to one of more aryl groups; preferably a cyclopropyl, cyclopentyl, cyclohexyl, cyclooctyl, norbornyl, bicyclo[6.1.0]nonyl group.

The term «dienophiles» refers to a group of atoms able to react with a diene via cycloaddition reaction [4+2]; preferably an alkyne or alkene.

The term «spacer» refers to a covalent bond or group comprising a series of stable covalent bonds, the group comprising 1 to 40 plurivalent atoms selected from the group formed by C, N, O, S and P; covalently binding two parts of the compounds of the invention. The number of plurivalent atoms in a spacer can be 0, 1, 2, 3, 4, 5, 6, 7, 8, 9, 10, 20, 25 or 30 for example. A spacer can be linear or nonlinear; some spacers have side chains or pendant functional groups (or both). Examples of said side chains are hydrophilicity modifiers, for example solubilising groups e.g. sulfo (—$SO_3H$ or —$SO_3^-$) or carboxylate (—$COO^-$).

In one embodiment, a spacer is composed of any combination of carbon-carbon, carbon-nitrogen, nitrogen-nitrogen, carbon-oxygen and carbon-sulfur single, double, triple or aromatic bonds. For example, spacers can be a combination of groups selected from among alkyl, —C(O)NH—, —NHC(O)—, —C(O)Ar—, —ArC(O)—, —C(O)O—, —NH—, —S—, —O—, —C(O)— and —$S(O)_n$— groups where n is 0, 1 or 2; rings with 5 or 6 monocyclic members and functional side chains (e.g. sulfo, hydroxy or carboxy).

The term «leaving group» refers to a group that departs with the pair of electrons of the sigma bond linking it to the aromatic carbon atom during the substitution reaction with the nucleophile.

The term «halogen» or «halo» refers to fluoro, chloro, bromo, iodo or astato groups, preferably chloro.

The term «heteroaryl» designates aromatic rings having 5 to 15 carbon atoms or cyclic systems containing 1 to 3 rings that are fused together or covalently bound, typically having 5 to 6 carbon atoms and at least one ring thereof being aromatic; wherein one or more carbon atoms in one or more of these rings are replaced by oxygen, nitrogen and/or sulfur atoms; the nitrogen and sulfur atoms optionally being oxidised and the nitrogen atoms optionally being quaternized. Said rings can be condensed to an aryl, cycloalkyl, heteroaryl or heterocyclyl group. Nonlimiting examples of heteroaryl groups comprise the groups: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2, 1-b][1, 3]thiazolyl, thieno[3, 2-b]furanyl, thieno[3, 2-b]thiophenyl, thieno [2,3-d][I, 3]thiazolyl, thieno[2,3-d]imidazolyl, tetrazolo[I, 5-a]pyridinyl, indolyl, indolizinyl, isoindolyl, benzofuranyl, isobenzofuranyl, benzothiophenyl, isobenzothiophenyl, indazolyl, benzimidazolyl, benzoxazolyl, 1,3,1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[I, 2-a] pyridinyl, 6-oxopyridazine-I(6H)-yl, 2-oxopyridine-I(2H)-yl, 6-oxopyridazine-I(6H)-yl, 2-oxopyridin-I(2H)-yl, 1,3-benzodioxolyl, quinolinyl, isoquinolinyl, cinnolinyl, quinazolinyl, quinoxalinyl.

The term «heteroarylalkyl» refers to an alkyl group substituted by a heteroaryl group and can be written: -alkyl-heteroaryl.

The term «heterocycloalkene» refers to a cycloalkene group such as defined above, wherein one or more carbon atoms are replaced by one or more heteroatoms selected from among O, S, N; preferably the heterocycloalkene group is 5,6-dihydrodibenzo[b,f]azocine.

The term «medical imaging» refers to a set of techniques whereby different regions or different organs of the body are imaged using different physical phenomena such as X-ray absorption, fluorescence, nuclear magnetic resonance, ultrasound wave reflection or radioactivity.

The term «lipid» refers to hydrophobic or amphiphilic molecules comprising inter alia fats, waxes, sterols, liposoluble vitamins, mono-, di- and triglycerides, or phospholipids.

The term «liposome» refers to an artificial vesicle formed by concentric lipid bilayers, trapping aqueous compartments between them. A broad variety of amphiphilic lipids can be used to form liposomes, the most frequently used being phospholipids.

The term «peptide» designates a linear polymer of amino acids in which the amino acids are linked together by peptide bonds.

The term «peptidomimetic» designates a compound designed to imitate a biologically active peptide but having structural differences, imparting thereto more advantages for its function as medicinal product.

The term «protein» refers to a functional entity formed of one or more peptides and possibly non-peptide co-factors.

The term «nanoparticle» refers to a particle having a size ranging from 1 to 100 nm; in particular, a nanoparticle can be a liposome, a nanoparticle of iron oxide, a nanoparticle of silica (e.g. AGuIX nanoparticle) or a nanoparticle of gold.

The term «tetrazine» refers to the reactive function composed of an aromatic nucleus with six atoms containing four atoms of nitrogen and two atoms of carbon. This heterocycle has three different isomers depending on the relative position of the carbon and nitrogen atoms: 1,2,3,4-tetrazine, 1,2,3,5-tetrazine and 1,2,4,5-tetrazine. In the present invention, tetrazine refers to 1,2,4,5-tetrazine.

The term «vehicle» refers to a substance which carries the product of interest in a composition, in particular it may be a substance which allows the dissolving thereof. For example, the vehicle can be water. The term «pharmaceutically acceptable vehicle» refers to a vehicle or inert carrier used as solvent or diluent in which the active agent is formulated and/or administered, and which does not produce an adverse reaction, allergic or otherwise, when administered to an animal, preferably a human being. This encompasses all solvents, dispersion media, coatings, antibacterial and antifungal agents, isotonic agents, absorption retardants and other similar ingredients. For administration to man, preparations must meet standards of sterility, general safety and purity, such as required by regulatory offices such as the FFDA or EMA.

DETAILED DESCRIPTION

Trifunctionalised Platform (I)

The invention particularly concerns a trifunctionalised platform, preferably of formula (I) such as described above, functionalised by at least one biomolecule (or more generally a bioactive group) and at least one imaging probe, the third functionality of which is possibly another imaging probe (application to bimodal imaging), a cytotoxic agent (application to theragnostics), an affinity group or solubilising group.

The invention therefore concerns a trifunctionalised platform of formula (I):

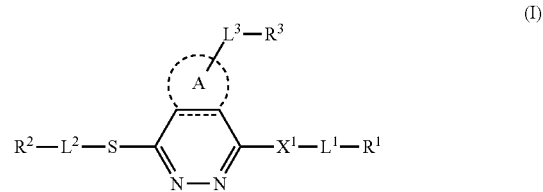

or one of the tautomers thereof;
where:
===== represents a double bond or single bond, preferably a double bond;
ring A represents a cycloalkyl, cycloalkene or heterocycloalkene group, optionally substituted by one or more groups selected from among alkyl, aryl, halo, hydroxy and heteroaryl; preferably A represents a group from among bicyclo[6.1.0]nonane, cyclooctane, bicyclo[6.1.0]nonene, cyclooctene, difluorocyclooctene, hydroxycyclooctene, methylcyclopropane, norbornene, 5,6-dihydrodibenzo[a,e][8]annulene, 5,6-dihydrodibenzo[b,f]azocine;
$X^1$ is S, NH or O; preferably $X^1$ is S or NH;
$L^1$, $L^2$ and $L^3$ are each independently a single bond or spacer selected from among alkyl, alkoxy, aryl, arylalkyl, alkylaryl, heteroaryl, heteroarylalkyl, alkylheteroaryl, alkenyl and alkynyl groups, wherein the alkyl groups are optionally interrupted and/or terminated by one or more groups selected from among —O—, —NH—, —S—, —C(O)—, —C(O)NH— and —NHC(O)—; preferably $L^1$, $L^2$ and $L^3$ are each independently an alkyl or alkylaryl spacer, optionally interrupted and/or terminated by one or more groups selected from among —O—, —C(O)—, —NH— and —NHC(O)—; more preferably $L^1$, $L^2$ and $L^3$ are each independently a spacer selected from among —CH$_2$CH$_2$NH—, —NHCH$_2$CH$_2$NH—, —CH$_2$OCONHCH$_2$CH$_2$NHCOCH$_2$CH$_2$—, —CH$_2$OCO—, —COCH$_2$CH$_2$NH—, —CH$_2$CH$_2$NHCOCH$_2$CH$_2$— and —CH$_2$CH$_2$NHCO-p-Ph-;

$R^1$, $R^2$ and $R^3$ are each independently a detectable group, bioactive group, cytotoxic agent, affinity group or solubilising group;

provided that at least one of $R^1$ and $R^2$ is a detectable group, and at least one of $R^2$ and $R^3$ is a bioactive group.

Ring A is obtained by inverse electron demand Diels-Alder reaction between a 1,2,4,5-tetrazine of formula (II) and a dienophile molecule of formula (III) such as described below. The inverse electron demand Diels-Alder reaction between a 1,2,4,5-tetrazine and a dienophile (e.g. an alkene or alkyne) produces an unstable cycloadduct which spontaneously undergoes a retro-Diels Alder reaction to form one molecule of dinitrogen and a dihydropyridazine (after reaction with an alkene) or a pyridazine (after reaction with an alkyne). The dihydropyridazine product can optionally undergo an additional oxidation reaction to form the corresponding pyridazine. The dienophiles useful for this invention include, but are not limited thereto, carbon dienophiles such as alkenes or alkynes, preferably a «strained» cyclic alkene or alkyne. In one preferred embodiment, the dienophile is preferably a bicyclononyne or trans-cyclooctene.

The term «detectable group» refers to a chemical group that can be detected, directly or after modification, using imaging techniques known to persons skilled in the art.

In one embodiment, the detectable group is selected from among fluorophores; chromophores; probes for nuclear imaging; MRI probes.

In one embodiment, the imaging techniques allowing the detection of said detectable group comprise: nuclear imaging including positron emission tomography (PET), single photon emission computed tomography (SPECT) and Cerenkov Luminescence imaging (CLI); magnetic resonance imaging (MRI); optical imaging; fluorescence imaging.

In one embodiment, the detectable group can be detected directly, such as present on the compound of the invention, with an imaging technique.

In another embodiment, the detectable group must be previously modified before it can be detected by an imaging technique. This is the case when the detectable group is in the form of a chelating agent. In this case, a prior complexing step with a metal ion is needed for subsequent detection by an imaging technique, preferably by nuclear imaging or magnetic resonance imaging.

The term «fluorophore» refers to a chemical substance capable of emitting fluorescent light after excitation. Preferably, the fluorophores are molecules comprising several conjugated aromatic nuclei or planar or cyclic molecules having one or more π bonds.

In one embodiment, the fluorophores are selected from among cyanine derivatives (Cyanine3, Cyanine5, Cyanine5.5, Cyanine7, Sulfonated Cyanines); Alexa fluor 647; a coumarin (hydroxycoumarin, aminocoumarin, methoxy coumarin); a rhodamine (X-rhodamine, rhodamine B); a fluorescein or BODIPY. Preferably the fluorophore is selected from among Cyanine5, a sulfonated Cyanine, a rhodamine or BODIPY.

The term «chromophore» refers to a group of atoms comprising one or more double bonds, and forming with the remainder of the molecule a sequence of conjugated double bonds, thereby imparting its colour to the molecule in which it is contained. A chromophore is detectable by absorbance measurement.

In one embodiment, the chromophores are selected from among phenolphthalein, gentian violet or Congo Red.

By «probes for nuclear imaging», it is meant probes able to be detected by nuclear imaging techniques.

In one embodiment, the probes for nuclear imaging are selected from among radioisotopes, organic groups labelled with a radioisotope, chelating agents, radioisotope chelates.

One example of radioisotope for nuclear imaging is fluorine-18.

In one embodiment, the chelating agents, whether linear or cyclic, are for example DOTA, NOTA, deferoxamine, and derivatives thereof. Preferred derivatives of DOTA and NOTA are DOTAGA and (R)-NODAGA respectively for example.

The chelates of corresponding radioisotopes can be obtained by complexing these chelating agents with metal ions such as: $^{64}$Cu, $^{68}$Ga, $^{111}$In, $^{89}$Zr, $^{177}$Lu.

Therefore, the «detectable group» comprises both directly detectable radioisotope chelates and the chelating agents that have not yet complexed the radioisotope. In this latter case, complexing can be performed just before use of the platform of the invention for an imaging application. In particular, this makes it possible to store the platform ready to be chelated and to add the radioisotope, which may have a very short half-life, only at the last minute before use.

The term «MRI probe» (Magnetic Resonance Imaging) refers to paramagnetic contrast agents (e.g. comprising gadolinium) or superparamagnetic contrast agents (e.g. comprising nanoparticles of iron oxide) intended artificially to increase contrast allowing visualisation of anatomic structures (e.g. an organ) or pathological structures (e.g. a tumour) that naturally have little or no contrast, and which would therefore be difficult to distinguish from neighbouring tissues.

In one embodiment, the invention concerns the use of compounds I-1, I-2 and/or I-3 such as previously described, to target tumours such as breast tumours. In one embodiment, the compounds I-1, and/or I-3 such as previously described specifically target a tumour, preferably a breast tumour.

In one embodiment, the MRI probes are selected from among chelating agents, chelates, nanoparticles.

In one embodiment, the chelating agents are DOTA and DTPA for example.

In one embodiment, the corresponding chelates can be obtained by complexing these chelating agents with metal ions e.g. Gd or Mn; or with iron oxide.

Preferably, the nanoparticles are iron oxide nanoparticles or silica nanoparticles of AGuIX type.

The terms «bioactive group» or «biomolecule» refer to any natural biological molecule or any synthetically derived molecule which imitates or is an analogue of a natural biological molecule.

Biomolecules comprise nucleotides, polynucleotides (e.g. RNA, DNA), amino acids, peptides, polypeptides, proteins, antibodies, polysaccharides, lipids, glycans and small molecules (e.g. vitamins, primary and secondary metabolites, hormones, neurotransmitters). Amino acids may comprise fragments other than those found in the 20 natural amino acids. Amino acids may also comprise non-proteinogenic functional groups (e.g. $CF_3$, $N_3$, F, $NO_2$). Similarly, polypeptides and proteins may contain said amino acids. «Polysaccharides» comprise mono-, di- and oligosaccharides having O- and N-glycosyl bonds. Polysaccharides may comprise functional groups which are not usually found in a cell environment (e.g. cyclopropene, halogens and nitriles). Lipids comprise amphipathic, phospho- and glycolic lipids and sterols such as cholesterol. An «amphipathic lipid» designates a lipid having hydrophilic and hydrophobic characteristics. A «phospholipid» designates a lipid bonded to a phosphate group and carrying a charge. Examples of phospholipids comprise phosphatidic acid, phosphatidylethanolamine, phosphatidylcholine, phosphatidylserine and phosphatidylinositol. A «glycolipid» designates a lipid bonded to a poly- or oligosaccharide. Examples of glycolipids comprise galactolipids, sulfolipids, glycosphingolipids and glycosylphosphatidylinositol. Lipids may comprise substituents rarely found in a cell environment (e.g. cyclopropene, halogens and nitriles). A «small molecule» such as used herein designates any small molecule naturally produced in a biological environment and possibly containing non-natural fragments or bonds which are not typically found in a cell but tolerated during treatment of a cell (e.g. cyclopropene, halogens, nitriles).

In one embodiment, the bioactive group is preferably selected from among an antibody, peptide, peptidomimetic, protein, small molecule such as folic acid, an aptamer, preferably a nucleic acid aptamer, a nanoparticle or liposome; more preferably the bioactive group is selected from among antibodies (e.g. Trastuzumab) or peptides. In one embodiment, the bioactive group is Bovine Serum Albumin (BSA).

Examples of bioactive groups and their biological targets are given in the table below:

| Type | Specific example | Biological target |
|---|---|---|
| antibody (whole) | Trastuzumab, pertuzumab | HER2 |
| | Brentuximab | CD30 |
| modified protein (antibody fragment, affibody, DARPin, etc.) | T84.66 diabody | carcinoembryonic antigen (CEA) |
| | Affibody $Z_{HER2:342}$ | HER2 |
| protein | VEGF | VEGFR |
| Peptide | Bombesin(7-14) | gastrin-releasing peptide receptors |
| | Octreotate | somatostatin receptors |
| Peptidomimetic | c(RGDyK) | alpha$_v$beta$_3$ integrin |
| small molecule | folic acid | folate receptor |
| nucleic acid aptamer | NX21909 | Human neutrophil elastase |
| Nanoparticles, liposomes | iron oxide nanoparticles, AGuIX nanoparticles | tumours and inflammatory tissue via increased permeability and retention effect |

The term «cytotoxic agent» refers to a substance capable of killing cells, including cancer cells. These agents can prevent cells from dividing, and with respect to cancer cells can induce a reduction in tumour size.

In one embodiment, the cytotoxic agent is selected from among monomethyl auristatin E, maytansinoid DM1, Duocarmycin, Calicheamicin, alpha-amanitin or a group carrying a radiometal (e.g. a $^{131}$I-labelled group, a radiometal chelate such as $^{90}$Y, $^{223}$Ra, $^{225}$Ac, $^{177}$Lu).

In another embodiment, the cytotoxic agent is a nanoparticle, preferably a silica nanoparticle or gold nanoparticle. In this case, the nanoparticle can act as radiosensitizer.

Examples of cytotoxic agents and their biological targets and/or mechanism of action are given in the table below:

| Cytotoxic agent | Target/Mechanism of action |
|---|---|
| monomethyl auristatin E | Tubulin |
| maytansinoid DM1 | Tubulin |
| Duocarmycin | DNA alkylating agent |
| Calicheamicin | DNA (rupture) |
| alpha-amanitin | RNA polymerase II inhibitor |
| radio-emitter (e.g. $^{131}$I-labelled group, radiometal chelate such as $^{90}$Y, $^{223}$Ra, $^{225}$Ac, $^{177}$Lu) | DNA |

The term «affinity group» refers to a chemical group, sometimes called a label, which can be selectively and non-covalently bonded to another partner chemical group, using techniques known to skilled persons.

In one particular embodiment, the affinity group is selected from among biotin (partner: streptavidin or avidin), avidin (partner: biotin), streptavidin (partner: biotin) or a hexa-histidine peptide (partner: nickel).

The term «solubilising group» refers to a synthetic or natural chemical group allowing modification of the physicochemical properties of the trifunctional platform, in particular the hydrophilic/lipophilic nature thereof, its molecular volume or overall electric charge in a buffered medium. The type of solubilising group can have an impact on the biodistribution of the platform (I), its pharmacokinetics or on animal bioavailability.

In one embodiment, the solubilising group is selected from among linear or branched poly(ethylene glycol) chains, linear or branched poly(glutamic acid) chains, or cholesterol.

In one embodiment, $R^1$ is a detectable group, $R^2$ is a bioactive group and $R^3$ is a detectable group, bioactive group, cytotoxic agent, affinity group or solubilising group, preferably $R^3$ is a detectable group.

In one embodiment, $R^2$ is a detectable group, $R^3$ is a bioactive group and $R^1$ is a detectable group, bioactive group, cytotoxic agent, affinity group or solubilising group, preferably $R^1$ is a detectable group.

In one embodiment, $R^1$ is a detectable group, $R^3$ is a bioactive group and $R^2$ is a detectable group, bioactive group, cytotoxic agent, affinity group or solubilising group, preferably $R^2$ is a detectable group.

In one embodiment, $X^1$ is S, NH or O, preferably $X^1$ is S or NH. In one particular embodiment, $X^1$ is S. In another particular embodiment, $X^1$ is NH.

In one embodiment, $L^1$ is an alkyl or alkylaryl spacer, optionally interrupted and/or terminated by one or more groups selected from among —O—, —C(O)—, —NH— and —NHC(O)—; preferably $L^1$ is a spacer selected from among —CH$_2$CH$_2$NH—, —NHCH$_2$CH$_2$NH—, —CH$_2$OCONHCH$_2$CH$_2$NHCO—CH$_2$CH$_2$—, —CH$_2$OCO—, —COCH$_2$CH$_2$NH—, —CH$_2$CH$_2$NHCOCH$_2$CH$_2$— and —CH$_2$CH$_2$NHCO-p-Ph-.

In one embodiment, $L^2$ is an alkyl or alkylaryl spacer, optionally interrupted and/or terminated by one or more groups selected from among —O—, —C(O)—, —NH— and —NHC(O)—; preferably $L^2$ is a spacer selected from among —CH$_2$CH$_2$NH—, —NHCH$_2$CH$_2$NH—, —CH$_2$OCONHCH$_2$CH$_2$NHCOCH$_2$CH$_2$—, —CH$_2$OCO—, —COCH$_2$CH$_2$NH—, —CH$_2$CH$_2$NHCOCH$_2$CH$_2$— and —CH$_2$CH$_2$NHCO-p-Ph-; more preferably, $L^2$ is —CH$_2$CH$_2$NH—.

In one embodiment, $L^3$ is an alkyl or alkylaryl spacer optionally interrupted and/or terminated by one or more groups selected from among —O—, —C(O)—, —NH— and —NHC(O)—; preferably $L^3$ is a spacer selected from among —CH$_2$CH$_2$NH—, —NHCH$_2$CH$_2$NH—, —CH$_2$OCONHCH$_2$CH$_2$NHCO—CH$_2$CH$_2$—, —CH$_2$OCO—, —COCH$_2$CH$_2$NH—, —CH$_2$CH$_2$NHCOCH$_2$CH$_2$— and —CH$_2$CH$_2$NHCO-p-Ph-; more preferably $L^3$ is —NHCH$_2$CH$_2$NHCOCH$_2$—.

In one embodiment, the trifunctionalised platforms of formulas (I) have the formula (Ia):

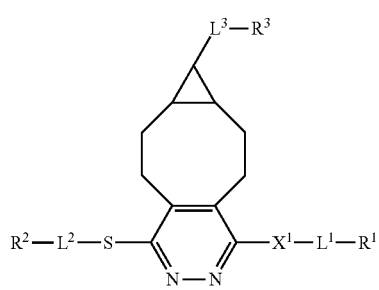

(Ia)

or one of the tautomers thereof, where $X^1$, $L^1$, $L^2$, $L^3$, $R^1$, $R^2$ and $R^3$ are such as defined in formula (I) above.

In one embodiment, the trifunctionalised platforms of formulas (I) have the formula (Ib):

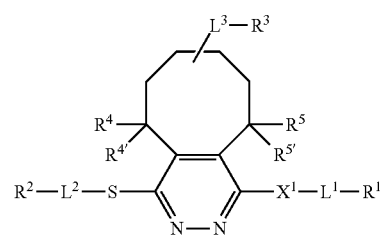

(Ib)

or one of the tautomers thereof, where $X^1$, $L^1$, $L^2$, $L^3$, $R^1$, $R^2$ and $R^3$ are such as defined in formula (I) above, and $R^4$, $R^{4'}$, $R^5$ and $R^{5'}$ are each independently H, hydroxy, halo.

In one embodiment, $R^4$, $R^{4'}$, $R^5$ and $R^{5'}$ all represent H. In another embodiment, $R^4$ and $R^{4'}$ are H, and $R^5$ and $R^{5'}$ are halo, preferably F. In another embodiment, $R^5$ and $R^{5'}$ are H, and $R^4$ and $R^{4'}$ are halo, preferably F. In another embodiment, $R^4$, $R^{4'}$ and $R^{5'}$ are H and $R^5$ is hydroxy.

In another embodiment, the trifunctionalised platforms of formulas (I) have the formula (Ic):

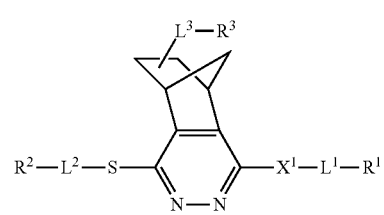

(Ic)

or one of the tautomers thereof, where $X^1$, $L^1$, $L^2$, $L^3$, $R^1$, $R^2$ and $R^3$ are such as defined in formula (I) above.

In one embodiment, the trifunctionalised platforms of formulas (I) have the formula (Id):

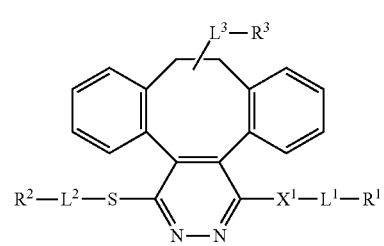

(Id)

or one of the tautomers thereof, where $X^1$, $L^1$, $L^2$, $L^3$, $R^1$, $R^2$ and $R^3$ are such as defined in formula (I) above.

In one embodiment, the trifunctionalised platforms of formulas (I) have the formula (Ie):

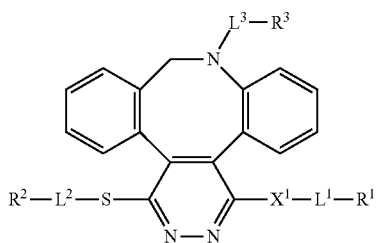

(Ie)

or one of the tautomers thereof, where $X^1$, $L^1$, $L^2$, $L^3$, $R^1$, $R^2$ and $R^3$ are such as defined in formula (I) above.

In one embodiment, the trifunctionalised platforms of formulas (I) have the formula (If):

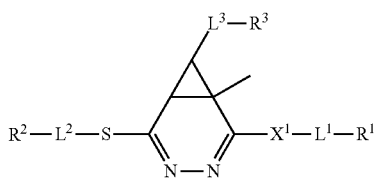

(If)

or one of the tautomers thereof, where $X^1$, $L^1$, $L^2$, $L^3$, $R^1$, $R^2$ and $R^3$ are such as defined in formula (I) above.

In one embodiment, the trifunctionalised platforms of formulas (I) have the formula (Ig):

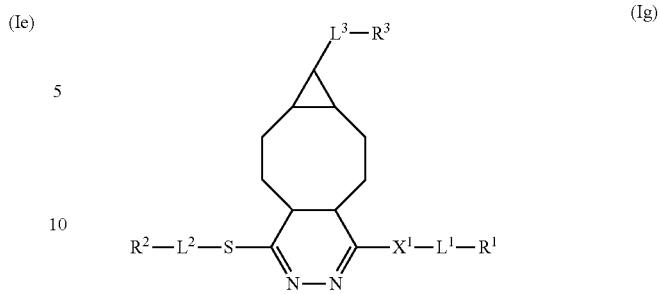

(Ig)

or one of the tautomers thereof, where $X^1$, $L^1$, $L^2$, $L^3$, $R^1$, $R^2$ and $R^3$ are such as defined in formula (I) above.

In one embodiment, the trifunctionalised platforms of formulas (I) have the formula (Ih):

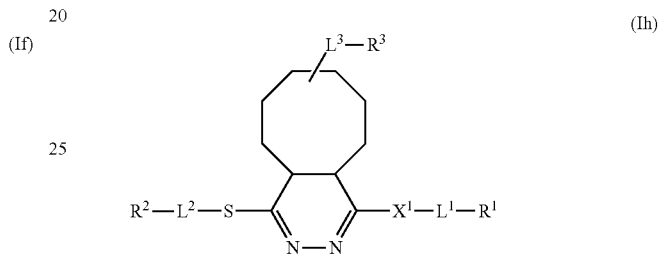

(Ih)

or one of the tautomers thereof, where $X^1$, $L^1$, $L^2$, $L^3$, $R^1$, $R^2$ and $R^3$ are such as defined in formula (I) above.

In one embodiment, the trifunctionalised platform of formula (I) is selected from among:

| Cpd | Structure and Name |
|---|---|
| I-1 | 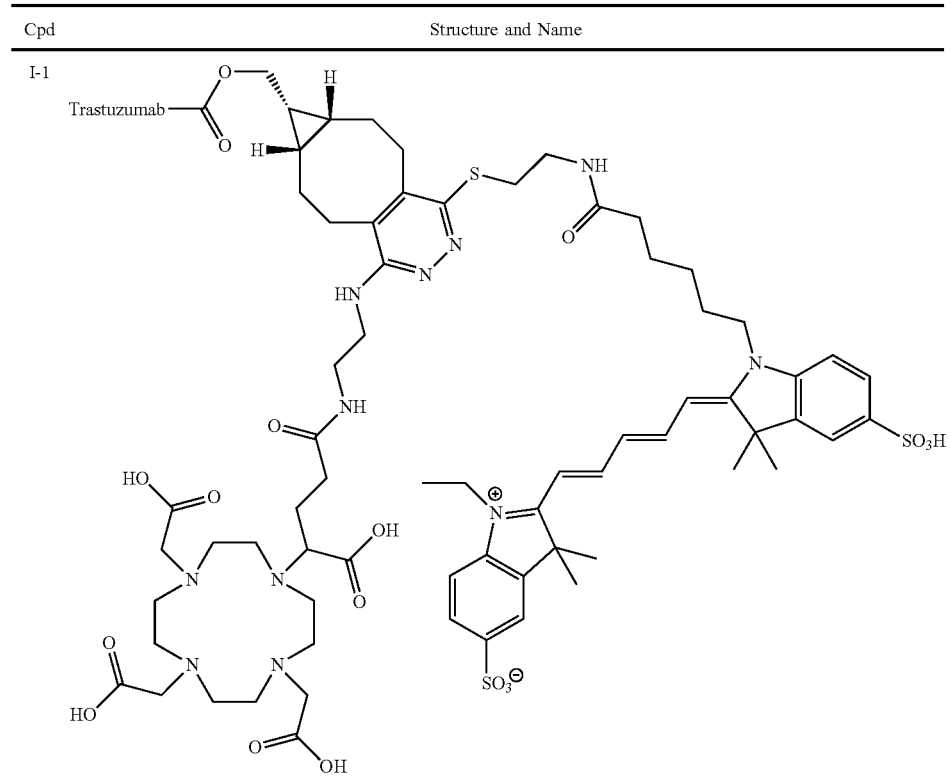<br>Trastuzumab-BCN-pyridazine, NH-DOTAGA, Disulfonated S-cyanine 5.0 |

| Cpd | Structure and Name |
|---|---|
| I-2 | 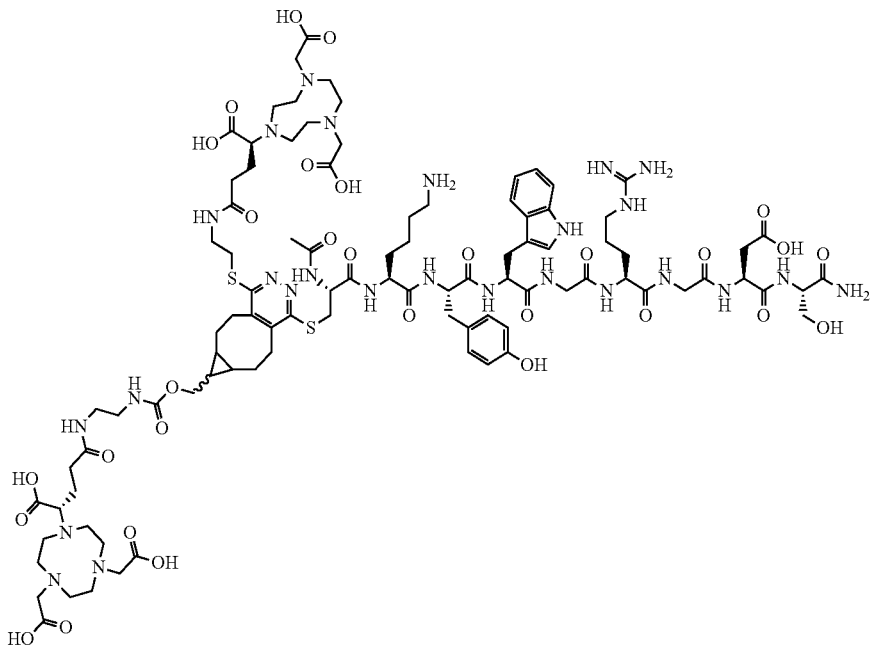 [SMILES: CC(=O)N[C@@H](CSc1nnc(SCCNC(=O)CC[C@@H](C(=O)O)N2CCN(CC(=O)O)CCN(CC(=O)O)CC2)c2c1CCC1C(CC2)C1COC(=O)NCCNC(=O)CC[C@@H](C(=O)O)N1CCN(CC(=O)O)CCN(CC(=O)O)CC1)C(=O)N[C@@H](CCCCN)C(=O)N[C@@H](Cc1ccc(O)cc1)C(=O)N[C@@H](Cc1c[nH]c2ccccc12)C(=O)NCC(=O)N[C@@H](CCCNC(=N)N)C(=O)NCC(=O)N[C@@H](CC(=O)O)C(=O)N[C@@H](CO)C(N)=O]<br><br>(R)-NODAGA-BCN-pyridazine, S-(R)-NODAGA, S-peptide<br><br>2,2'-(7-((1S)-4-((2-((((1-(((2S,5S,11S,17S,20S,23S,26R)-17-((1H-indol-3-yl)methyl)-26-acetamido-1-amino-23-(4-aminobutyl)-5-(carboxymethyl)-11-(3-guanidinopropyl)-20-(4-hydroxybenzyl)-2-(hydroxymethyl)-1,4,7,10,13,16,19,22,25-nonaoxo-3,6,9,12,15,18,21,24-octaazaheptacosan-27-yl)thio)-4-((2-((S)-4-(4,7-bis(carboxymethyl)-1,4,7-triazonan-1-yl)-4-carboxybutanamido)ethyl)thio)-6,6a,7,7a,8,9-hexahydro-5H-cyclopropa[5,6]cycloocta[1,2-d]pyridazin-7-yl)methoxy)carbonyl)amino)ethyl)amino)-1-carboxy-4-oxobutyl)-1,4,7-triazonane-1,4-diyl)diacetic acid |

| Cpd | Structure and Name |
|---|---|
| I-3 | 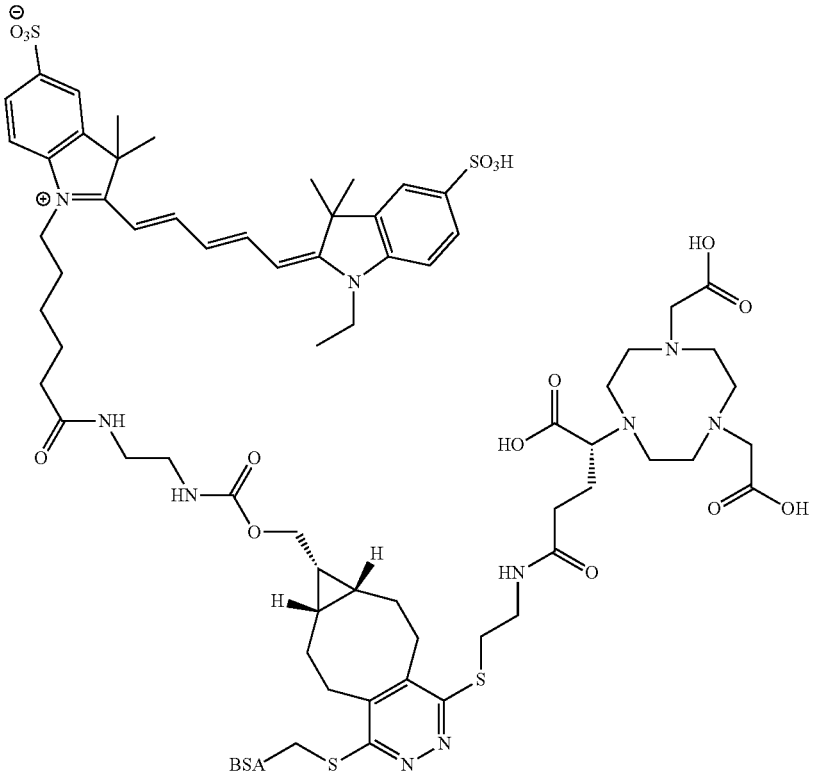<br>Disulfonated S-cyanine 5.0-BCN-pyridazine, S-(R)-NODAGA, S-BSA |
| I-4 | 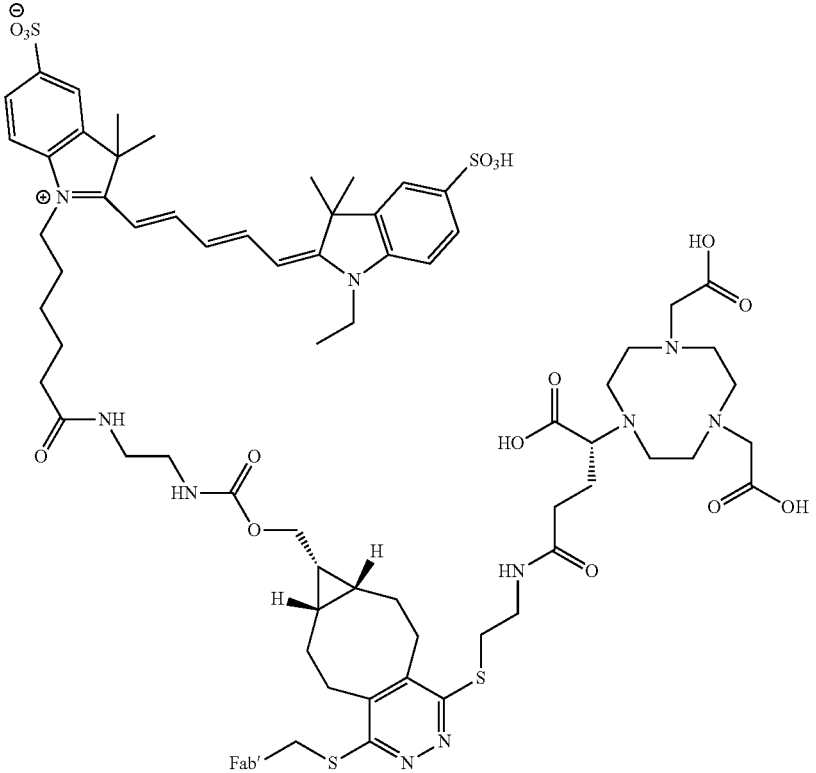<br>Disulfonated S-cyanine 5.0-BCN-pyridazine, S-(R)-NODAGA, S-Fab' |

The compounds described in the present application were named using ChemBioDraw® Ultra version 12.0 (PerkinElmer).

Uses of the Trifunctionalised Platforms (I)

The invention also concerns the use of trifunctionalised platforms of formula (I) as medicinal product and/or for medical imaging.

In one embodiment, the invention concerns the use of the trifunctionalised platforms of the invention in medical imaging. In particular, the following detection methods can be used to detect the compounds of the invention: nuclear imaging including positron emission tomography (PET), single photon emission computed tomography (SPECT) and Cerenkov Luminescence imaging (CLI); magnetic resonance imaging (MRI); optical imaging; fluorescence imaging. In one embodiment, the invention concerns the use of compounds I-1 and/or I-3 such as previously described in medical imaging. In one embodiment, the following detection methods can be used to detect compounds I-1 and/or I-3 such as previously described: nuclear imaging including positron emission tomography (PET), single photon emission computed tomography (SPECT) and Cerenkov Luminescence imaging (CLI); magnetic resonance imaging (MRI); optical imaging; fluorescence imaging; preferably single photon emission computed tomography (SPECT), optical imaging and/or fluorescence imaging.

When the trifunctionalised platforms of the invention can comprise two detectable groups independently, in particular for different imaging techniques, bimodal imaging can be performed. For example, bimodal imaging includes PET/MRI imaging, SPECT/MRI imaging, PET/optical imaging, SPECT/optical imaging or MRI/optical imaging.

In another embodiment, the invention concerns the use of the trifunctionalised platforms of the invention as medicinal product. This is particularly the case when the platform is functionalised by a cytotoxic agent.

When the trifunctionalised platforms of the invention comprise a detectable group and a cytotoxic agent, applications as medicinal product and as theragnostic can be performed.

By «theragnostic» reference is made to the use of medical imaging techniques to detect and/or quantify the presence of the cytotoxic agent in the body or in biopsies.

The trifunctionalised platforms of the invention can also be used as tool to assist operative procedures in image-guided surgery.

The trifunctionalised platforms of the invention can also be used as tool to assist decision-making. In particular, they can be used as partner tool for the selection of patients likely to respond to a targeted therapy.

The trifunctionalised platforms of the invention can also be used to identify new biological targets or to track biomarkers. For example, the association of an optical probe, bioactive group and affinity group such as biotin, can allow the locating (via microscopy) and separation (via affinity chromatography) of the different targets of a bioactive group.

The trifunctionalised platforms of the invention can also be used as tool to assist the development of novel therapeutic agents. Being modular, the platform allows easy in vivo detection of a complex therapeutic agent which associates a bioactive group with a cytotoxic or a solubilising group. The modular nature of the platform allows rapid variation in partners to identify a therapeutic agent having optimal in vivo pharmacological properties.

The trifunctionalised platforms of the invention can also be used as preclinical tool for pharmacological studies. This may concern the use of imaging techniques to identify how therapeutic agents such as ADCs (antibody drug conjugates) evolve in tissues, cells and sub-cells.

The invention further concerns a pharmaceutical composition comprising a formula (I) compound of the invention and a pharmaceutically acceptable vehicle.

In one embodiment, the trifunctionalised platforms of the invention, preferably compounds I-1 and/or I-3 such as previously described, can be used as ex vivo or in vivo multimodal imaging agent.

In one embodiment, when used as imaging agent, compounds I-1 and/or I-3 such as previously described are accumulated preferably in the tumour as opposed to the other organs such as liver, kidneys, muscles, blood, spleen and/or bladder.

Method for Synthesising the Trifunctionalised Platforms (I)

The invention also concerns the method for synthesising the formula (I) trifunctionalised platforms of the invention.

The synthesis method of the invention uses inverse electron demand Diels-Alder reaction starting from a bifunctionalised tetrazine of formula (II) itself able to be obtained from a monofunctionalised tetrazine of formula (IV) (FIG. 1).

Monofunctionalised Tetrazine of Formula (IV)

Therefore, in one embodiment, the synthesis method of the invention comprises a preliminary step to form a monofunctionalised tetrazine of formula (IV):

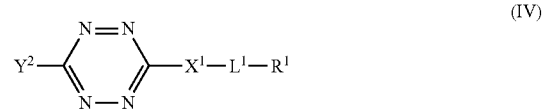

(IV)

where $X^1$, $L^1$ and $R^1$ are such as defined in formula (I) above; and $Y^2$ is a halogen or leaving group selected from among mesylate, tosylate, triflate groups and 3,5-dimethyl-1H-pyrazol-1yl; preferably Y is a halogen, more preferably chlorine;

comprising the nucleophilic monosubstitution of a tetrazine of formula (VI):

(VI)

where $Y^1$ and $Y^2$ are each independently a halogen or leaving group selected from among mesylate, tosylate, triflate groups and 3,5-dimethyl-1H-pyrazol-1yl; preferably $Y^1$ and $Y^2$ are a halogen, more preferably chlorine;

by a nucleophile of formula (VII):

$R^1$-$L^1$-$X^1$—H    (VII)

where $X^1$, $L^1$ and $R^1$ are such as defined in formula (I).

In one embodiment, the forming of the monofunctionalised tetrazine of formula (IV) takes place in an aprotic polar solvent, preferably acetonitrile or anhydrous N,N-dimethylformamide (DMF).

In one embodiment, the forming of the monofunctionalised tetrazine of formula (IV) takes place in a buffer, preferably a buffer fixing pH at a value ranging from 5 to 9, preferably a pH of about 8; preferably the buffer is a borate buffer (2.5 mol/L, pH 8).

In one embodiment, the forming of the monofunctionalised tetrazine of formula (IV) takes place in the presence of a base, preferably N,N-diisopropylethylamine (DIPEA).

In one embodiment, the forming of the monofunctionalised tetrazine of formula (IV) is conducted at a temperature ranging from 0° C. to 37° C., preferably at ambient temperature.

In one embodiment, the step to form the monofunctionalised tetrazine of formula (IV) is conducted for a time ranging from 1 min to 5 hours, preferably from 5 min to 1 hour.

Advantageously, the intermediate (IV), when $X^1$ is S, exhibits excellent selectivity in particular in an aqueous solution buffered at a pH of between 3.5 and 8, for the thiol functions of the cysteines as opposed to the amine or hydroxy functions of lysines and serines respectively, or other potentially reactive functions present on bioactive groups such as peptides or antibodies.

Bifunctionalised Tetrazine of Formula (II)

In one embodiment, the synthesis method of the invention comprises an intermediate step to form a bifunctionalised tetrazine of formula (II):

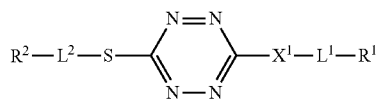

where $X^1$, $L^1$, $L^2$, $R^1$ and $R^2$ are such as defined in formula (I) above;

comprising nucleophilic substitution on a monofunctionalised tetrazine of formula (IV):

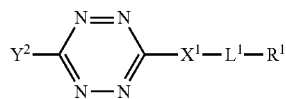

where $X^1$, $L^1$ and $R^1$ are such as defined in formula (I) above; and $Y^2$ is a halogen or leaving group selected from among mesylate, tosylate, triflate groups and 3,5-diméthyl-1H-pyrazol-1yl; preferably $Y^2$ is a halogen, more preferably chlorine;

by a thiol of formula (V):

$R^2$-$L^2$-SH  (V)

where $L^2$ and $R^2$ are such as defined in formula (I).

In one embodiment, the forming of the bifunctionalised tetrazine of formula (II) takes place in a polar solvent, preferably anhydrous N,N-dimethylformamide (DMF) or distilled water.

In one embodiment, the forming of the bifunctionalised tetrazine of formula (II) takes place in the presence of a buffer, preferably a buffer fixing pH at a value ranging from 3.5 to 8, preferably a pH of about 7; preferably the buffer is a phosphate buffer.

In one embodiment, the forming of the bifunctionalised tetrazine of formula (II) takes placed in the presence of a base, preferably N,N-diisopropylethylamine (DIPEA).

In one embodiment, the forming of the bifunctionalised tetrazine of formula (II), preferably when $X^1$ is S, is conducted at a temperature ranging from 4° C. to 37° C., preferably at ambient temperature of 25° C.

In another embodiment, the forming of the bifunctionalised tetrazine of formula (II), preferably when $X^1$ is NH, is conducted at a temperature ranging from 50° C. to 90° C., preferably at a temperature ranging from 70° to 80° C., more preferably at a temperature of 75° C.

In one embodiment, the step to form the bifunctionalised tetrazine of formula (II) is conducted for a time ranging from 10 seconds to 5 hours, preferably from 3.5 minutes to 0.5 hour.

Trifunctionalised Tetrazine of Formula (I)

The synthesis method of the invention comprises a step to form the trifunctionalised platform of formula (I):

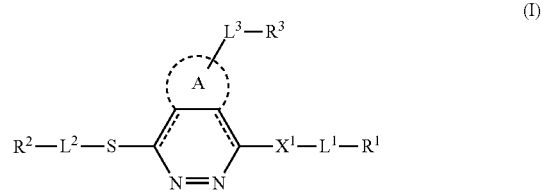

or one of the tautomers thereof, where A, $X^1$, $L^1$, $L^2$, $L^3$, $R^1$, $R^2$, and $R^3$ are such as previously described;

comprising the contacting of a bifunctionalised tetrazine of formula (II):

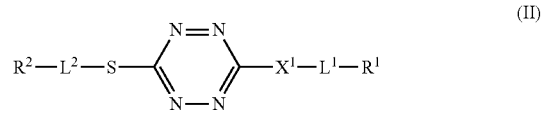

where $X^1$, $L^1$, $L^2$, $R^1$ and $R^2$ are such as described in formula (I);

with an alkyne or alkene or formula (III):

where $L^3$ and $R^3$ are such as described in formula (I);

------ represents a triple bond or double bond, preferably a triply bond; and ring A represents a cycloalkene, cycloalkyne or heterocycloalkyne group, optionally substituted by one or more groups selected from among alkyl, aryl, halo, hydroxy and heteroaryl; preferably the group represented by A is trans-bicyclo[6.1.0]nonene, trans-cyclooctene, bicyclo[6.1.0]nonyne, cyclooctyne, difluorocyclooctyne, hydroxycyclooctyne, methylcyclopropene, norbornene, 5,6-didehydro-11,12-dihydrodibenzo[a,e][8]annulene, 11,12-didehydro-5,6-dihydrodibenzo[b,f]azocine.

In one embodiment, the dihydropyridazine product obtained when (III) is an alkene can optionally undergo an additional oxidation reaction to form the corresponding pyridazine.

In one embodiment, the formula (III) compounds are those of formula (IIIa), (IIIb-1), (IIIb-2), (IIIb-3), (IIIc), (IIId), (IIIe), (IIIf), (IIIg), (IIIh):

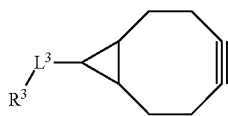
(IIIa)

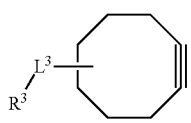
(IIIb-1)

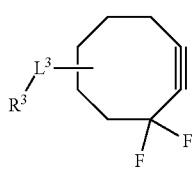
(IIIb-2)

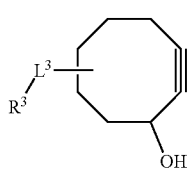
(IIIb-3)

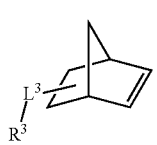
(IIIc)

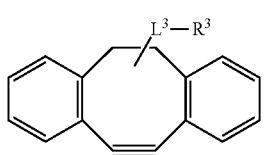
(IIId)

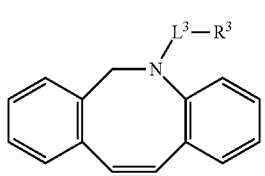
(IIIe)

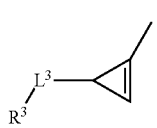
(IIIf)

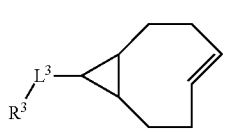
(IIIg)

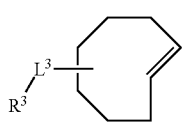
(IIIh)

where $L^3$ and $R^3$ are such as defined above.

In one embodiment, the forming of the trifunctionalised platform of formula (I) takes placed in an aprotic polar solvent, preferably dimethylsulfoxide (DMSO).

In one embodiment, the forming of the trifunctionalised platform of formula (I) takes place in the presence of a buffer, preferably a buffer fixing pH at a value ranging from 4 to 9, preferably a pH of about 7.4; preferably the buffer is phosphate-buffered saline (PBS).

In one embodiment, the forming of the trifunctionalised platform of formula (I) is conducted at temperatures ranging from 20° C. to 50° C., preferably at ambient temperature at a physiological temperature of about 37° C.

In one embodiment, the step to form the trifunctionalised platform of formula (I) is conducted for a time ranging from 30 minutes to 20 hours, preferably from 50 minutes to 16 hours.

Synthesis Intermediates: Bifunctionalised Tetrazine Platforms (II)

The invention also concerns a bifunctionalised tetrazine platform of formula (II), such as described below, functionalised by a least one group detectable by imaging. Said bifunctionalised tetrazine platform can be used to obtain the trifunctionalised platform of formula (I) of the invention.

The invention therefore concerns a bifunctionalised tetrazine of formula (II):

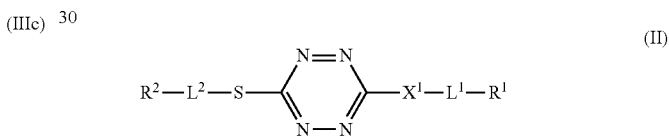
(II)

where:

$X^1$ is S, NH or O;

$L^1$ and $L^2$ are each independently a single bond or a spacer selected from among alkyl, alkoxy, aryl, arylalkyl, alkylaryl, heteroaryl, heteroarylalkyl, alkylheteroaryl, alkenyl and alkynyl groups, wherein the alkyl groups are optionally interrupted and/or terminated by one or more groups selected from among —O—, —NH—, —S—, —C(O)—, —C(O)NH— and —NHC(O)—; preferably $L^1$ and $L^2$ are each independently an alkyl or alkylaryl spacer optionally interrupted and/or terminated by one or more groups selected from among-O—, —C(O)—, —NH— and —NHC(O)—; more preferably, $L^1$ and $L^2$ are each independently a spacer selected from among —CH$_2$CH$_2$NH—, —NHCH$_2$CH$_2$NH—, —CH$_2$OCONHCH$_2$CH$_2$NHCOCH$_2$CH$_2$—, —CH$_2$OCO—, —COCH$_2$CH$_2$NH—, —CH$_2$CH$_2$NHCOCH$_2$CH$_2$— and —CH$_2$CH$_2$NHCO-p-Ph-;

$R^1$ and $R^2$ are each independently a detectable group, bioactive group, cytotoxic agent, affinity group or solubilising group;

provided that at least one of $R^1$ and $R^2$ is a detectable group.

In one embodiment, the bifunctionalised platform of formula (II) is selected from among:

| Cpd | Structure, Short name, Chemical name |
|---|---|
| II-1 | 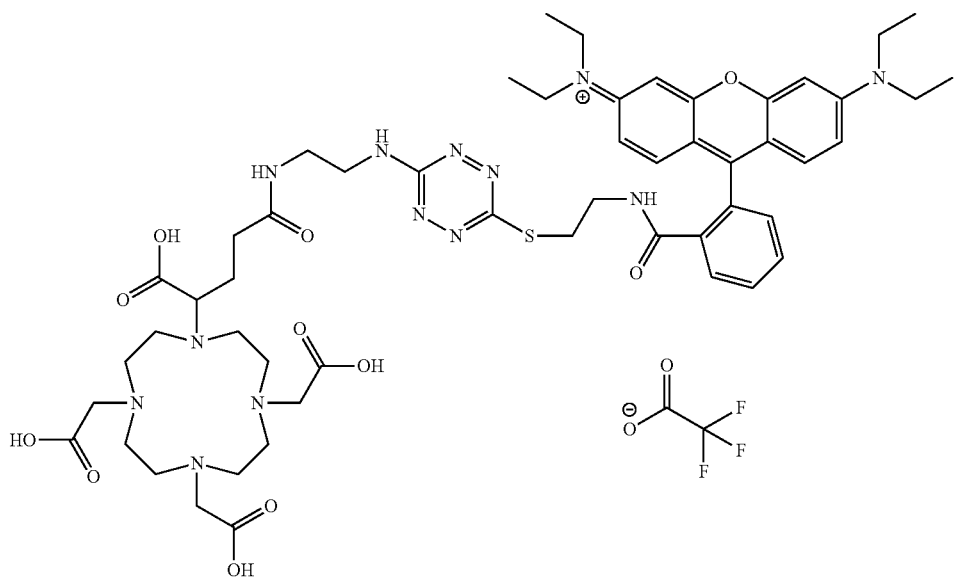 [SMILES: CCN(CC)c1ccc2c(-c3ccccc3C(=O)NCCSc3nnc(NCCNC(=O)CCC(C(=O)O)N4CCN(CC(=O)O)CCN(CC(=O)O)CCN(CC(=O)O)CC4)nn3)c3ccc(=[N+](CC)CC)cc-3oc2c1 ; O=C([O-])C(F)(F)F]<br>DOTAGA-NH-Tz-S-Rhodamine B<br>N-(9-(2-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)carbamoyl)phenyl)-6-(diethylamino)-3H-xanthen-3-ylidene)-N-ethylethanaminium 2,2,2-trifluoroacetate |
| II-2 | 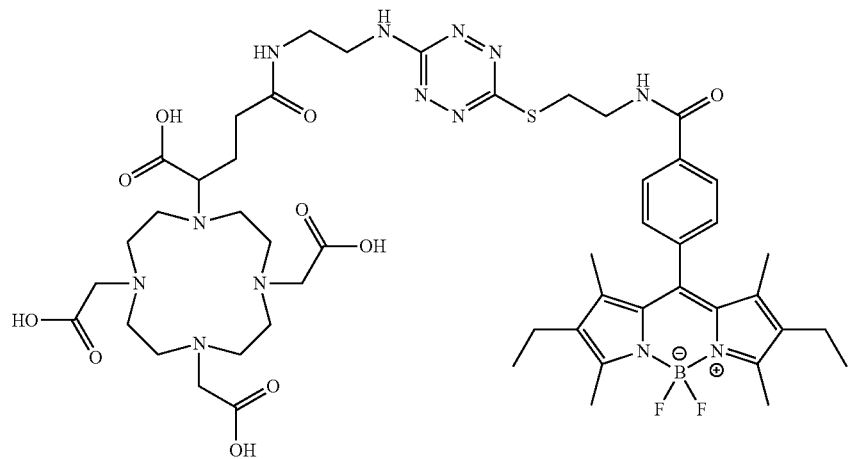 [SMILES: CCC1=C(C)C2=C(c3ccc(C(=O)NCCSc4nnc(NCCNC(=O)CCC(C(=O)O)N5CCN(CC(=O)O)CCN(CC(=O)O)CCN(CC(=O)O)CC5)nn4)cc3)c3c(C)c(CC)c(C)n3[B-](F)(F)[N+]2=C1C]<br>DOTAGA-NH-Tz-S-BODIPY<br>10-(4-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)carbamoyl)phenyl)-2,8-diethyl-5,5-difluoro-1,3,7,9-tetramethyl-5H-dipyrrolo[1,2-c:2',1'-f][1,3,2]diazaborinin-4-ium-5-uide |

| Cpd | Structure, Short name, Chemical name |
|---|---|
| II-3 | 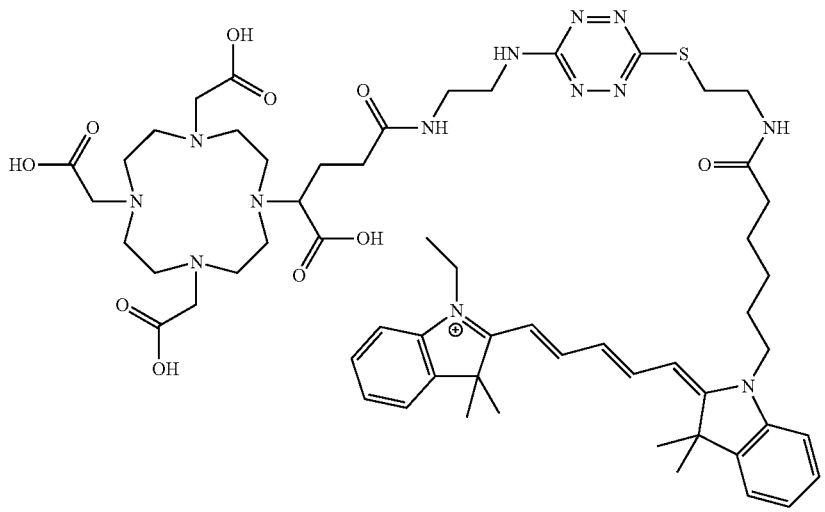 [SMILES: CC[N+]1=C(/C=C/C=C/C=C2/N(CCCCCC(=O)NCCSc3nnc(NCCNC(=O)CCC(C(=O)O)N4CCN(CC(=O)O)CCN(CC(=O)O)CCN(CC(=O)O)CC4)nn3)c3ccccc3C2(C)C)C(C)(C)c2ccccc21]
DOTAGA-NH-Tz-S-cyanine 5.0
2-((1E,3E,5E)-5-(1-(6-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)amino)-6-oxohexyl)-3,3-dimethylindolin-2-ylidene)penta-1,3-dien-1-yl)-1-ethyl-3,3-dimethyl-3H-indol-1-ium |
| II-4 | 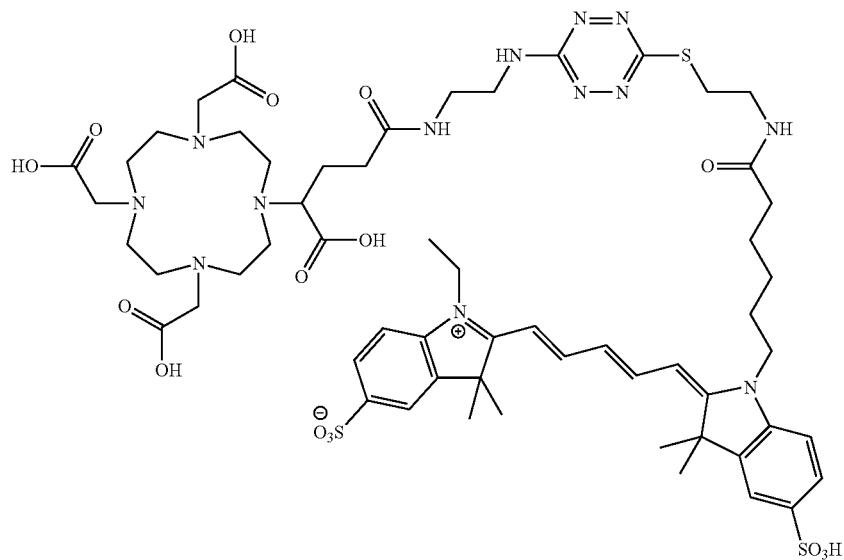
DOTAGA-NH-Tz-disulfonated S-cyanine 5.0
2-((1E,3E,5E)-5-(1-(6-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)amino)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate |

| Cpd | Structure, Short name, Chemical name |
|---|---|
| II-5 | 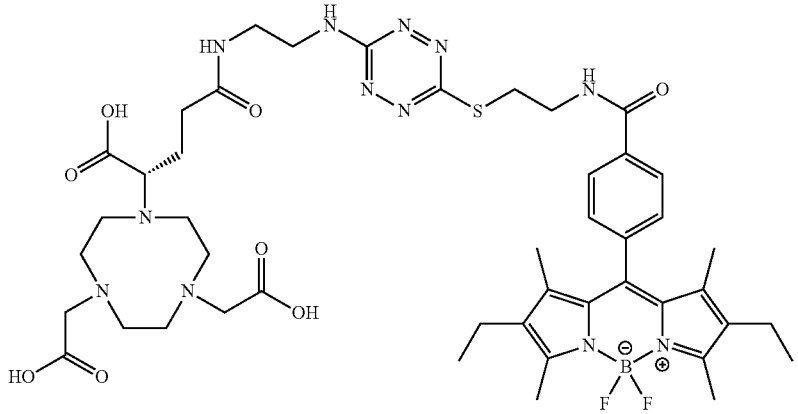 [SMILES: CCC1=C(C)C2=C(c3ccc(C(=O)NCCSc4nnc(NCCNC(=O)CC[C@@H](C(=O)O)N5CCN(CC(=O)O)CCN(CC(=O)O)CC5)nn4)cc3)c3c(C)c(CC)c(C)n3[B-](F)(F)[N+]2=C1C]
(R)-NODAGA-NH-Tz-S-BODIPY
(S)-10-(4-((2-((6-((2-(4-(4,7-bis(carboxymethyl)-1,4,7-triazonan-1-yl)-4-carboxybutanamido)ethyl)amino)-1,2,4,5-tetrazin-3-yl)thio)ethyl)carbamoyl)phenyl)-2,8-diethyl-5,5-difluoro-1,3,7,9-tetramethyl-5H-dipyrrolo[1,2-c:2',1'-f][1,3,2]diazaborinin-4-ium-5-uide |
| II-6 | 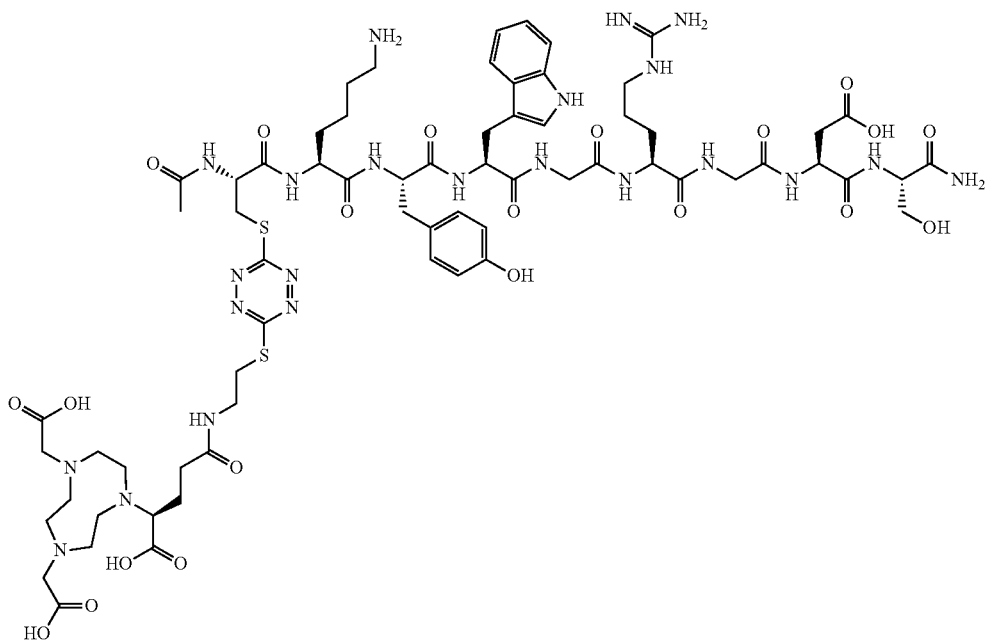 [SMILES: CC(=O)N[C@@H](CSc1nnc(SCCNC(=O)CC[C@@H](C(=O)O)N2CCN(CC(=O)O)CCN(CC(=O)O)CC2)nn1)C(=O)N[C@@H](CCCCN)C(=O)N[C@@H](Cc1ccc(O)cc1)C(=O)N[C@@H](Cc1c[nH]c2ccccc12)C(=O)NCC(=O)N[C@@H](CCCNC(=N)N)C(=O)NCC(=O)N[C@@H](CC(=O)O)C(=O)N[C@@H](CO)C(N)=O]
(R)-NODAGA-S-Tz-S-peptide
2,2'-(7-((S)-4-((2-((6-(((2S,5S,11S,17S,20S,23S,26R)-17-((1H-indol-3-yl)methyl)-26-acetamido-1-amino-23-(4-aminobutyl)-5-(carboxymethyl)-11-(3-guanidinopropyl)-20-(4-hydroxybenzyl)-2-(hydroxymethyl)-1,4,7,10,13,16,19,22,25-nonaoxo-3,6,9,12,15,18,21,24-octaazaheptacosan-27-yl)thio)-1,2,4,5-tetrazin-3-yl)thio)ethyl)amino)-1-carboxy-4-oxobutyl)-1,4,7-triazonane-1,4-diyl)diacetic acid |

| Cpd | Structure, Short name, Chemical name |
|---|---|
| II-7 | 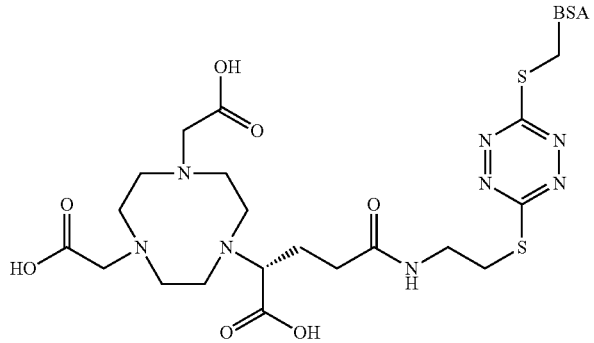<br>(R)-NODAGA-S-Tz-S-BSA |
| II-8 | 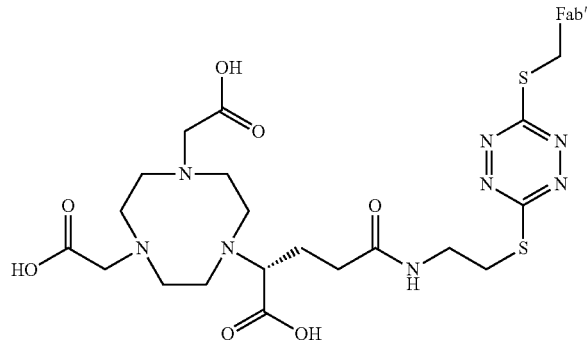<br>(R)-NODAGA-S-Tz-S-Fab' |

Synthesis Intermediates: Monofunctionalised Tetrazine Platforms (IV)

The invention also concerns a monofunctionalised tetrazine platform of formula (IV), such as described below. Said monofunctionalised tetrazine platform can be used to obtain the bifunctionalised tetrazine platform of formula (II) described above, thereby giving access to the trifunctionalised platform of formula (I) of the invention.

The invention therefore concerns a monofunctionalised tetrazine of formula (IV):

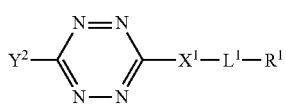

where:

$Y^2$ is a halogen or leaving group selected from among mesylate, tosylate, triflate groups and 3,5-dimethyl-1H-pyrazol-1yl; preferably $Y^2$ is a halogen, more preferably chlorine;

$X^1$ is S, NH or O;

$L^1$ is a single bond or spacer selected from among alkyl, alkoxy, aryl, arylalkyl, alkylaryl, heteroaryl, heteroarylalkyl, alkylheteroaryl, alkenyl and alkynyl groups, wherein the alkyl groups are optionally interrupted and/or terminated by one or more groups selected from among —O—, —NH—, —S—, —C(O)—, —C(O)NH— and —NHC(O)—; preferably $L^1$ is an alkyl or alkylaryl spacer, optionally interrupted and/or terminated by one or more groups selected from among —O—, —C(O)—, —NH— and —NHC(O)—; more preferably $L^1$ is a spacer selected from among —CH₂CH₂NH—, —NHCH₂CH₂NH—, —CH₂OCONHCH₂CH₂NHCOCH₂CH₂—, —CH₂OCO—, —COCH₂CH₂NH—, —CH₂CH₂NHCOCH₂CH₂— and —CH₂CH₂NHCO-p-Ph-; and $R^1$ is a detectable group, bioactive group, cytotoxic agent, affinity group or solubilising group.

In one embodiment, the monofunctionalised tetrazine of formula (IV) is selected among:

| Cpd | Structure | Short name, Chemical name |
|---|---|---|
| IV-1 | 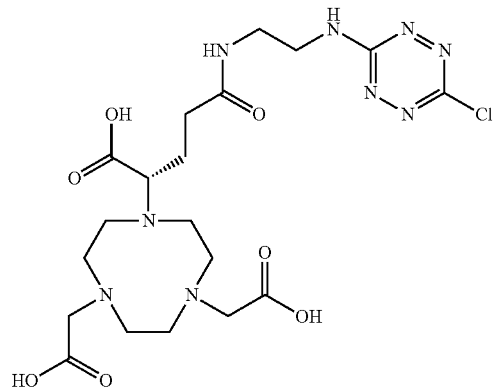 [SMILES: O=C(O)CN1CCN(CC(=O)O)CCN([C@@H](CCC(=O)NCCNc2nnc(Cl)nn2)C(=O)O)CC1] | NODAGA-NH-Tz-Cl<br>(S)-2,2'-(7-(1-carboxy-4-((2-((6-chloro-1,2,4,5-tetrazin-3-yl)amino)ethyl)amino)-4-oxobutyl)-1,4,7-triazonane-1,4-diyl)diacetic acid |
| IV-2 | 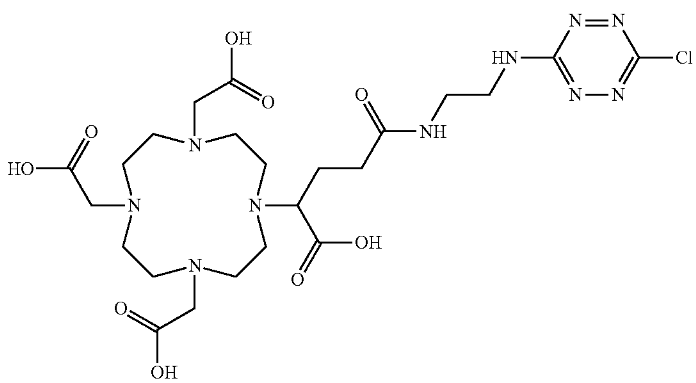 [SMILES: O=C(O)CN1CCN(CC(=O)O)CCN(C(CCC(=O)NCCNc2nnc(Cl)nn2)C(=O)O)CCN(CC(=O)O)CC1] | DOTAGA-NH-Tz-Cl<br>2,2',2''-(10-(1-carboxy-4-((2-((6-chloro-1,2,4,5-tetrazin-3-yl)amino)ethyl)amino)-4-oxobutyl)-1,4,7,10-tetraazacyclododecane-1,4,7-triyl)triacetic acid |
| IV-3 | 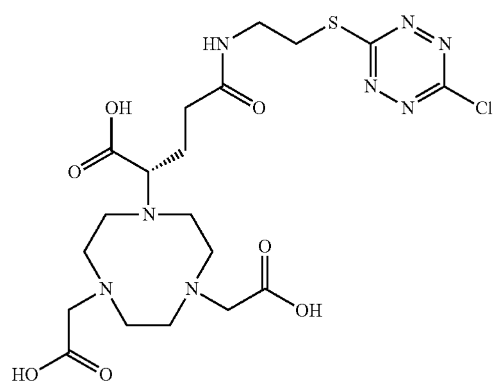 [SMILES: O=C(O)CN1CCN(CC(=O)O)CCN([C@@H](CCC(=O)NCCSc2nnc(Cl)nn2)C(=O)O)CC1] | (R)-NODAGA-S-Tz-Cl<br>(S)-2,2'-(7-(1-carboxy-4-((2-((6-chloro-1,2,4,5-tetrazin-3-yl)thio)ethyl)amino)-4-oxobutyl)-1,4,7-triazonane-1,4-diyl)diacetic acid |
| IV-4 | 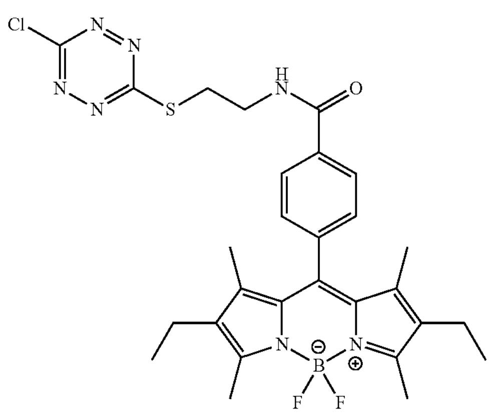 [SMILES: CCC1=C(C)C2=C(c3ccc(C(=O)NCCSc4nnc(Cl)nn4)cc3)c3c(C)c(CC)c(C)n3[B-](F)(F)[N+]2=C1C] | BODIPY-S-Tz-Cl<br>10-(4-((2-((6-chloro-1,2,4,5-tetrazin-3-yl)thio)ethyl)carbamoyl)phenyl)-2,8-diethyl-5,5-difluoro-1,3,7,9-tetramethyl-5H-dipyrrolo[1,2-c:2',1'-f][1,3,2]diazaborinin-4-ium-5-uide |

| Cpd | Structure | Short name, Chemical name |
|---|---|---|
| IV-5 | 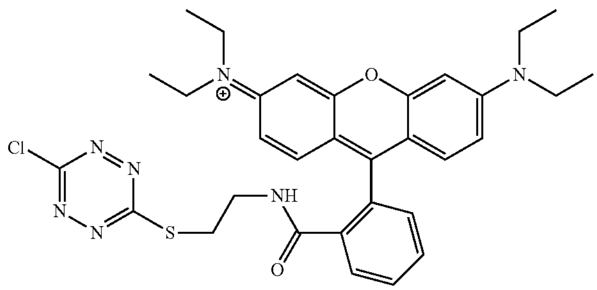 [SMILES: CCN(CC)c1ccc2c(-c3ccccc3C(=O)NCCSc3nnc(Cl)nn3)c3ccc(=[N+](CC)CC)cc-3oc2c1] | Rhodamine B-S-Tz-Cl<br>N-(9-(2-((2-((6-chloro-1,2,4,5-tetrazin-3-yl)thio)ethyl)carbamoyl)phenyl)-6-(diethylamino)-3H-xanthen-3-ylidene)-N-ethylethanaminium |
| IV-6 | 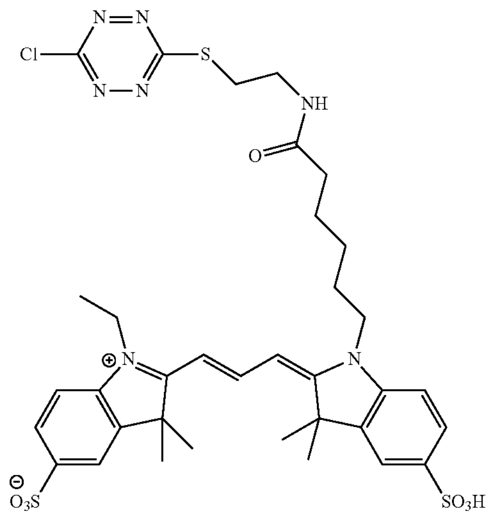 | Disulfonated cyanine 3.0-S-Tz-Cl<br>2-((1E,3E)-3-(1-(6-((2-((6-chloro-1,2,4,5-tetrazin-3-yl)thio)ethyl)amino)-6-oxohexyl)-3,3-dimethyl-5-sulfoindolin-2-ylidene)prop-1-en-1-yl)-1-ethyl-3,3-dimethyl-3H-indol-1-ium-5-sulfonate |

EXAMPLES

Figure 1:
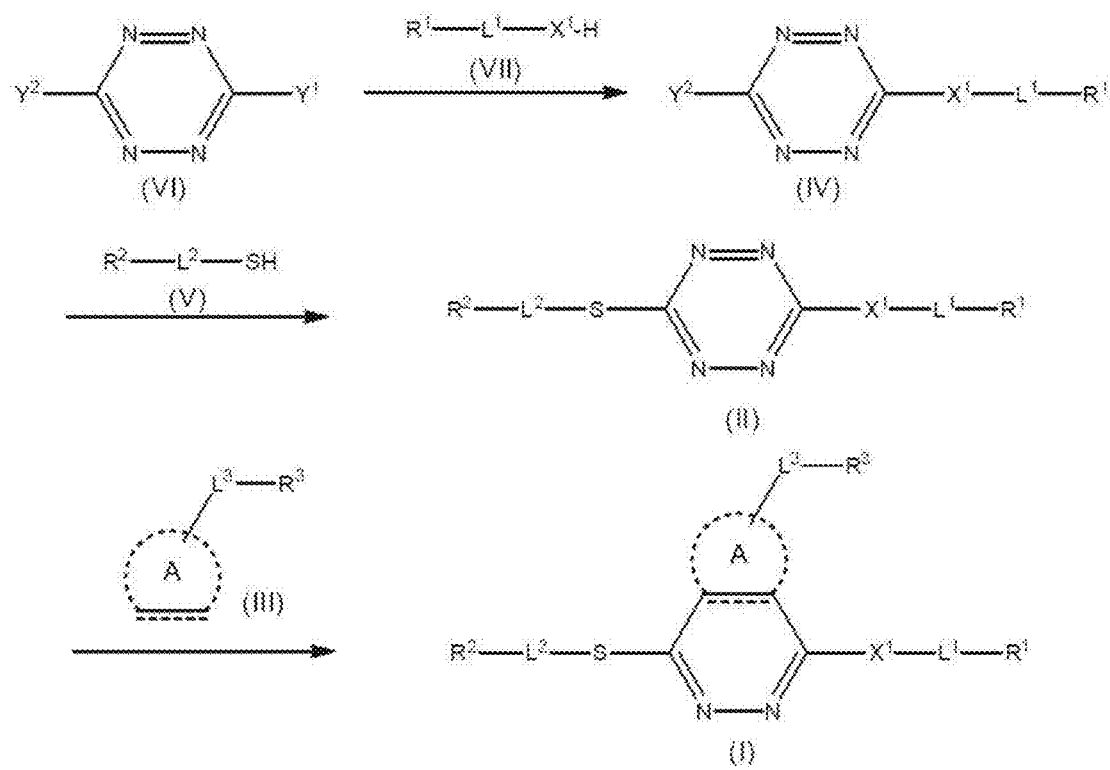
FIG. 1 illustrates a scheme for synthesis of the trifunctionalised platforms (1) of the invention involving the mono- and bi-functionalised tetrazine intermediates (IV) and (II).

The present invention will be better understood on reading the following examples giving a nonlimiting illustration of the invention.

Abbreviations

ACN: acetonitrile
BCN: bicylononyne

BODIPY: boron-dipyromethene
DCM: dichloromethane
DIPEA: diisopropylethylamine
DMF: dimethylformamide
DMSO: dimethylsulfoxide
DODT: 3,6-dioxa-1,8-octanedithiol
DOTAGA: 2-(4,7,10-tris(carboxymethyl)-1,4,7,10-tetraazacyclododecan-1-yl)pentanedioic acid
Fab': Fab' fragment of pertuzumab (anti-HER2)
HATU: 1-[Bis(dimethylamino)methylene]-1H-1,2,3-triazolo[4,5-b]pyridinium 3-oxide hexafluorophosphate
HPLC: high performance liquid chromatography
MeOH: methanol
NODAGA: 2-(4,7-bis(carboxymethyl)-1,4,7-triazonan-1-yl)pentanedioic acid
PBS: phosphate buffered saline
rpm: revolutions per minute
TCO: trans-cyclooctene
TFA: trifluoroacetic acid
TIS: triisopropylsilane
TSTU: N,N,N',N'-tetramethyl-O—(N-succinimidyl)uronium tetrafluoroborate Material Unless otherwise stated, the chemical reagents and solvents were obtained from usual suppliers of chemical products (Sigma-Aldrich, Alfa-Aesar, Fisher Scientic, BioSolve) and were used without prior purification. The polyazamacrocycles used were obtained from Chematech (Quetigny, France). The optical probes of the Cyanine family were courteously supplied by Prof. Anthony Romieu (Université de Bourgogne) and synthesised following the protocols described in the literature.

Purifications with semi-preparative HPLC were performed on an UltiMate 3000 Dionex system (Thermo Scientific) equipped with UV-visible detector on a reverse phase column (C18).

Purifications with flash chromatography were performed on a puriFlash®430 system (Interchim) using pre-packed Interchim columns in normal phase or reverse phase (size of particles 15 µm or 25 µm).

LC-MS analyses were performed on an UltiMate 3000 liquid chromatography system equipped with DAD detector and coupled to a MSQ Plus mass detector (Thermo Scientific), in ESI mode. Chromatographies were carried out on a Kinetex™ $C_{18}$ column, 2.6 µm, 100 Å, 50×2.1 mm (Phenomenex) with HPLC-quality eluents (Eluent A: $H_2O$ 0.1% formic acid (FA); eluent B: acetonitrile 0.1% FA) with 5% to 100% gradient of B in 5 min, 100% plateau for 1.5 min. The purity of the compounds was determined from LC-MS chromatograms at 214 nm wavelength.

High resolution mass spectra (HRMS ESI) of the end compounds were performed on a PACSMUB platform (DIJON, France), with LTQ Orbitrap XL mass spectrometer, equipped with an ESI source (Thermo Scientific).

$^1$H NMR spectra were obtained on a Bruker Avance III NanoBay NMR spectrometer. The spectra were obtained at ambient temperature. The following abbreviations were used to describe multiplicity of signals: s=singlet, d=doublet, t=triplet, m=multiplet.

Part I. Chemical Synthesis

1. Amine Intermediates of Formula (VII)

1.1. Cyanine 5.0-$NH_2$ 2-((1E,3E,5E)-5-(1-(6-((2-ammonioethyl)amino)-6-oxohexyl)-3,3-dimethylindolin-2-ylidene)penta-1,3-dien-1-yl)-1-ethyl-3,3-dimethyl-3H-indol-1-ium

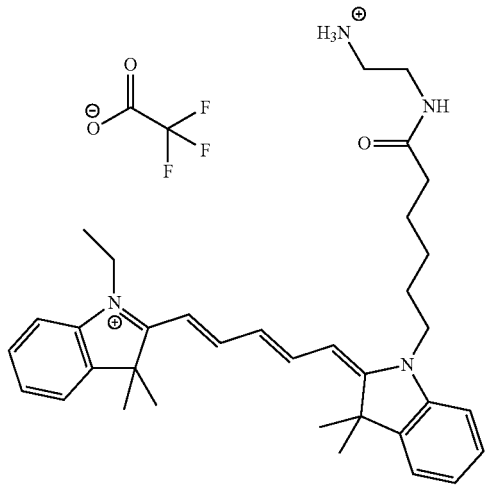 [SMILES: CC[N+]1=C(/C=C/C=C/C=C2/N(CCCCCC(=O)NCC[NH3+])c3ccccc3C2(C)C)C(C)(C)c2ccccc21 ; O=C([O-])C(F)(F)F]

Cyanine 5.0 (20.0 mg, 32.7 µmol), TSTU (11.8 mg, 39.3 µmol, 1.2 eq) and DIPEA (6.9 µL, 39.3 µmol, 1.2 eq) were dissolved in 700 µL of anhydrous DMF. The reaction medium was left under agitation at ambient temperature for 1 h, after which ethylenediamine (21.8 µL, 327 µmol, 10.0 eq) and DIPEA (57.1 µL, 327 µmol, 10.0 eq) were added. After 25 min, the solvent was removed under reduced pressure. Purification of the reaction product was conducted using reverse phase semi-preparative HPLC (eluents: $H_2O$ 0.1% TFA, ACN 0.1% TFA).

Cyanine 5.0-$NH_2$ was obtained in the form of a blue powder (11.1 mg, 52% TFA salt). $^1$H NMR (500 MHz, $CDCl_3$) ∂: 1.36 (t, 3H; $CH_3$), 1.41 (m, 2H; $CH_2$), 1.64 (s, 6H; $CH_3$), 1.65 (s, 6H; $CH_3$), 1.67 (m, 2H; CH2), 1.74 (m, 2H; $CH_2$), 2.24 (t, 2H; $CH_2$), 3.13 (m, 2H; $CH_2$), 3.51 (m, 2H; $CH_2$), 3.94 (t, 2H; $CH_2$), 4.01 (q, 2H; $CH_2$), 6.13 (d, 1H; CH), 6.16 (d, $^3J$=13.5 Hz, 1H; CH), 6.58 (t, 2H; CH), 7.07 (m, 2H; $CH_{Ar}$), 7.19 (m, 2H; $CH_{Ar}$), 7.32 (m, 4H; $CH_{Ar}$), 7.81 (dd, 2H; CH), 8.26 (t, 1H; CONH), 8.38 (m, 3H; $NH_3^+$); MS: $C_{35}H_{47}N_4^+$ ([M]$^+$) m/z calculated: 539.4; found: 539.4.

2. Thiol Intermediates of Formula (V) and (VII)

2.1. Rhodamine B-SH

N-(6-(diethylamino)-9-(2-((2-mercaptoethyl)carbamoyl)phenyl)-3H-xanthen-3-ylidene)-N-ethylethanaminium

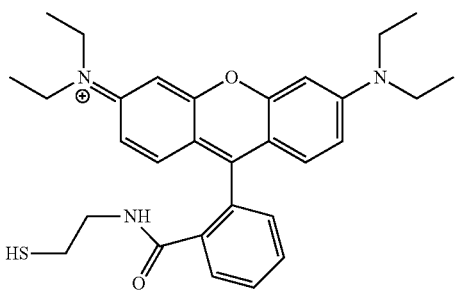 [SMILES: CCN(CC)c1ccc2c(-c3ccccc3C(=O)NCCS)c3ccc(=[N+](CC)CC)cc-3oc2c1]

Rhodamine B (200 mg, 418 µmol), HATU (191 mg, 502 µmol, 1.2 eq) and DIPEA (87 µL, 502 µmol, 1.2 eq) were dissolved in 2 mL of anhydrous DMF. The solution was left under agitation at ambient temperature for 2 h, and 2-aminoethanethiol hydrochloride (95 mg, 836 µmol, 2.0 eq) and DIPEA (139 µL, 836 µmol, 2.0 eq) were afterwards added to the reaction medium. After 2 h, the DMF was removed under reduced pressure. Purification of the reaction product was obtained with flash chromatography on silica (eluents: DCM/MeOH). Rhodamine B-SH was obtained in the form of a purple powder (179.3 mg, 85%). $^1$H NMR (300 MHz, CDCl$_3$): Equilibrium between the non-cyclic and cyclic forms of rhodamine; MS: $C_{30}H_{36}N_3O_2S^+$ ([M]$^+$) m/z calculated: 502.3; found: 502.2.

2.2. BODIPY-SH 2,8-diethyl-5,5-difluoro-10-(4-((2-mercaptoethyl)carbamoyl)phenyl)-1,3,7,9-tetramethyl-5H-dipyrrolo[1,2-c:2',1'-f][1,3,2]diazaborinin-4-ium-5-uide

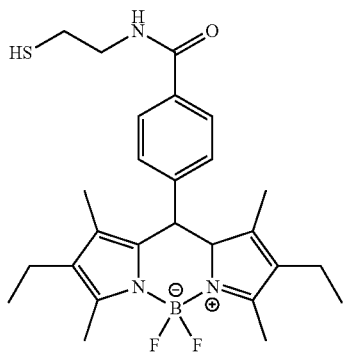 [SMILES: CCC1=C(C)C2C(c3ccc(C(=O)NCCS)cc3)c3c(C)c(CC)c(C)n3[B-](F)(F)[N+]2=C1C]

BODIPY-COOH (100 mg, 235 µmol) and carbonyldiimidazole (46 mg, 282 µmol, 1.2 eq) were dissolved in 1 mL of anhydrous DMF. The solution was left under agitation at ambient temperature for 1 h, after which 2-aminoethanethiol hydrochloride (54 mg, 470 µmol, 2.0 eq) was added. After 20 min, the DMF was removed under reduced pressure. Purification of the reaction product was performed with flash chromatography on silica (eluents: DCM/MeOH). BODIPY-SH was obtained in the form of a red powder (65.0 mg, 57%). $^1$H NMR (300 MHz, CDCl$_3$): ∂=0.95 (t, 6H; CH$_3$), 1.23 (s, 6H; CH$_3$), 1.43 (t, 1H; SH), 2.27 (q, 4H; CH$_2$), 2.51 (s, 6H; CH$_3$), 2.81 (dt, 2H; CH$_2$), 3.66 (dt, 2H; CH$_2$), 6.70 (t, 1H; NH), 7.37 (d, 2H; CH$_{Ar}$), 8.18 (d, 2H; CH$_{Ar}$) MS: $C_{26}H_{32}BFN_3OS^+$ ([M–F]$^+$) m/z calculated: 464.2; found: 464.1.

2.3. Disulfonated Cyanine 3.0-SH

1-Ethyl-2-((1E,3E)-3-(1-(6-((2-mercaptoethyl)amino)-6-oxohexyl)-3,3-dimethyl-5-sulfoindolin-2-ylidene)prop-1-en-1-yl)-3,3-dimethyl-3H-indol-1-ium-5-sulfonate

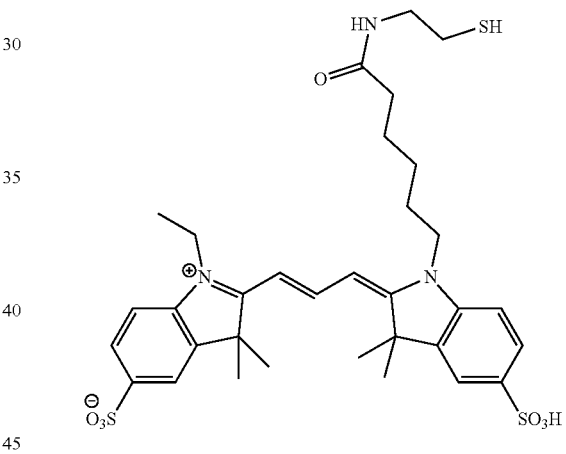

Disulfonated cyanine 3.0 (24.5 mg, 38.8 µmol), TSTU (16.1 mg, 53.5 µmol, 1.4 eq) and DIPEA (10.0 µL, 57.3 µmol, 1.5 eq) were dissolved in 1 mL of anhydrous DMF. The solution was left under agitation at ambient temperature for 15 min, and 2-aminoethanethiol hydrochloride (11.0 mg, 96.8 µmol, 2.5 eq) and DIPEA (13.6 µL, 77.7 µmol, 2.0 eq) were added afterwards. After 25 min at ambient temperature the reaction was complete. Dithiothreitol (15.5 mg, 100 µmol, 2.6 eq) and water (400 µL) were added and the solution left under agitation for 3 h at ambient temperature. The solvents were afterwards removed under reduced pressure. Purification of the reaction product was performed with reverse phase semi-preparative HPLC (eluents: H$_2$O 0.1% TFA, ACN 0.1% TFA). Disulfonated cyanine 3.0-SH was obtained in the form of a pink powder (18.2 mg, 68%). $^1$H NMR (300 MHz, D$_2$O): ∂=1.27 (m, 4H; CH$_2$), 1.56 (m, 2H; CH$_2$), 1.62 (s, 12H; CH$_3$), 1.73 (m, 3H; CH$_3$), 2.17 (m, 2H; CH$_2$), 2.43 (t, $^3$J=7.0 Hz, 2H; CH$_2$), 3.18 (t, 3J=7.0 Hz, 2H; CH$_2$), 4.02 (m, 4H, CH$_2$), 6.32 (t, $^3J$=11.5 Hz, 2H; CH), 7.27 (m, 2H, CH$_{Ar}$), 7.80 (m, 2H, CH$_{Ar}$), 7.85 (s, 2H, CH$_{Ar}$), 8.37 (t, $^3J$=11.5 Hz, 1H, CH); MS: C$_{33}$H$_{44}$N$_{37}$S$_3^+$ ([M]$^+$) m/z calculated: 690.2; found: 690.3.

2.4. Cyanine 5.0-SH

1-Ethyl-2-((1E,3E,5E)-5-(1-(6-((2-mercaptoethyl)amino)-6-oxohexyl)-3,3-dimethylindolin-2-ylidene)penta-1,3-dien-1-yl)-3,3-dimethyl-3H-indol-1-ium

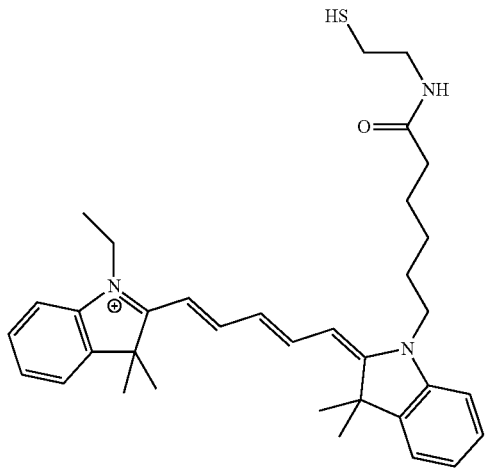 [SMILES: CC[N+]1=C(/C=C/C=C/C=C2/N(CCCCCC(=O)NCCS)c3ccccc3C2(C)C)C(C)(C)c2ccccc21]

Cyanine 5.0 (20.0 mg, 32.7 μmol), TSTU (11.8 mg, 39.3 μmol, 1.2 eq) and DIPEA (6.9 μL, 39.3 μmol, 1.2 eq) were dissolved in 800 μL of anhydrous DMF. The solution was left under agitation at ambient temperature for 10 min, after which 2-aminoethanethiol hydrochloride (7.4 mg, 65.4 μmol, 2.0 eq) and DIPEA (11.4 μL, 65.4 μmol, 2.0 eq) were added. After 1 h at ambient temperature, dithiothreitol (13.1 mg, 85.0 μmol, 2.6 eq) an water (400 μL) were added. The solution was left under agitation for 7 h at ambient temperature, and the DMF afterwards removed under reduced pressure. Purification of the reaction product was carried out by reverse phase semi-preparative HPLC (eluents: H$_2$O 0.1% TFA, ACN 0.1% TFA). Cyanine 5.0-SH was obtained in the form of a blue powder (22.2 mg, purity: 88%, product oxidized to disulfide bridge: 9%)). $^1$H NMR (500 MHz, CD$_3$CN): ∂=1.34 (t, $^3J$=7.0 Hz, 3H; CH$_3$), 1.42 (m, 2H; CH$_2$), 1.60 (m, 1H; SH), 1.63 (m, 2H; CH$_2$), 1.66 (s, 12H; CH$_3$), 1.78 (m, 2H; CH$_2$), 2.13 (t, $^3J$=6.9 Hz, 2H; CH$_2$), 2.54 (m, 2H, CH$_2$), 3.27 (m, 2H, CH$_2$), 4.00 (t, $^3J$=7.5 Hz, 2H; CH$_2$), 4.06 (q, $^3J$=7.0 Hz, 2H, CH$_2$), 6.22 (d, $^3J$=13.7 Hz, 2H; CH), 6.55 (t, $^3J$=12.5 Hz, 1H; CH), 6.74 (s broad, 1H, NH), 7.25 (m, 4H, CH$_{Ar}$), 7.40 (m, 2H, CH$_{Ar}$), 7.48 (m, 2H, CH$_{Ar}$), 8.08 (dd, $^3J$=13.7, 12.5 Hz, 2H, CH); MS: C$_{35}$H$_{46}$N$_3$OS$^+$ ([M]$^+$) m/z calculated: 556.3; found: 556.5.

2.5. Disulfonated Cyanine 5.0-SH

1-Ethyl-2-((1E,3E,5E)-5-(1-(6-((2-mercaptoethyl)amino)-6-oxohexyl)-3,3-dimethyl-5-sulfoindolin-2-ylidene)penta-1,3-dien-1-yl)-3,3-dimethyl-3H-indol-1-ium-5-sulfonate Disulfonated cyanine 5.0 (16.0 mg, 24.4 μmol), TSTU (8.8 mg, 29.2 μmol, 1.2 eq) and DIPEA (15.3 μL, 87.6 μmol, 3.6 eq) were dissolved in 500 μL of DMF. The solution was left under agitation for 5 min, after which cystamine dihydrochloride (8.2 mg, 36.5 μmol, 1.5 eq) dissolved in 500 μL borate buffer (2.5 M, pH 8) and DIPEA (3.2 μL, 18.4 μmol) were added.

After 1 h at ambient temperature, dithiothreitol (6.8 mg, 43.8 μmol, 1.8 eq) was added and the reaction medium left under agitation overnight at ambient temperature. The solvents were removed under reduced pressure and product purification carried out with reverse phase semi-preparative HPLC (eluents: H$_2$O 0.1% TFA, ACN 0.1% TFA). Disulfonated cyanine 5.0-SH was obtained in the form of a blue powder (7.3 mg, 42%). MS: C$_{35}$H$_{46}$N$_3$O$_7$S$_3^+$ ([M]$^+$) m/z calculated: 716.2; found: 716.4.

2.6. (R)-NODAGA-SH (S)-2,2'-(7-(1-carboxy-4-((2-mercaptoethyl)amino)-4-oxobutyl)-1,4,7-triazonane-1,4-diyl)diacetic acid (R)-NODAGA(tBu)$_3$ (159 mg, 292 µmol), TSTU (97.0 mg, 321 µmol, 1.1 eq) and DIPEA (61.0 µL, 350 µmol, 1.2 eq) were dissolved in 2 mL of anhydrous DMF. The solution was left under agitation at ambient temperature for 40 min, and 2-(tritylsulfanyl)ethanamine (102 mg, 321 µmol, 1.1 eq) then added. After 5 h, the DMF was removed under reduced pressure followed by the addition of 10 mL of TFA/DODT/TIS deprotection solution, 90:5:5 (v/v/v). The reaction medium was left under agitation at ambient temperature overnight, the white solid which had formed was removed by filtration and the TFA evaporated under a stream of nitrogen. The product was precipitated in diethyl ether at 4° C. and isolated by centrifugation (4000 rpm, 4° C.). Purification of the reaction product was carried out by reverse phase semi-preparative HPLC (eluents: H$_2$O 0.1% TFA, ACN 0.1% TFA). (R)-NODAGA-SH was obtained in the form of a hygroscopic white powder (89.5 mg, 71%, purity: 95%). $^1$H NMR (300 MHz, D$_2$O): ∂ (ppm)=2.10 (m, 1H; CH$_2$), 2.19 (m, 1H; CH$_2$), 2.51 (t, $^3$J=7.8 Hz, 2H; CH$_2$), 2.68 (t, $^3$J=6.3 Hz, 2H; CH$_2$), 3.11 to 3.22 (m, 4H; CH$_2$), 3.22 to 3.31 (m, 2H; CH$_2$), 3.34 (s, 2H; CH$_2$), 3.40 (t, $^3$J=6.3 Hz, 2H; CH$_2$), 3.70 (dd, 1H; $^3$J=6.0, 7.8 Hz, 1H; CH), 3.98 (s, 4H; CH$_2$); MS: C$_{17}$H$_{31}$N$_4$O$_7$S$^+$ ([M+H]$^+$) m/z calculated: 435.2; found: 435.1.

3. Monofunctionalised Tetrazines of Formula (IV)

3.1. NODAGA-NH-Tz-Cl (IV-1)

(S)-2,2'-(7-(1-carboxy-4-((2-((6-chloro-1,2,4,5-tetrazin-3-yl)amino)ethyl)amino)-4-oxobutyl)-1,4,7-triazonane-1,4-diyl)diacetic acid

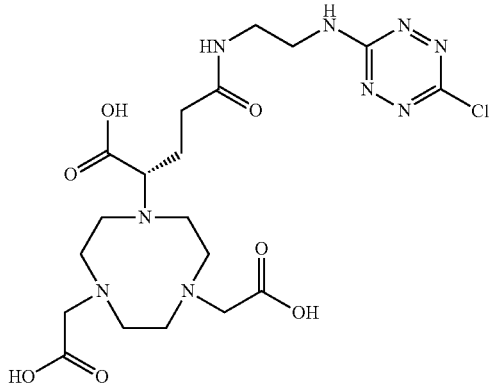 [SMILES: O=C(O)CN1CCN(CC(=O)O)CCN([C@@H](CCC(=O)NCCNc2nnc(Cl)nn2)C(=O)O)CC1]

(R)-NODAGA-NH$_2$ (95.3 mg, 228 µmol) was dissolved in 1 mL of borate buffer (2.5 M, pH 8) and the pH adjusted to pH 8 through the addition of 2.5 M NaOH. Dichloro-s-tetrazine (34.5 mg, 228 µmol, 1.0 eq) in 300 µL ACN was added. After being left under agitation at ambient temperature for 2 h. the solvents were removed under reduced pressure.

Purification of the reaction product was carried out with reverse phase semi-preparative HLPC (eluents: H$_2$O 0.1% formic acid, ACN 0.1% formic acid). NODAGA-NH-Tz-Cl was obtained in the form of an orange powder (43.8 mg, 36%). $^1$H NMR (500 MHz, D$_2$O): ∂=1.20 (m, 1H; CH$_2$), 2.05 (m, 1H; CH$_2$), 2.43 (t, $^3$J=7.5 Hz, 2H; CH$_2$), 3.01 to 3.15 (m, 4H; CH$_2$), 3.22 (m, 2H; CH$_2$), 3.29 (s, 4H; CH$_2$), 3.46 to 3.59 (m, 3H; CH, CH$_2$), 3.71 (m, 2H; 2H; CH$_2$), 3.58 (s, 4H; CH$_2$); MS: C$_{19}$H$_{31}$ClN$_9$O$_7$$^+$ ([M+H]$^+$) m/z calculated: 532.2; found: 532.1.

3.2. DOTAGA-NH-Tz-Cl (IV-2)

2,2',2''-(10-(1-carboxy-4-((2-((6-chloro-1,2,4,5-tetrazin-3-yl)amino)ethyl)amino)-4-oxobutyl)-1,4,7,10-tetraazacyclododecane-1,4,7-triyl)triacetic acid

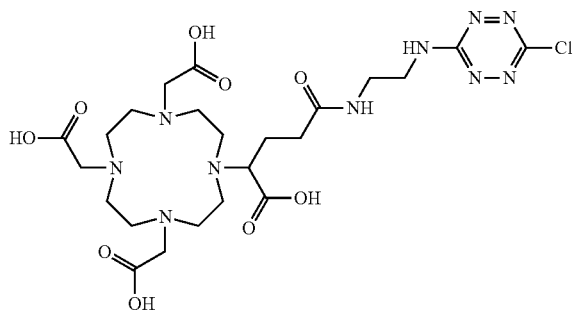 [SMILES: O=C(O)CN1CCN(CC(=O)O)CCN(C(CCC(=O)NCCNc2nnc(Cl)nn2)C(=O)O)CCN(CC(=O)O)CC1]

DOTAGA-NH$_2$ (243 mg, 443 µmol) was dissolved in 7 mL of borate buffer (2.5 M, pH 8) and the pH was adjusted to pH 8 through the addition of 2.5 M NaOH. Dichloro-s-tetrazine (68 mg, 443 µmol, 1.0 eq) in 2 mL of ACN was added.

After an agitation time of 2 h at ambient temperature, the solvents were removed under reduced pressure. Purification of the reaction product was carried out by reverse phase semi-preparative HPLC (eluents: H$_2$O 0.1% TFA, ACN 0.1% TFA). DOTAGA-NH-Tz-Cl was obtained in the form of an orange powder (154 mg, purity: 99%). $^1$H NMR (500 MHz, D$_2$O): ∂=1.20 (m, 1H; CH$_2$), 2.05 (m, 1H; CH$_2$), 2.43 (t, $^3$J=7.5 Hz, 2H; CH$_2$), 3.01 to 3.15 (m, 4H; CH$_2$), 3.22 (m, 2H; CH$_2$), 3.29 (s, 4H; CH$_2$), 3.46 to 3.59 (m, 3H; CH, CH$_2$), 3.71 (m, 2H; 2H; CH$_2$), 3.58 (s, 4H; CH$_2$); MS: C$_{19}$H$_{31}$ClN$_9$$_7$$^+$ ([M+H]$^+$) m/z calculated: 532.2; found: 532.1.

3.3. (R)-NODAGA-S-Tz-Cl (IV-3)

(S)-2,2'-(7-(1-carboxy-4-((2-((6-chloro-1,2,4,5-tetrazin-3-yl)thio)ethyl)amino)-4-oxobutyl)-1,4,7-triazonane-1,4-diyl)diacetic acid

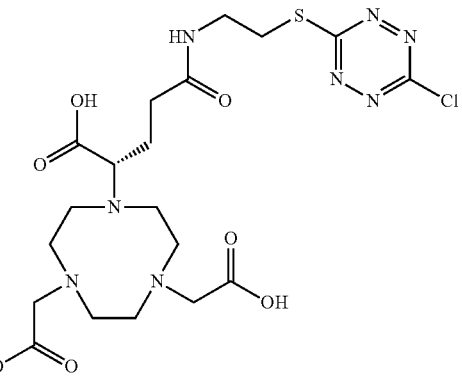

(R)-NODAGA-SH (40 mg, 92 µmol) and dichloro-s-tetrazine (41.7 mg, 276 µmol, 3 eq.) were dissolved in 3 mL of anhydrous DMF. After agitation for 10 min at ambient temperature, the DMF was removed under reduced pressure. Purification of the reaction product was carried out by reverse phase semi-preparative HPLC (eluents: $H_2O$ 0.1% trifluoroacetic acid, ACN 0.1% trifluoroacetic acid). (R)-NODAGA-S-Tz-Cl was obtained in the form of an orange powder (46 mg, 91%, purity: 96%). $^1$H NMR (500 MHz, $D_2O$): ∂=2.04 (m, 1H; $CH_2$), 2.11 (m, 1H; $CH_2$), 2.46 (m, 2H; $CH_2$), 3.08 to 3.11 (m, 4H; $CH_2$), 3.23 (m, 4H; $CH_2$), 3.29 (s, 4H, $CH_2$), 3.55 (t, $^3J$=7.1 Hz, 1H; CH), 3.58 (m, 2H; $CH_2$), 3.67 (m, 2H; $CH_2$), 3.826 (s, 2H; $CH_2$), 3.831 (s, 2H; $CH_2$); MS: $C_{19}H_{30}ClN_8O_7S^+$ ([M+H]$^+$) m/z calculated: 549.2; found: 548.9.

3.4. BODIPY-S-Tz-Cl (IV-4)

10-(4-((2-((6-chloro-1,2,4,5-tetrazin-3-yl)thio)ethyl)carbamoyl)phenyl)-2,8-diethyl-5,5-difluoro-1,3,7,9-tetramethyl-5H-dipyrrolo[1,2-c:2'1'-f][1,3,2]diazaborinin-4-ium-5-uide

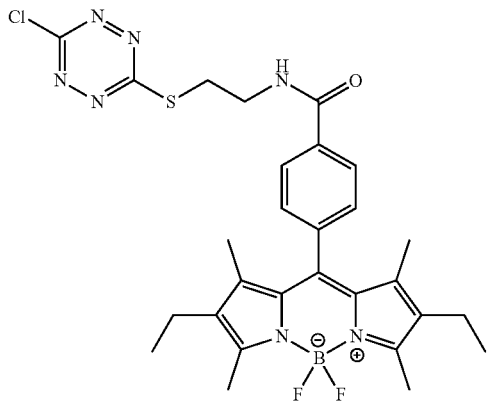 [SMILES: CCC1=C(C)C2=C(c3ccc(C(=O)NCCSc4nnc(Cl)nn4)cc3)c3c(C)c(CC)c(C)n3[B-](F)(F)[N+]2=C1C]

BODIPY-SH (29.1 mg, 60.2 µmol) and dichloro-s-tetrazine (10.6 mg, 70.2 µmol, 1.2 eq) were dissolved in 1.5 mL of DMF/ACN mixture 0.6:0.4 (v/v) and DIPEA (12.5 µL, 72.2 µmol, 1.2 eq) was added to the reaction medium.

After agitation for for 1 h at ambient temperature, the solvents were removed under reduced pressure. Purification of the reaction product was carried out by reverse phase semi-preparative HPLC (eluents: $H_2O$ 0.1% formic acid, ACN 0.1% formic acid). BODIPY-S-Tz-Cl was obtained in the form of a red powder (24.1 mg, purity: 90%, product reduced to dihydrotetrazine: 10%). $^1$H NMR (300 MHz, $CDCl_3$): ∂=0.96 (t, $^3J$=7.5 Hz, 6H; $CH_3$), 1.23 (s, 6H; $CH_3$), 2.28 (q, $^3J$=7.5 Hz, 4H; $CH_2$), 2.51 (s, 6H; $CH_3$), 3.65 (t, $^3J$=6.3 Hz, 2H; $CH_2$), 3.92 (dt, $^3J$=5.7, 6.3 Hz, 2H; $CH_2$), 6.71 (t, $^3J$=5.7 Hz, 1H; NH), 7.39 (d, $^3J$=8.2 Hz, 2H; $CH_{Ar}$), 8.18 (d, $^3J$=8.2 Hz, 2H; $CH_{Ar}$); HRMS: $C_{28}H_{31}BClFN_7OS^+$ ([M−F]$^+$) m/z calculated: 578.20709; found: 578.20828.

3.5. Rhodamine B-S-Tz-Cl (IV-5)

N-(9-(2-((2-((6-chloro-1,2,4,5-tetrazin-3-yl)thio)ethyl)carbamoyl)phenyl)-6-(diethylamino)-3H-xanthen-3-ylidene)-N-ethylethanaminium

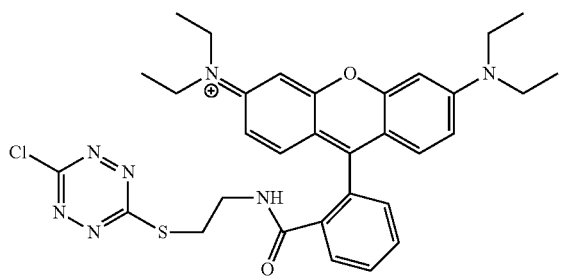 [SMILES: CCN(CC)c1ccc2c(-c3ccccc3C(=O)NCCSc3nnc(Cl)nn3)c3ccc(=[N+](CC)CC)cc-3oc2c1]

Rhodamine B-SH (200 mg, 399 µmol) and dichloro-s-tetrazine (60.3 mg, 399 µmol, 1.0 eq.) were dissolved in 2 mL of ACN, and DIPEA (69.5 µL, 399 µmol, 1.0 eq) was added to the reaction medium. The solution was left under agitation for 5 h at ambient temperature and the solvent afterwards removed under reduced pressure. Purification of the reaction product was carried out by reverse phase semi-preparative HPLC (eluents: $H_2O$ 0.1% formic acid, ACN 0.1% formic acid). Rhodamine B-S-Tz-Cl was obtained in the form of a pink powder (47.8 mg, 19%). $^1$H NMR (300 MHz, $CDCl_3$): equilibrium between the cyclic and non-cyclic forms of rhodamine; HRMS: $C_{32}H_{35}ClN_7O_2S^+$ ([M]$^+$) m/z calculated: 616.22560; found: 616.22622; $C_{32}H_{34}ClN_7NaO_2S^+$ (cyclic form) ([M−H+Na]$^+$) m/z calculated: 638.20754; found: 638.20749.

3.6. Disulfonated Cyanine 3.0-S-Tz-Cl (IV-6)

2-((1E,3E)-3-(1-(6-((2-((6-chloro-1,2,4,5-tetrazin-3-yl)thio)ethyl)amino)-6-oxohexyl)-3,3-dimethyl-5-sulfoindolin-2-ylidene)prop-1-en-1-yl)-1-ethyl-3,3-dimethyl-3H-indol-1-ium-5-sulfonate

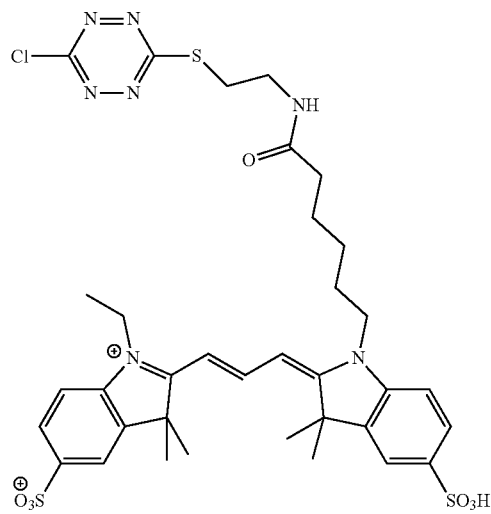

Disulfonated cyanine 3.0-SH (15.8 mg, 22.9 µmol) and dichloro-s-tetrazine (4.3 mg, 28.5 µmol, 1.2 eq) were dissolved in 1 mL of anhydrous DMF, and DIPEA (5.5 µL, 31.8 µmol, 1.4 eq) was added to the reaction medium under agitation at ambient temperature. After 1 h, the reaction was complete and the solvent removed under reduced pressure. The reaction product was purified by reverse phase semi-preparative HPLC (eluents: H$_2$O 0.1% formic acid, ACN 0.1% formic acid). Disulfonated cyanine 3.0-S-Tz-Cl was obtained in the form of a pink powder (6.0 mg). HRMS (negative mode): C$_{35}$H$_{41}$ClN$_7$O$_7$S$_3^-$ ([M−H]$^-$) m/z calculated: 802.19236; found: 802.18923.

4. Bifunctionalised Tetrazines of Formula (IIa)

4.1. DOTAGA-NH-Tz-S-Rhodamine B (II-1)

N-(9-(2-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)carbamoyl)phenyl)-6-(diethylamino)-3H-xanthen-3-ylidene)-N-ethylethanaminium 2,2,2-trifluoroacetate

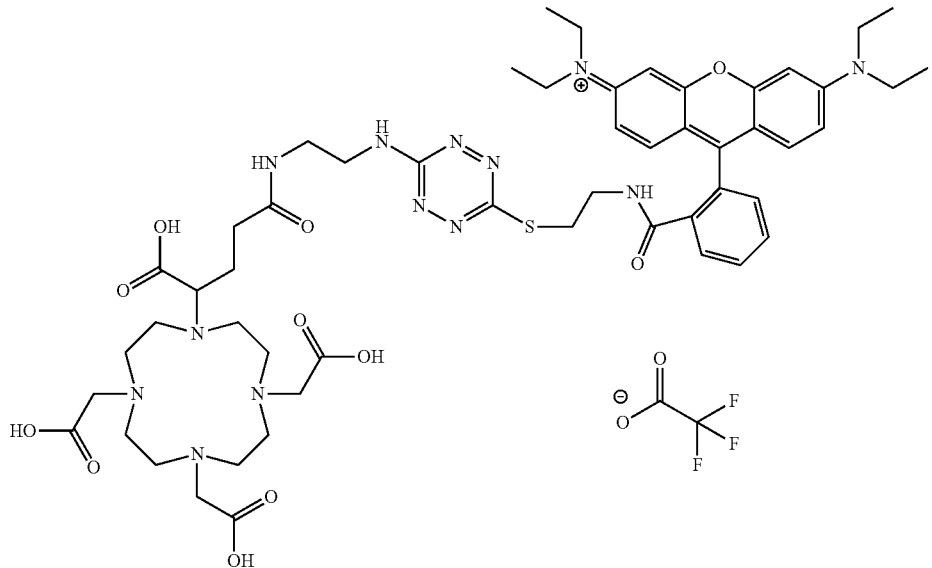 [SMILES: CCN(CC)c1ccc2c(-c3ccccc3C(=O)NCCSc3nnc(NCCNC(=O)CCC(C(=O)O)N4CCN(CC(=O)O)CCN(CC(=O)O)CCN(CC(=O)O)CC4)nn3)c3ccc(=[N+](CC)CC)cc-3oc2c1 ; O=C([O-])C(F)(F)F]

Rhodamine B-SH (39.7 mg, 79.0 µmol) and DOTAGA-NH-Tz-Cl (50.0 mg, 79.0 µmol, 1.0 eq.) were dissolved in 1 mL of anhydrous DMF, and DIPEA (65.7 µL, 395 µmol, 5.0 eq.) was added to the reaction medium. The solution was left under agitation at 75° C. for 3 h, and the solvent afterwards removed under reduced pressure. Purification of the reaction product was carried out by reverse phase semi-preparative HPLC (eluents: H$_2$O 0.1% formic acid, ACN 0.1% formic acid). DOTAGA-NH-Tz-S-Rhodamine B was obtained in the form of a red oil (37.0 mg, 43%) $^1$H NMR (500 MHz, D$_2$O) ∂: 1.13 (m, 12H; CH$_3$), 2.01 (m, 2H; CH$_2$), 2.56 (m, 2H; CH$_2$), 2.96 (m, 2H; CH$_2$), 3.00 to 3.48 (m, 12H; CH$_2$), 3.48 to 3.63 (m, 8H; CH$_2$), 3.69 (m, 10H; CH$_2$), 3.74 to 4.37 (m, 6H; CH$_2$), 3.99 (m, 1H; CH), 7.11 (m, 2H; CH$_{Ar}$), 7.24 (m, 3H; CH$_{Ar}$), 7.63 (m, 2H; CH$_{Ar}$), 7.72 (m, 2H; CH$_{Ar}$), 8.02 (m, 1H; CH$_{Ar}$); HRMS: C$_{53}$H$_{72}$N$_{13}$O$_{11}$S$^+$ ([M]$^+$) m/z calculated: 1098.51895; found: 1098.52126; C$_{53}$H$_{71}$N$_{13}$NaO$_{11}$S$^+$ ([M−H+Na]$^+$) m/z calculated: 1120.50089; found: 1120.50291; C$_{53}$H$_{70}$KN$_{13}$NaO$_{11}$S$^+$ ([M−2H+Na+K]$^+$) m/z calculated: 1158.45677; found: 1158.4541.

4.2. DOTAGA-NH-Tz-S-BODIPY (II-2)

10-(4-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)carbamoyl)phenyl)-2,8-diethyl-5,5-difluoro-1,3,7,9-tetramethyl-5H-dipyrrolo[1,2-c:2,1'-f][1,3,2]diazaborinin-4-ium-5-uide

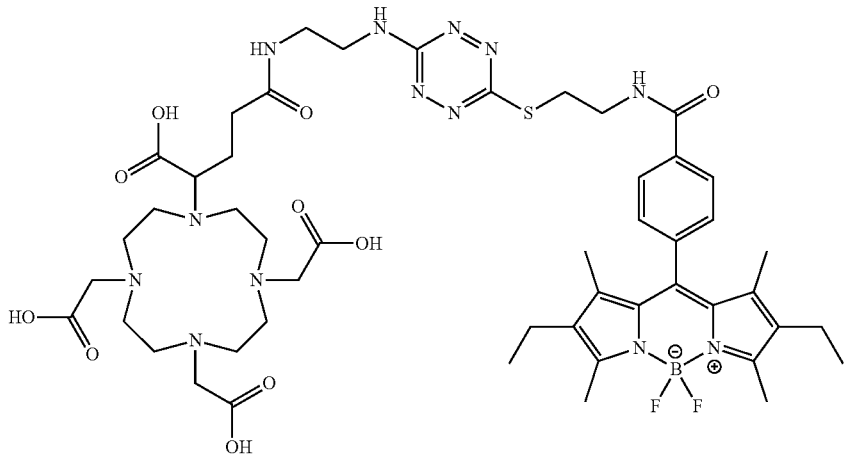 [SMILES: CCC1=C(C)C2=C(c3ccc(C(=O)NCCSc4nnc(NCCNC(=O)CCC(C(=O)O)N5CCN(CC(=O)O)CCN(CC(=O)O)CCN(CC(=O)O)CC5)nn4)cc3)c3c(C)c(CC)c(C)n3[B-](F)(F)[N+]2=C1C]

BODIPY-SH (11.7 mg, 24.2 μmol) and DOTAGA-NH-Tz-Cl (15.3 mg, 24.2 μmol, 1.0 eq. were dissolved in 1 mL of anhydrous DMF, and DIPEA (22.8 μL, 121.0 μmol, 5.0 eq.) was added to the reaction medium. The solution was left under agitation at 75° C. for 1 h 30, and the solvent afterwards removed under reduced pressure. Purification of the reaction product was carried out by reverse phase semi-preparative HPLC (eluents: $H_2O$ 0.1% formic acid, ACN 0.1% formic acid). DOTAGA-NH-Tz-S-BODIPY was obtained in the form of a red powder (18.0 mg, 69%, purity: 95%). $^1$H NMR (500 MHz, MeOD) ∂: 0.99 (m, 6H; $CH_3$), 1.32 (s, 6H; $CH_3$), 2.35 (m, 4H; $CH_2$), 2.48 (s, 6H; $CH_3$), 3.01 to 4.13 (m, 27H; $CH_{2, macrocycle}$), 3.52 (m, 2H; $CH_2$), 3.80 (m, 2H; $CH_2$), 7.46 (m, 2H; $CH_{Ar}$), 8.01 (m, 2H; $CH_{Ar}$);

HRMS: $C_{49}H_{69}BF_2N_{13}O_{10}S^+$ ([M+H]$^+$) m/z calculated: 1080.50667; found: 1080.50639; $C_{49}H_{67}BF_2N_{13}NaO_{10}S^+$ ([M+Na]$^+$) m/z calculated: 1102.48861; found: 1102.48834; $C_{49}H_{67}BF_2N_{13}Na_2O_{10}S^+$ ([M–H+2Na]$^+$) m/z calculated: 1124.47056; found: 1124.46975.

4.3. DOTAGA-NH-Tz-S-cyanine 5.0 (II-3)

2-((1E,3E,5E)-5-(1-(6-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)amino)-6-oxohexyl)-3,3-dimethylindolin-2-ylidene)penta-1,3-dien-1-yl)-1-ethyl-3,3-dimethyl-3H-indol-1-ium

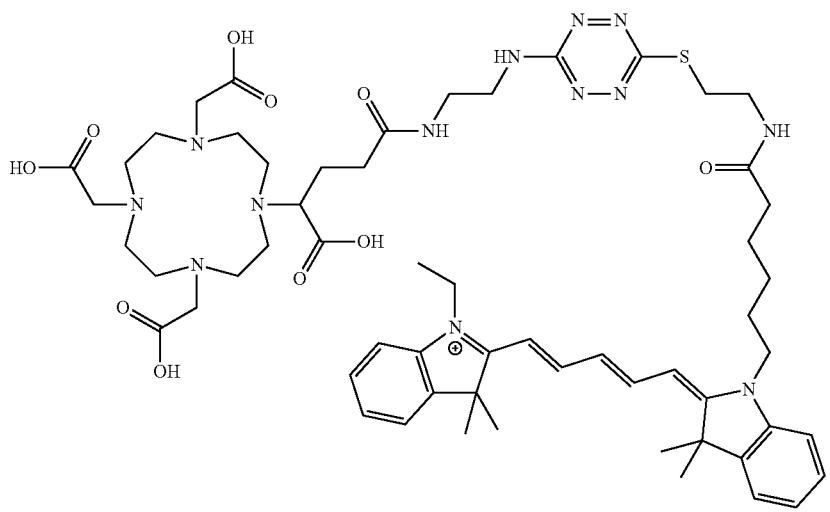 [SMILES: CC[N+]1=C(/C=C/C=C/C=C2/N(CCCCCC(=O)NCCSc3nnc(NCCNC(=O)CCC(C(=O)O)N4CCN(CC(=O)O)CCN(CC(=O)O)CCN(CC(=O)O)CC4)nn3)c3ccccc3C2(C)C)C(C)(C)c2ccccc21]

Cyanine 5.0-SH (14.9 mg, 26.8 μmol) and DOTAGA-NH-Tz-Cl (19.5 mg, 30.8 μmol, 1.1 eq.) were dissolved in 1 mL of anhydrous DMF, and DIPEA (28.0 μL, 149.5 μmol, 5.6 eq.) was added to the reaction medium. The solution was left under agitation at 75° C. for 1 h, and the solvent afterwards removed under reduced pressure. Purification of the reaction product was carried out by reverse phase semi-preparative HPLC (eluents: H$_2$O 0.1% formic acid, ACN 0.1% formic acid). DOTAGA-NH-Tz-S-cyanine 5.0 was obtained in the form of a blue powder (15.1 mg, 49%). $^1$H NMR (500 MHz, CD$_3$CN): ∂=1.33 (t, $^3$J=7.0 Hz, 3H; CH$_3$), 1.42 (m, 2H; CH$_2$), 1.61 (m, 2H; CH$_2$), 1.67 (s, 12H; CH$_3$), 1.76 (m, 2H; CH$_2$), 2.12 (t, 2H; CH$_2$), 2.76 to 3.97 (m, 35H; macrocycle+CH$_2$), 4.00 (t, 2H; CH$_2$), 4.06 (q, $^3$J=7.0 Hz, 2H, CH$_2$), 6.21 (d, $^3$J=13.0 Hz, 2H; CH), 6.53 (t, $^3$J=13.0 Hz, 1H; CH), 7.25 (m, 4H, CH$_{Ar}$), 7.40 (m, 2H, CH$_{Ar}$), 7.47 (m, 2H, CH$_{Ar}$), 8.07 (dd, 2H, CH); HRMS: C$_{58}$H$_{82}$N$_{13}$O$_{10}$S$^+$ ([M]$^+$) m/z calculated: 1152.60228; found: 1152.60445; C$_{58}$H$_{82}$N$_{13}$NaO$_{10}$S$^{2+}$ ([M+Na]$^{2+}$) m/z calculated: 587.79575; found: 587.79558.

4.4. DOTAGA-NH-Tz-S-disulfonate Cyanine 5.0 (II-4)

2-((1E,3E,5E)-5-(1-(6-((2-((6-((2-(4-carboxy-4-(4,7,10-tris(carboxymethyl)-1,4,7,10-tetraazacyclododecan-1-yl)butanamido)ethyl)amino)-1,2,4,5-tetrazin-3-yl)thio)ethyl)amino)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate

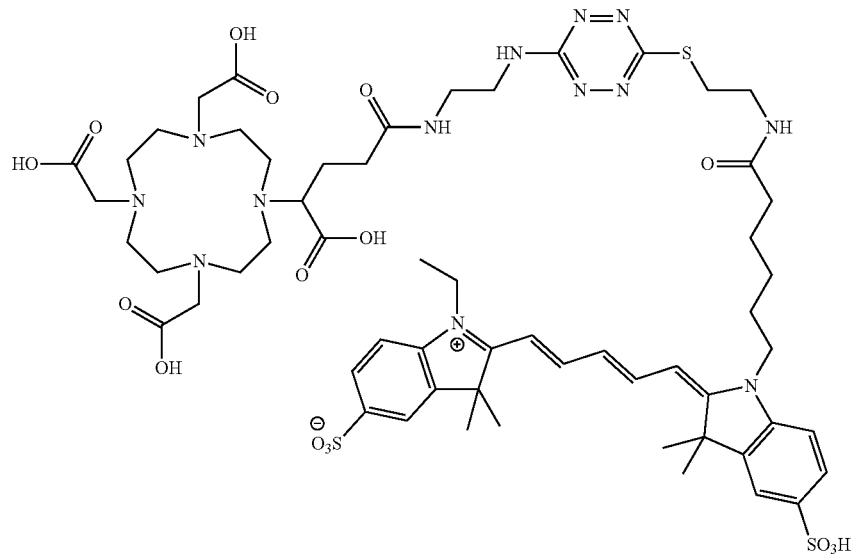

Disulfonated cyanine 5.0 —SH (5.4 mg, 7.54 μmol) and DOTAGA-NH-Tz-Cl (5.7 mg, 9.05 μmol, 1.2 eq.) were dissolved in 800 μL of anhydrous DMF, and DIPEA (8.47 μL, 45.25 μmol, 6.0 eq.) was added to the reaction medium. The solution was left under agitation at 75° C. for 5 h, and the solvent afterwards removed under reduced pressure. Purification of the reaction product was carried out by reverse phase semi-preparative HPLC (eluents: H$_2$O 0.1% formic acid, ACN 0.1% formic acid). DOTAGA-NH-Tz-S-disulfonated cyanine 5.0 was obtained in the form of a blue powder (3.75 mg). $^1$H NMR (500 MHz, D$_2$O) ∂: 1.31 (m, 5H; CH$_2$+CH$_3$), 1.59 (m, 2H; CH$_2$), 1.61 (s, 6H; CH$_3$), 1.67 (s, 6H; CH$_3$), 1.81 (m, 2H; CH$_2$), 1.88 (m, 2H; CH$_2$), 2.20 (t, 2H; CH$_2$), 2.44 (m, 2H; CH$_2$), 2.97 to 3.63 (m, 26H; 2 CH$_2$+11 CH$_{2, macrocycle}$), 3.82 (m, 5H; 2 CH$_2$+CH), 4.07 (m, 4H; CH$_2$), 6.15 (d, 1H; CH), 6.23 (d, 1H; CH), 6.48 (t, 1H; CH), 7.33 (d, 2H; CH$_{Ar}$), 7.79 à 7.88 (m, 4H; CH$_{Ar}$), 7.96 (m 1H; CH), 8.01 (m 1H; CH);

4.5. (R)-NODAGA-NH-Tz-S-BODIPY (II-5)

(S)-10-(4-((2-(((6-((2-(4-(4,7-bis(carboxymethyl)-1,4,7-triazonan-1-yl)-4-carboxybutanamido)ethyl)amino)-1,2,4,5-tetrazin-3-yl)thio)ethyl)carbamoyl)phenyl)-2,8-diethyl-5,5-difluoro-1,3,7,9-tetramethyl-5H-dipyrrolo[1,2-c:2,1'-f][1,3,2]diazaborinin-4-ium-5-uide

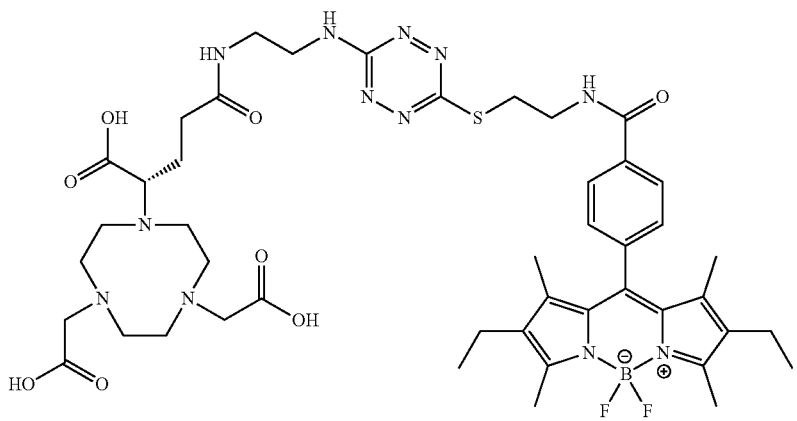 [SMILES: CCC1=C(C)C2=C(c3ccc(C(=O)NCCSc4nnc(NCCNC(=O)CC[C@@H](C(=O)O)N5CCN(CC(=O)O)CCN(CC(=O)O)CC5)nn4)cc3)c3c(C)c(CC)c(C)n3[B-](F)(F)[N+]2=C1C]

BODIPY-SH (17.0 mg, 40.1 μmol) and (R)-NODAGA-NH-Tz-Cl (27.4 mg, 51.5 μmol, 1.3 eq.) were dissolved in 1 mL of anhydrous DMF, and DIPEA (48.3 μL, 275.5 μmol, 5.0 eq.) was added to the reaction medium. The solution was left under agitation at 75° C. for 1 h, and the solvent afterwards removed under reduced pressure. Purification of the reaction product was carried out by reverse phase semi-preparative HPLC (eluents: H$_2$O 0.1% formic acid, ACN 0.1% formic acid). (R)-NODAGA-NH-Tz-S-BODIPY was obtained in the form of a red powder (8.1 mg). HRMS: C$_{45}$H$_{62}$BF$_2$N$_{12}$O$_8$S$^+$ ([M+H]$^+$) m/z calculated: 979.45899; found: 979.45948; C$_{45}$H$_{61}$BF$_2$N$_{12}$NaO$_8$S$^+$ ([M+Na]$^+$) m/z calculated: 1001.44094; found: 1001.44055.

5. Bifunctionalised Tetrazines of Formula (IIb)

5.1. (R)-NODAGA-S-Tz-S-peptide (II-6)

2,2'-(7-((S)-4-((2-((6-((((2S,5S,11S,17S,20S,23S,26R)-17-((1H-indol-3-yl)methyl)-26-acetamido-1-amino-23-(4-aminobutyl)-5-(carboxymethyl)-11-(3-guanidinopropyl)-20-(4-hydroxybenzyl)-2-(hydroxymethyl)-1,4,7,10,13,16,19,22,25-nonaoxo-3,6,9,12,15,18,21,24-octaazaheptacosan-27-yl)thio)-1,2,4,5-tetrazin-3-yl)thio)ethyl)amino)-1-carboxy-4-oxobutyl)-1,4,7-triazonane-1,4-diyl)diacetic acid

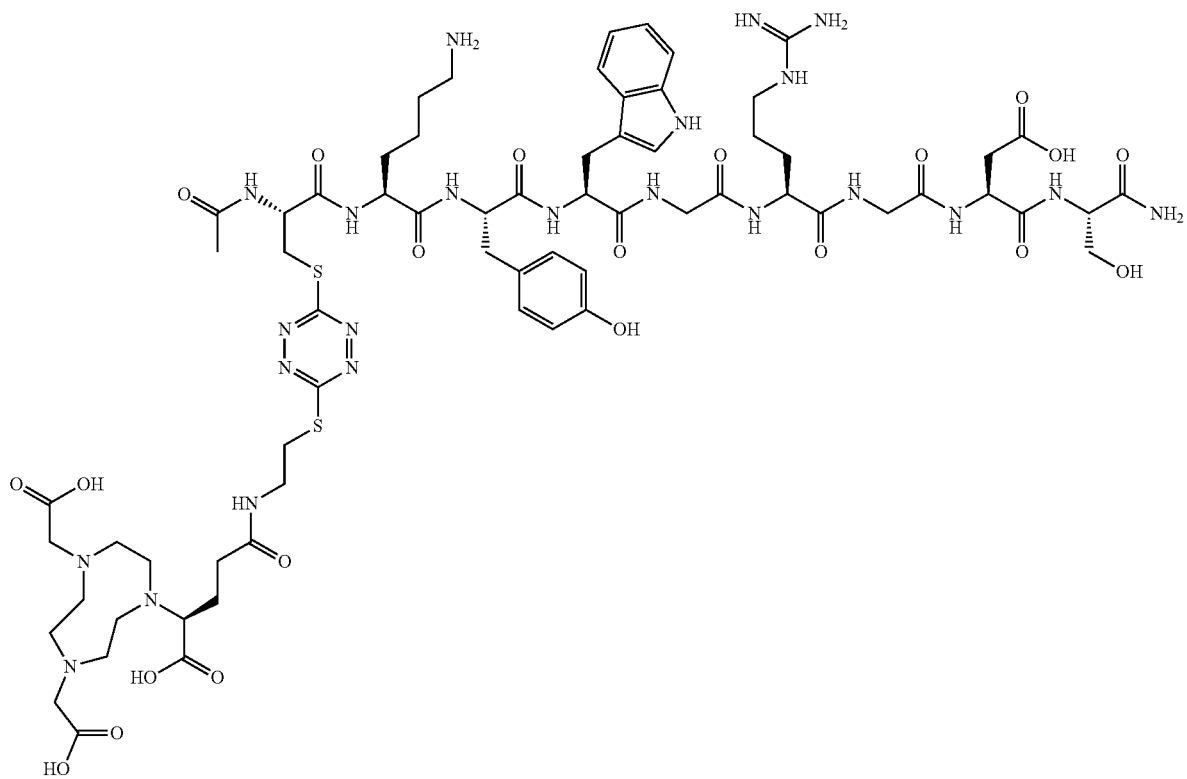 [SMILES: CC(=O)N[C@@H](CSc1nnc(SCCNC(=O)CC[C@@H](C(=O)O)N2CCN(CC(=O)O)CCN(CC(=O)O)CC2)nn1)C(=O)N[C@@H](CCCCN)C(=O)N[C@@H](Cc1ccc(O)cc1)C(=O)N[C@@H](Cc1c[nH]c2ccccc12)C(=O)NCC(=O)N[C@@H](CCCNC(=N)N)C(=O)NCC(=O)N[C@@H](CC(=O)O)C(=O)N[C@@H](CO)C(N)=O]

(R)-NODAGA-S-Tz-Cl (8.5 mg, 15.5 µmol) and peptide Ac-CKYWGRGDS-NH$_2$, 2 TFA (25 mg, 18.7 µmol, 1.2 eq.) were dissolved in 600 µL of ultrapure water. The solution was left under agitation at ambient temperature, protected from light, for 30 min. Purification of the reaction product was carried out by reverse phase semi-preparative HPLC (eluents: H$_2$O 0.1% formic acid, ACN 0.1% formic acid). The product (R)-NODAGA-S-Tz-S-peptide, which can also be written Ac-C(Tz-S-NODAGA)KYWGRGDS-NH$_2$, was obtained in the form of an orange powder (5.8 mg, 55%, purity: 82%). HRMS: $C_{67}H_{98}N_{23}O_{21}S_2^+$ ([M+H]$^+$) m/z calculated: 1624.67; found: 1624.57; $C_{67}H_{97}N_{23}NaO_{21}S_2^+$ ([M+Na]$^+$) m/z calculated: 1646.66; found: 1646.49.

5.2. BSA-S-tetrazine-S-NODAGA (II-7)

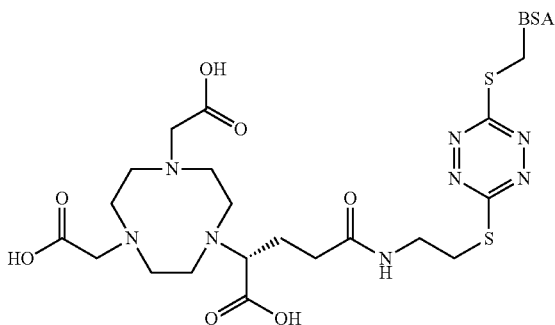

Bovine Serum Albumin (BSA) was incubated with (R)-chlorotetrazine-NODAGA (10 equiv.) for 1 hour at ambient temperature (pH=5.15). After purification by ultracentrifugation, the BSA-S-tetrazine-S—(R)-NODAGA (II-7) compound was obtained. LC-HRMS after deconvolution of the mass spectrum: 67004 (corresponds to compound I-3) and 66430 (corresponds to the protein residue without probe).

5.3. Fab'-S-tetrazine-S-DOTAGA (II-8)

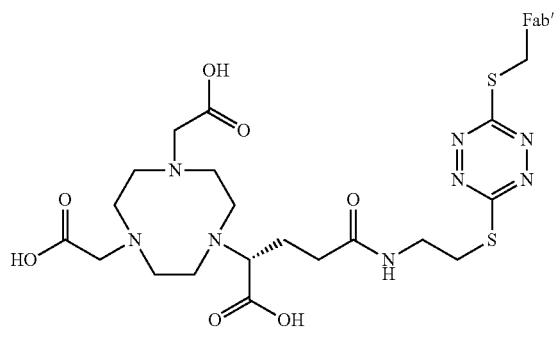

The Fab' fragment was incubated with (R)-chlorotetrazine-NODAGA (50 equiv.) for 30 minutes at 37° C. (pH=7.3). LC-HRMS of the reaction after deconvolution of the mass spectrum: 49687 (corresponds to compound I-3) and 48660 (corresponds to the Fab' residue without probe). The compound was not purified before being used for formation of the compound (disulfonated cyanine 5.0-BCN-pyridazine, S—(R)-NODAGA)$_2$, S-Fab' (I-4).

5.4. Reactivity Selectivity of (R)-NODAGA-S-Tz-Cl for Thiols Versus the Amines of a Peptide The chemoselectivity of the reaction of the chlorotetrazines monosubstituted by a nucleophile of thiol type, with respect to the nucleophiles present on the proteins, was assessed using two model peptides: Ac-CKYWGRGDS-NH$_2$ and Ac-MKYWGRGDS-NH$_2$. These peptides contain the most usual amino acids having nucleophilic side chains such as lysine (amine), serine (alcohol) and tyrosine (phenol). They differ through the presence of a cysteine (thiol) in one thereof, which is substituted by a methionine (thioether) in the other.

The peptides (20 μM), in solution in a phosphate buffer (0.01 M; different pHs), were incubated in the presence of 2.5 equivalents of (R)-NODAGA-S-Tz-Cl at 25° C. The conversion rate to product, resulting from substitution of the chlorine of (R)-NODAGA-S-Tz-Cl by the peptides, was determined by LC-MS at 214 nm. The results are given in the table below.

Conversion rate of the peptides in the presence of 2.5 equiv. of (R)-NODAGA-S-Tz-Cl at different pHs. (quant.: quantitative; <1%: detection limit of the method used).

| | | pH | | |
|---|---|---|---|---|
| | | 5.97 | 6.29 | 7.13 |
| Ac-CKYWGRGDS-NH$_2$ | 3.5 min | 96% | 96% | quant. |
| | 30 min | 97% | quant. | quant. |

| | | pH | | |
|---|---|---|---|---|
| | | 5.97 | 6.29 | 7.13 |
| Ac-MKYWGRGDS-NH$_2$ | 3.5 min | — | <1% | <1% |
| | 30 min | — | <1% | <1% |

These results show that the chlorotetrazines mono-substituted by a nucleophile of thiol type selectively react with the nucleophiles of thiol type carried by the Ac-CKYWGRGDS-NH$_2$ peptide, within a few minutes and under mild conditions (buffered aqueous solution, 25° C., neutral pH). In the absence of cysteine, no reaction was observed.

6. Intermediates of Formula (III)

6.1. Cyanine 5.0-BCN 2-((1E,3E,5E)-5-(1-(6-((2-((((1R,8S,9s)-bicyclo[6.1.0]non-4-yn-9-ylmethoxy)carbonyl)amino)ethyl)amino)-6-oxohexyl)-3,3-dimethylindolin-2-ylidene)penta-1,3-dien-1-yl)-1-ethyl-3,3-dimethyl-3H-indol-1-ium 2,2,2-trifluoroacetate

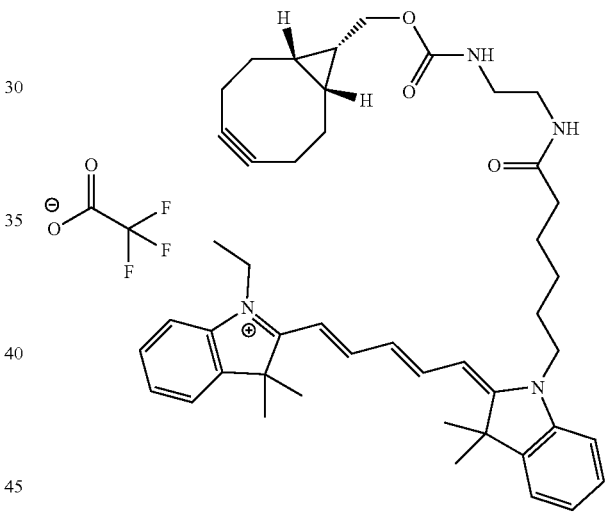

Cyanine 5.0-NH$_2$ (25.7 mg, 33.5 μmol) and bicyclononyne-N-hydroxysuccinnimide (16.3 mg, 55.8 μmol, 1.7 eq.) were dissolved in 1 mL of anhydrous DMF, and DIPEA (8.41 μL, 48.6 μmol, 1.5 eq.) was added to the reaction medium. The solution was left under agitation 40 min at ambient temperature, and the solvent afterwards removed under reduced pressure. The reaction product was purified by reverse phase semi-preparative HPLC (eluents: H$_2$O 0.1% TFA, ACN 0.1% TFA). Cyanine 5.0-BCN, TFA was obtained in the form of a blue powder (11.5 mg, 41%, TFA salt, purity: 90%). $^1$H NMR (500 MHz, CDCl$_3$): $\partial$=0.86 (m, 2H; CH), 1.31 (m, 1H; CH), 1.39 (t, $^3J$=7.5 Hz, 3H; CH$_3$), 1.47 (m, 2H; CH$_2$), 1.53 (m, 2H; CH$_2$), 1.66 (s, 6H; CH$_3$), 1.67 (s, 6H; CH$_3$), 1.71 (m 2H; CH$_2$), 1.79 (m 2H; CH$_2$), 2.08 to 2.27 (m, 6H; CH$_2$), 2.30 (t, $^3J$=7.3 Hz, 2H; CH$_2$), 3.31 (m, 2H; CH$_2$), 3.54 (m, 2H; CH$_2$), 3.99 (t, $^3J$=7.6 Hz, 2H; CH$_2$), 4.04 (q, $^3J$=7.2 Hz, 2H; CH$_2$), 4.07 (d, $^3J$=8.4 Hz, 2H; CH$_2$), 6.04 to 6.22 (m, 1H; OCONH), 6.17 (d, $^3J$=13.5 Hz, 1H; CH), 6.26 (d, $^3J$=13.5 Hz, 1H; CH), 6.66 (t, $^3J$=12.5 Hz, 1H; CH), 7.05 (d, $^3J$=7.9 Hz, 1H; CH$_{Ar}$), 7.10 (d, $^3J$=8.0 Hz, 1H; CH$_{Ar}$), 7.22 (m, 2H; CH$_{Ar}$), 7.35 (m, 4H; CH$_{Ar}$), 7.78 (dd, $^3J$=12.0, 13.5 Hz, 1H; CH), 7.79 (dd, $^3J$=12.0, 13.5

Hz, 1H; CH), 8.26 (m, 1H; CONH); HRMS: $C_{46}H_{59}N_4O_3^+$ ([M]$^+$) m/z calculated: 715.45817; found: 715.45752.

6.2. Trastuzumab-BCN

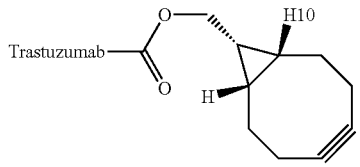

26.7 μL stock solution of 2 mM BCN-NHS in DMSO (53.3 nmol, 4.0 eq.) were added to the trastuzumab antibody (Herceptin; Roche, U.K.) (2 mg, 13.3 nmol) in solution in a bicarbonate buffer (0.2 M, pH 8.5) in the presence of 10% (v/v) DMSO (trastuzumab concentration: 2 mg/mL). The solution was left under agitation in a thermomixer (800 rpm, 25° C.) for 2 h. Excess BCN was removed by ultrafiltration on Amicon Ultra Ultracel-30 kDa (Merck Millipore). At the ultrafiltration step, the product was concentrated and the bicarbonate buffer exchanged for PBS buffer (0.01 M, pH 7.4). Trastuzumab-BCN was isolated in solution in 51 μL PBS at a concentration of 35.5 mg/mL (1.81 mg, 12.1 nmol, labelling yield: 91%). The BCN/antibody ratio was 3.3 (determined by MALDI/TOF mass spectrometry).

7. Trifunctionalised Platforms of Formula (I)

7.1. Trastuzumab-BCN-Pyridazine, NH-DOTAGA, Disulfonated S-Cyanine 5.0 (I-1)

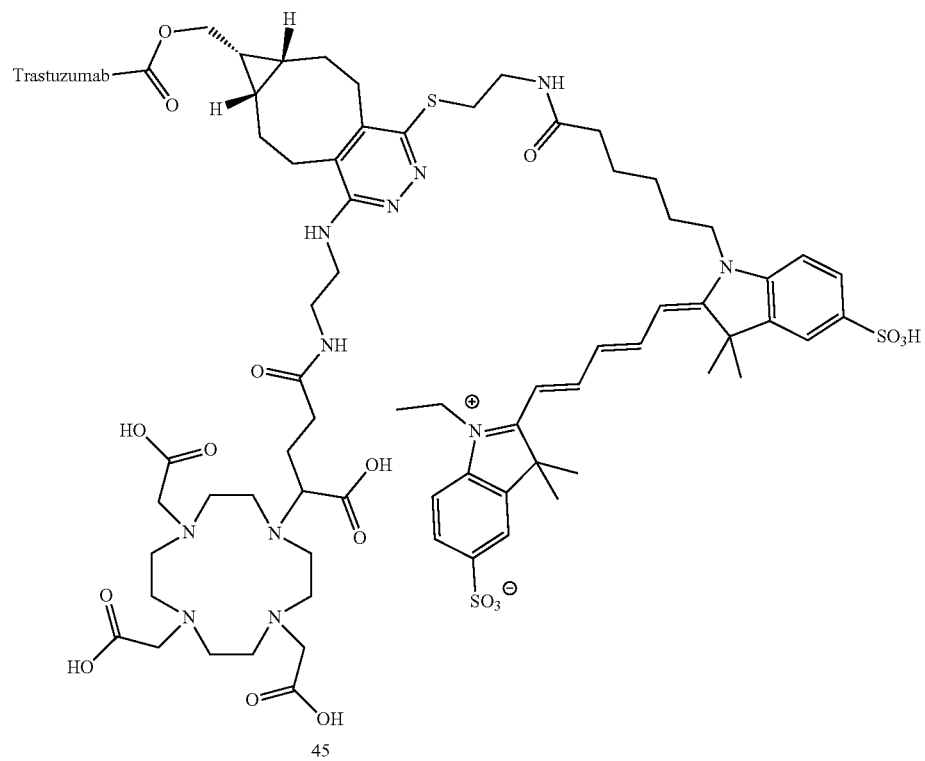

75.3 μL stock solution of DOTAGA-NH-Tz-disulfonated S-cyanine 5.0 at 5 mM in ultrapure water (376.6 nmol, 33.0 eq.) was added to trastuzumab-BCN (1.71 mg, 11.4 nmol) in solution in PBS (pH 7.4)+10% (v/v) DMSO (finale trastuzumab-BCN concentration: 10 mg/mL). The solution was left under agitation in a thermomixer (800 rpm, 37° C.) for 16 h. Excess probe was removed by FPLC purification (Akta Pure Healthcare, GE) on a desalting column (Hitrap desalting, 5 mL, pre-packed with Sephadex G-25 Superfine) with AcONH$_4$ buffer (0.1 M, pH 5.8, Trace Select) as eluent. Trastuzumab-BCN-pyridazine, NH-DOTAGA, disulfonated S-Cyanine 5.0 (I-1) was obtained in solution in 484 μL of ammonium acetate buffer at a concentration of 2.1 mg/mL (correction factor=0.095) (1.02 mg, 6.8 nmol, 59%). The probe/antibody ratio was 1.7 (determined by spectrophotometry). Analysis by gel electrophoresis under denaturing conditions showed a fluorescent signal for the molecular weight corresponding to compound I-1, indicating a bond of covalent type between the probe and trastuzumab antibody. The stability of compound I-1 was verified by incubation at 37° C., in the dark, in human plasma (analysis by gel electrophoresis of a sample after an incubation time of 1, 2, 4, 8, 24 and 48 h).

7.2. NODAGA-BCN-Pyridazine, S—(R)-NODAGA, S-Peptide (I-2)

2,2'-(7-((1S)-4-((2-(((((1-(((2S,5S,11S,17S,20S,23S, 26R)-17-((1H-indol-3-yl)methyl)-26-acetamido-1-amino-23-(4-aminobutyl)-5-(carboxymethyl)-11-(3-guanidinopropyl)-20-(4-hydroxybenzyl)-2-(hydroxymethyl)-1,4,7,10,13,16,19,22,25-nonaoxo-3,6,9,12,15,18,21,24-octaazaheptacosan-27-yl)thio)-4-((2-((S)-4-(4,7-bis(carboxymethyl)-1,4,7-triazonan-1-yl)-4-carboxybutanamido)ethyl)thio)-6,6a,7,7a,8,9-hexahydro-5H-cyclopropa[5,6]cycloocta[1,2-d]pyridazin-7-yl)methoxy)carbonyl)aminoethyl)amino)-1-carboxy-4-oxobutyl)-1,4,7-triazonane-1,4-diyl)diacetic acid

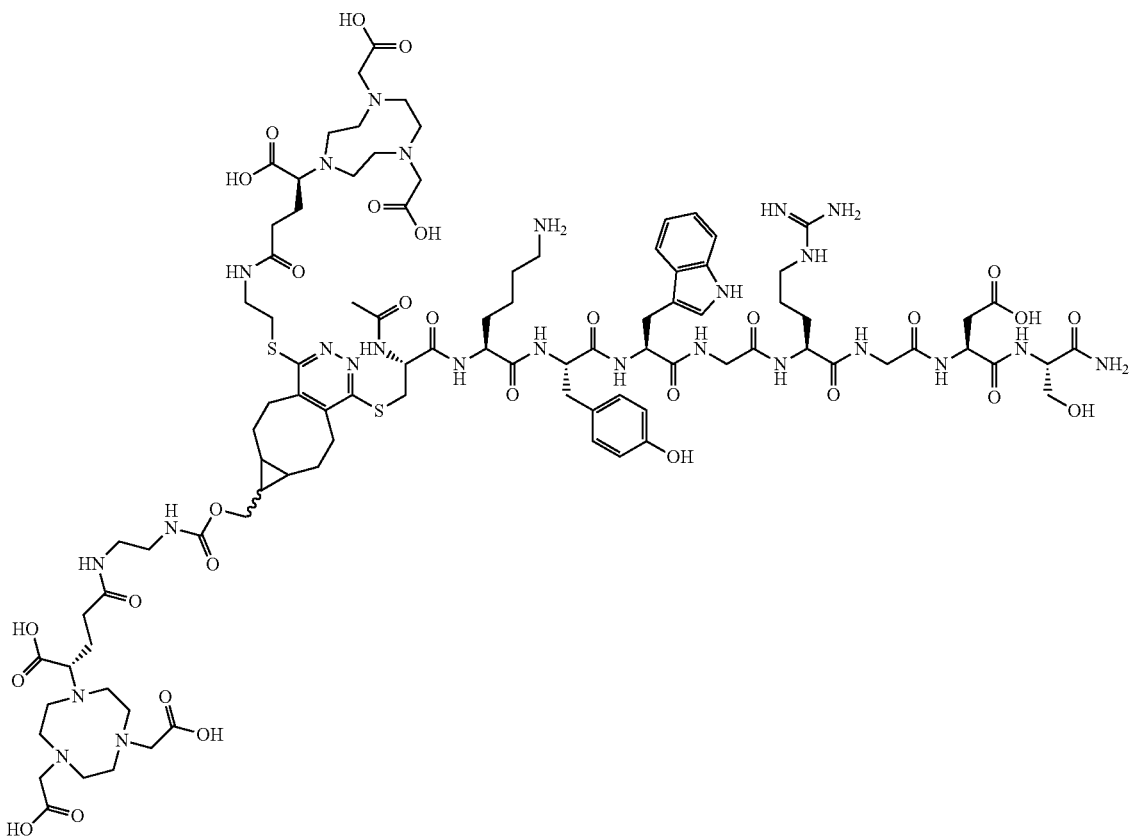

2 μL stock solution of (R)-NODAGA-S-Tz-S-peptide at 30 mM in DMSO (60 nmol) and 12 μL stock solution of NODAGA-BCN at 50 mM in PBS (600 mmol, 10 eq.) were combined in PBS at ambient temperature (finale (R)-NODAGA-S-Tz-S-peptide concentration: 2 mM and in DMSO: 6.7%). The progress of the reaction was monitored by UV-Vis spectrophotometry. After a reaction time of 50 min, the conversion rate to NODAGA-BCN-pyridazine, S—(R)-NODAGA, S-peptide (I-2) was 98% (determined by LC-MS at 214 nm). MS: $C_{95}H_{140}N_{26}O_{30}S_2$ ([M+2H]$^{2+}$) m/z calculated: 1095.5; found: 1096.0.

7.3. Disulfonated Cyanine 5.0-BCN-Pyridazine, S—(R)-NODAGA, S-BSA (I-3)

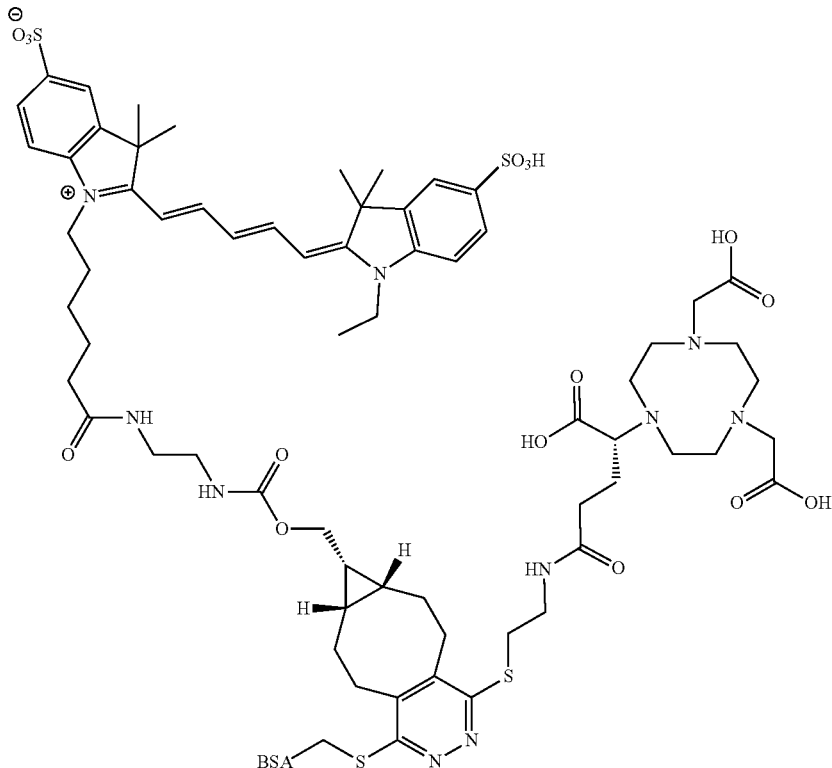

The compound (R)-NODAGA-S-tetrazine-S-BSA was combined with disulfonated cyanine 5.0-BCN by click chemical reaction, in an aqueous solution (phosphate buffer, pH=7.13) at 37° C. overnight. The end product disulfonated cyanine 5.0-BCN-pyridazine, S—(R)-NODAGA, S-BSA (I-3) was purified by steric exclusion chromatography. The probe/protein ratio was 0.7 (determined by spectrophotometry). LC-HRMS after deconvolution of the mass spectrum: 67851 (corresponds to compound I-3) and 66430 (corresponds to the protein residue without probe). Analysis by gel electrophoresis under denaturing conditions showed a fluorescent signal for the molecular weight corresponding to compound I-3, indicating a bond of covalent type between the probe and albumin. The stability of compound I-3 was verified by incubation at 37° C., in the dark, in human plasma (gel electrophoresis analysis of a sample after an incubation time of 1, 2, 4, 8, 24 and 48 h).

7.3. (Disulfonated Cyanine 5.0-BCN-pyridazine, S—(R)-NODAGA)$_2$, S-Fab' (I-4)

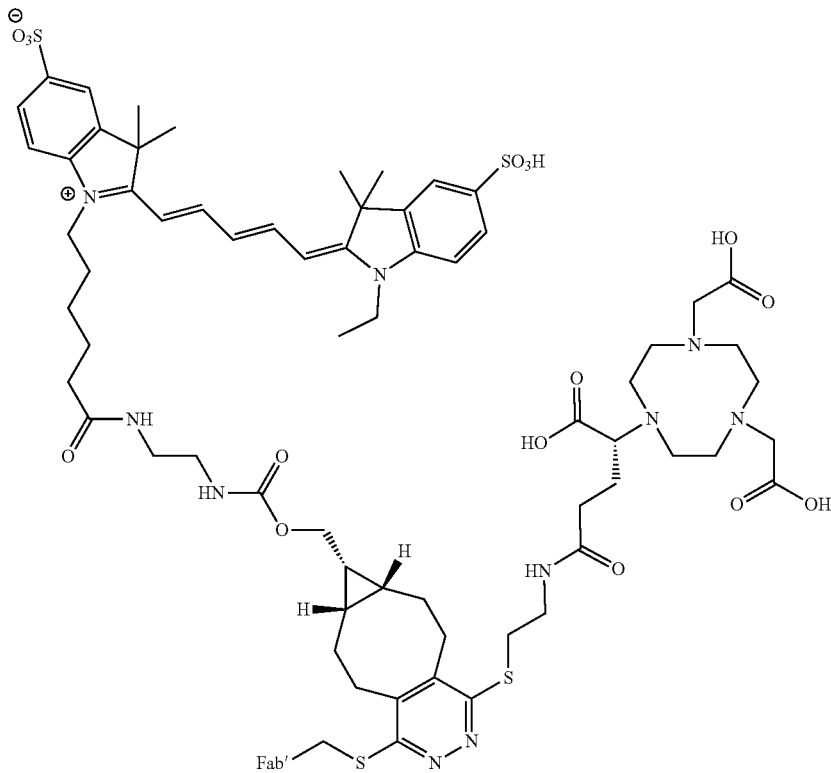

Disulfonated cyanine 5.0-BCN was added and the reaction mixture incubated at 37° C. overnight (pH=7.3) to obtain the product (disulfonated cyanine 5.0-BCN-pyridazine, S—(R)-NODAGA)$_2$, S-Fab' (I-4). The non-purified reaction was analysed by LC-HRMS, after deconvolution of the mass spectrum. The masses obtained were: 51503 (corresponds to compound I-4+2 copper cations) and 48659 (corresponds to the protein residue without probe).

Part II. Imaging Results

Compound I-1, after radiolabelling with indium 111, was studied for multimodal imaging via single photon emission computed tomography (SPECT) and for optical imaging (fluorescence). Compound I-3 was studied by optical imaging. In vivo experiments were conducted on a mouse model bearing a breast tumour xenograft (model BT-474).

8.1. Imaging Using Compound I-1 Radiolabelled with Indium 111

The objective of this experiment was to evidence the specific nature of compound I-1 radiolabelled with indium 111, used as imaging agent.

For this purpose, two batches of mice were studied:
batch A: mice treated with compound I-1 radiolabelled with indium 111 (n=4); and
batch B: mice treated with compound I-1 radiolabelled with indium 111 and non-labelled excess trastuzumab (n=3).

24 h after injection, images of the mice of batches A and B were recorded by single photon emission computed tomography (SPECT) and by optical imaging. Injection of a large excess of non-labelled trastuzumab (which saturates the HER2 receptors) allowed evidencing of the specificity of the imaging agent.

If no significant change is observed between the images of batches A and B, then accumulation of the imaging agent in the examined tissue is not specific. On the contrary, if the signal observed with batch A decreases or disappears from the image obtained with batch B, then the accumulation of the imaging agent in the examined tissue is specific.

Figure 2A:
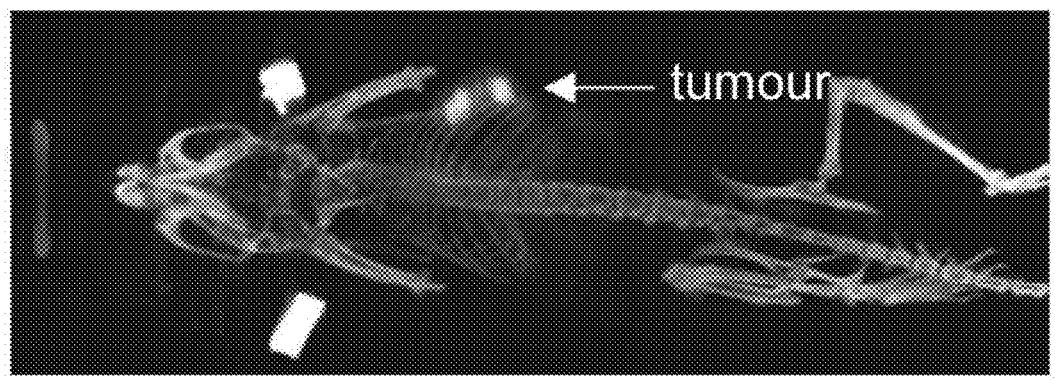
FIG. 2 gives the multimodal SPECT image of a mouse xenografted with BT-474 cells (breast tumour) treated with compound I-1 radiolabelled with indium 111 (FIG. 2A), and with compound I-1 radiolabelled with indium co-injected with non-labelled excess trastuzumab (FIG. 2B).
Figure 2B:
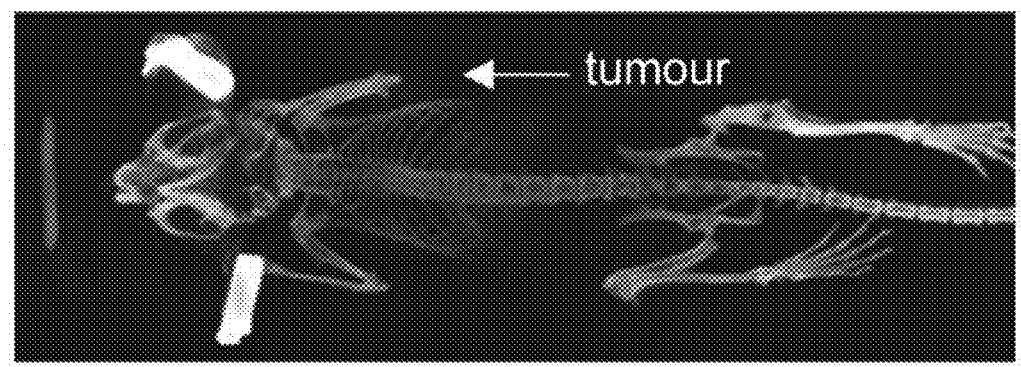

Single Photo Emission Computed Tomography (SPECT)
Examples of illustrative SPECT images are given for batch A, FIG. 2A and for batch B, FIG. 2B.

These results show that:
regarding treatment with compound I-1 radiolabelled with indium 111 (batch A), the tumour can be seen under SPECT imaging (cf. white mark in FIG. 2A);
when a mouse is treated with compound I-1 radiolabelled with indium 111 with large excess of non-labelled trastuzumab, the signal is seen to disappear compared with batch A.

This experiment therefore evidences the specific accumulation of the imaging agent in tumour tissue.

Figure 3:
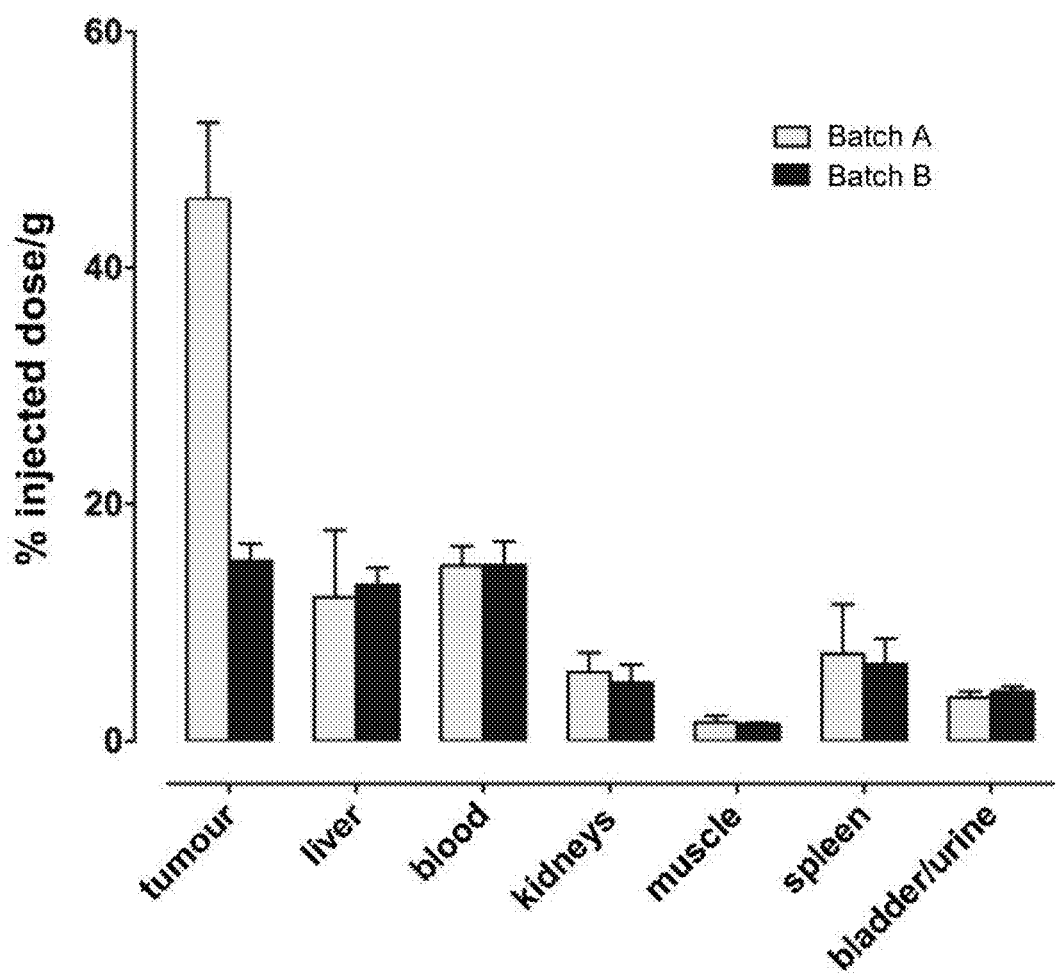
FIG. 3 gives a histogram showing the mean dose percentage injected per gram of organ, determined by gamma count in different organs of mice treated with compound I-1 radiolabelled with indium (batch A—light grey) or of mice treated with compound I-1 radiolabelled with indium with excess trastuzumab (batch B—dark grey).

FIG. 3 shows the biodistribution of radioactivity (mean dose percentage injected per gram of organ), in different organs of mice (n=4) treated with compound I-1 radiolabelled with indium 111 (batch A—light grey), or of mice (n=3) treated with compound I-1 radiolabelled with indium 111 with excess trastuzumab (batch B—dark grey).

In FIG. 3, a distinct difference is observed between batches A and B regarding the tumour compared with the other organs.

These results show the specificity of compound I-1 radiolabelled with indium 111 used as imaging agent, for the tumour in the studied model.

Optical Imaging (Fluorescence)

Figure 4:
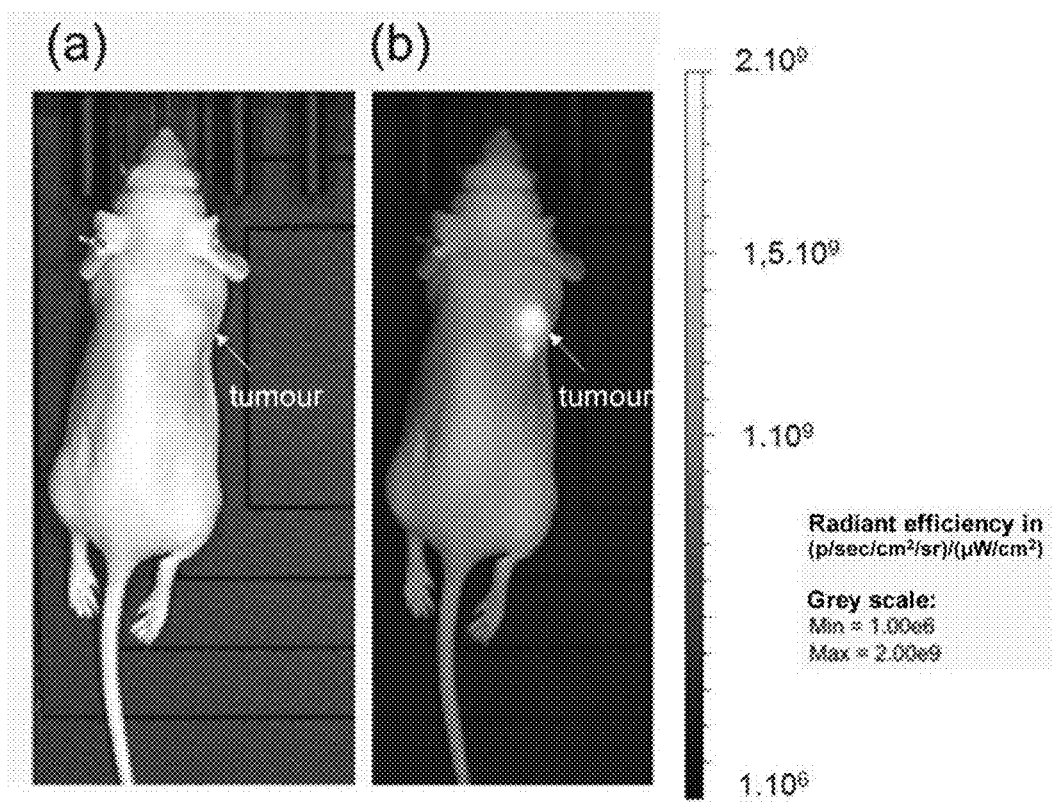
FIG. 4 is a photograph with (b) and without (a) fluorescence, of a mouse treated with compound I-1 radiolabelled with indium 111.

In vivo and ex vivo optical images were obtained for mice treated with compound I-1 radiolabelled with indium 111. FIG. 4 gives an in vivo photograph of a mouse treated with compound I-1 radiolabelled with indium 111 (FIG. 4(a)) in which the siting of the tumour is distinctly visible (top left protuberance from the animal's back).

The same image taken by superimposing the fluorescence signal (FIG. 4(b)) shows an intense signal (white) coinciding with the siting of the tumour.

These in vivo results confirm the efficacy of compound I-1 radiolabelled with indium 111 as imaging agent, in particular for the targeting of tumours.

Figure 5:
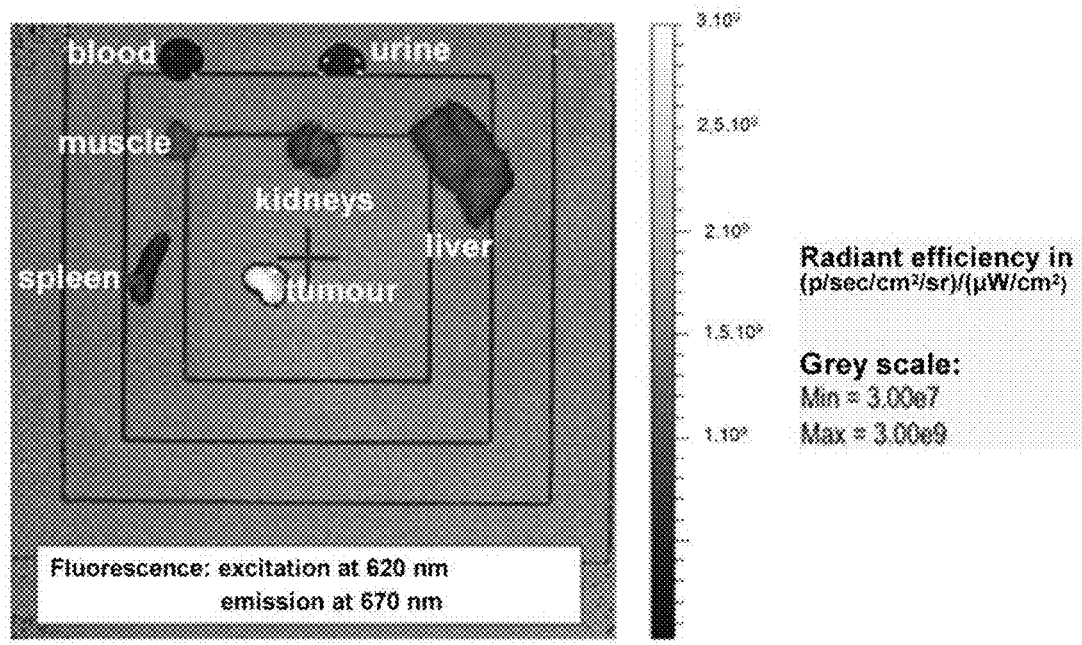
FIG. 5 is a photograph with ex vivo fluorescence of the tumour and of various organs of a mouse treated with compound I-1 radiolabelled with indium 111.
Figure 6:
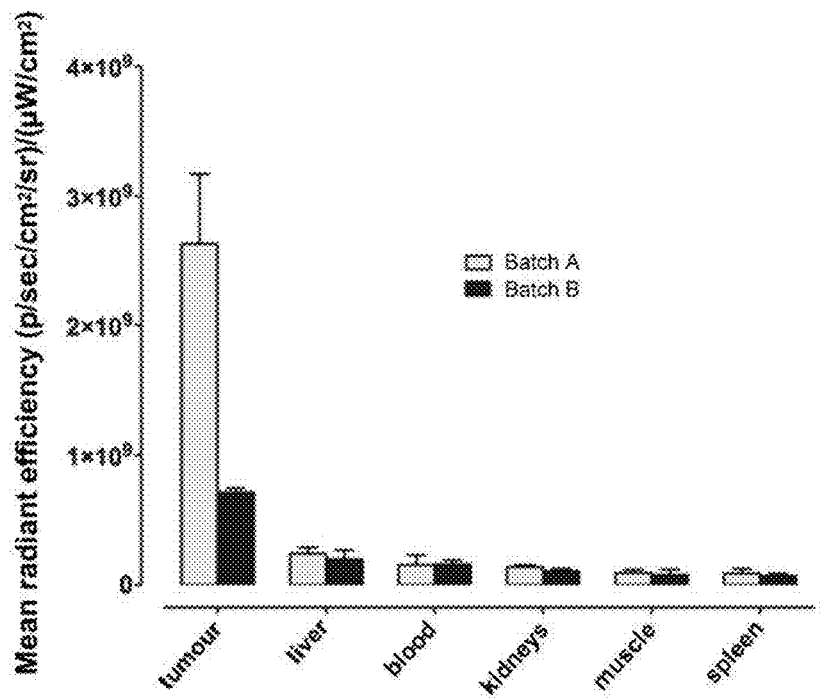
FIG. 6 gives a histogram showing the mean biodistribution of compound I-1 radiolabelled with indium 111 in the tumour and in various organs, for the mice in batch A (light grey) or mice in batch B (dark grey).

FIGS. 5 and 6 give the results obtained on isolated organs (ex vivo). In FIG. 5, the intensity of fluorescence emanating from the tumour is much more intense than the intensity from the other isolated organs. FIG. 6 confirms that compound I-1 radiolabelled with indium 111 acts as specific imaging agent with respect to the tumour. A marked difference in biodistribution is observed between batches A and B for the tumour compared with the other organs for which the signals are comparable.

To conclude, the results of fluorescence confirm the results obtained with nuclear imaging. The advantage of site-specific double labelling with trastuzumab is therefore demonstrated for applications in multimodal SPECT/optical imaging.

8.2. Imaging Using Compound I-3

A study was conducted using compound I-3 for optical imaging of a batch of mice previously xenografted with breast tumour BT-474 cells, and treated with compound I-3 (n=3, lot C).

Figure 7:
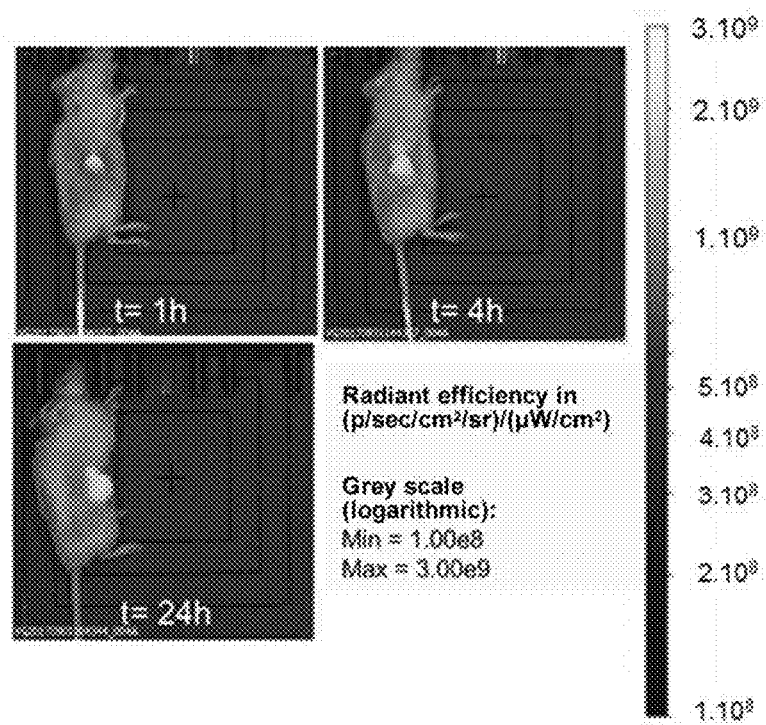
FIG. 7 is a photograph with in vivo fluorescence of a mouse treated with compound I-3 after 1 h, 4 h or 24 h post-injection.
Figure 8:
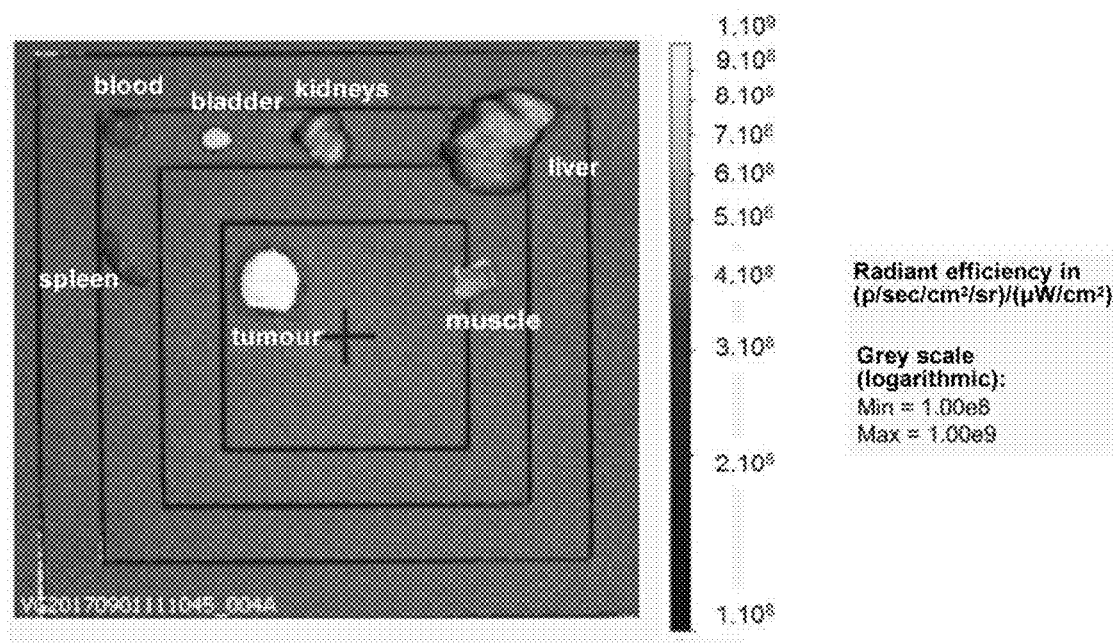
FIG. 8 is a photograph with ex vivo fluorescence of the tumour and of various organs of a mouse treated with compound I-3 after 24 h post-injection.
Figure 9:
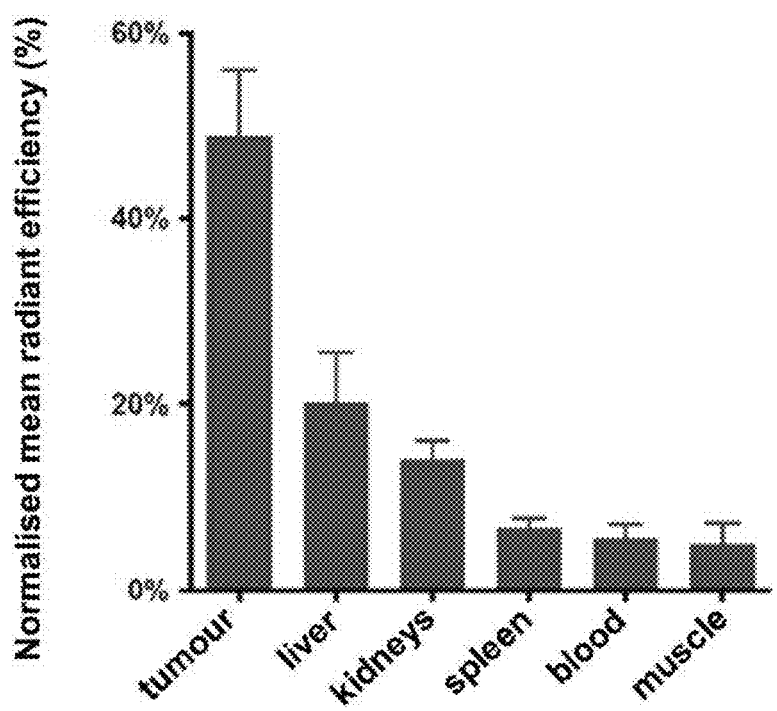
FIG. 9 gives a histogram showing the mean biodistribution of compound 1-3 in the tumour and in various organs, for the mice in batch C.

After treatment (t$_0$), in vivo fluorescence images of the mice in batch C were acquired at t=1 h, 4 h, and 24 h (FIG. 7); and ex vivo on isolated organs after 24 h (FIGS. 8 and 9).

FIG. 7 shows the change in the in vivo fluorescence signal in one mouse of the group in batch C. It shows that after injection of compound I-3, the fluorescence signals are intense (bright areas) in the tumour region even after 24 h, compared with the remainder of the organism.

FIG. 8 illustrates the results obtained on isolated organs and on the tumour (ex vivo) for one mouse in batch C. A more intense fluorescence signal in the tumour is observed compared with the other organs.

Quantification relating to FIG. 8 is given in FIG. 9.

To conclude, as for compound I-1, the experiments show that compound I-3 is an efficient imaging agent.

What is claimed is:

1. A compound of formula (I)

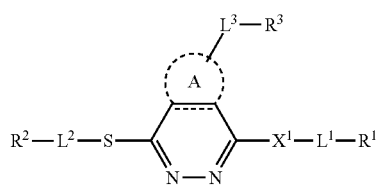

(I)

or one of the tautomers thereof, wherein:
------- is a double bond or single bond;
ring A is selected from the group consisting of bicyclo[6.1.0]nonane, cyclooctane, bicyclo[6.1.0]nonene, cyclooctene, difluorocyclooctene, hydroxycyclooctene, methylcyclopropane, norbornene, 5,6-dihydrodibenzo[a,e][8]annulene, and 5,6-dihydrodibenzo[b,f]azocine group;

$X^1$ is S, NH, or O;

$L^1$, $L^2$ and $L^3$ are each independently a single bond or spacer selected from the group consisting of alkyl, alkoxy, aryl, arylalkyl, alkylaryl, heteroaryl, heteroarylalkyl, alkylheteroaryl, alkenyl and alkynyl groups, wherein the alkyl groups optionally contain in the alkyl chain one or more groups selected from the group consisting of —O—, —NH—, —S—, —C(O)—, —C(O)NH— and —NHC(O)—, wherein the heteroaryl is an aromatic ring having 5 to 15 carbon atoms or cyclic systems containing 1 to 3 rings that are fused together or covalently bound; wherein one or more carbon atoms in one or more of these rings are replaced by oxygen, nitrogen and/or sulfur atoms; the nitrogen and sulfur atoms optionally being oxidized and the nitrogen atoms optionally being quaternized;

$R^1$, $R^2$ and $R^3$ are each independently a detectable group, a bioactive group, a cytotoxic agent, an affinity group, or a solubilising group;

said detectable group being selected from the group consisting of a fluorophore, chromophore, probe for nuclear imaging, and MRI probe, wherein the fluorophore is selected from among cyanine derivatives; Alexa fluor 647; a coumarin selected from hydroxycoumarin, aminocoumarin, and methoxy coumarin; a rhodamine selected from X-rhodamine, and rhodamine B; a fluorescein or BODIPY, and wherein the chromophore is selected from among phenolphthalein, gentian violet or Congo Red;

said bioactive group being selected from the group consisting of an antibody, peptide, peptidomimetic, protein, folic acid, an aptamer, a nanoparticle or liposome;

said affinity group being selected from the group consisting of biotin, avidin, streptavidin and hexa-histidine peptide;

said solubilising group being selected from the group consisting of linear or branched poly(ethylene glycol) chains, linear or branched poly(glutamic acid) chains and cholesterol;

provided that at least one of $R^1$ and $R^2$ is a detectable group, and at least one of $R^2$ and $R^3$ is a bioactive group.

2. The compound of formula (I) according to claim 1, wherein:
the cytotoxic agent is selected from the group consisting of monomethyl auristatin E, maytansinoid DM1, Duocarmycin, Calicheamicin, alpha-amanitin, a group carrying a radiometal, a silica nanoparticle and a gold nanoparticle.

3. A pharmaceutical composition comprising a compound of formula (I) according to claim 1 and a pharmaceutically acceptable vehicle.

4. A method for synthesising a compound of formula (I) according to claim 1, comprising the contacting of a bifunctionalized tetrazine of formula (II)

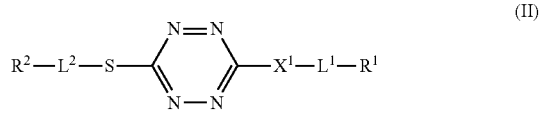

(II)

wherein:

$X^1$ is S, NH or O;

$L^1$ and $L^2$ are each independently a single bond or spacer selected from the group consisting of alkyl, alkoxy, aryl, arylalkyl, alkylaryl, heteroaryl, heteroarylalkyl, alkylheteroaryl, alkenyl and alkynyl groups, wherein the alkyl groups optionally contain in the alkyl chain one or more groups selected from the group consisting of —O—, —NH—, —S—, —C(O)—, —C(O)NH— and —NHC(O)—, wherein the heteroaryl is an aromatic ring having 5 to 15 carbon atoms or cyclic systems containing 1 to 3 rings that are fused together or covalently bound; wherein one or more carbon atoms in one or more of these rings are replaced by oxygen, nitrogen and/or sulfur atoms; the nitrogen and sulfur atoms optionally being oxidized and the nitrogen atoms optionally being quaternized;

$R^1$ and $R^2$ are each independently a detectable group, a bioactive group, a cytotoxic agent, an affinity group or a solubilising group;

provided that at least one of $R^1$ and $R^2$ is a detectable group;

with an alkyne or alkene of formula (III):

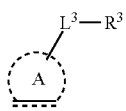

(III)

wherein:

═══════ represents a triple bond or double bond $L^3$ is a single bond or spacer selected from the group consisting of alkyl, alkoxy, aryl, arylalkyl, alkylaryl, heteroaryl, heteroarylalkyl, alkylheteroaryl, alkenyl and alkynyl groups, wherein the alkyl groups optionally contain in the alkyl chain one or more groups selected from the group consisting of —O—, —NH—, —S—, —C(O)—, —C(O)NH— and —NHC(O)—, wherein the heteroaryl is an aromatic ring having 5 to 15 carbon atoms or cyclic systems containing 1 to 3 rings that are fused together or covalently bound; wherein one or more carbon atoms in one or more of these rings are replaced by oxygen, nitrogen and/or sulfur atoms; the nitrogen and sulfur atoms optionally being oxidized and the nitrogen atoms optionally being quaternized;

provided that at least one of $R^2$ and $R^3$ is a bioactive group.

5. The method according to claim 4 further comprising a forming the bifunctionalized tetrazine of formula (II) by nucleophilic substitution on a tetrazine of formula (IV):

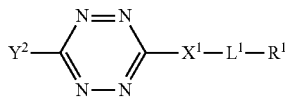

(IV)

wherein:

$Y^2$ is a halogen or leaving group selected from the group consisting of mesylate, tosylate, triflate and 3,5-dimethyl-1H-pyrazol-1yl groups;

$X^1$ is S, NH or O;

$L^1$ is a single bond or spacer selected from the group consisting of alkyl, alkoxy, aryl, arylalkyl, alkylaryl, heteroaryl, heteroarylalkyl, alkylheteroaryl, alkenyl and alkynyl groups, wherein the alkyl groups optionally contain in the alkyl chain one or more groups selected from the group consisting of —O—, —NH—, —S—, —C(O)—, —C(O)NH— and —NHC(O)—, wherein the heteroaryl is an aromatic ring having 5 to 15 carbon atoms or cyclic systems containing 1 to 3 rings that are fused together or covalently bound; wherein one or more carbon atoms in one or more of these rings are replaced by oxygen, nitrogen and/or sulfur atoms; the nitrogen and sulfur atoms optionally being oxidized and the nitrogen atoms optionally being quaternized;

in the presence of a thiol of formula (V)

$R^2$-$L^2$-SH (V)

wherein:

$L^2$ is a single bond or spacer selected from the group consisting of alkyl, alkoxy, aryl, arylalkyl, alkylaryl, heteroaryl, heteroarylalkyl, alkylheteroaryl, alkenyl and alkynyl groups, wherein the alkyl groups optionally contain in the alkyl chain one or more groups selected from the group consisting of —O—, —NH—, —S—, —C(O)—, —C(O)NH— and —NHC(O)—, wherein the heteroaryl is an aromatic ring having 5 to 15 carbon atoms or cyclic systems containing 1 to 3 rings that are fused together or covalently bound; wherein one or more carbon atoms in one or more of these rings are replaced by oxygen, nitrogen and/or sulfur atoms; the nitrogen and sulfur atoms optionally being oxidized and the nitrogen atoms optionally being quaternized provided that at least one of $R^1$ and $R^2$ is a detectable group.

6. The method according to claim 5, further comprising a step to form the tetrazine of formula (IV) by nucleophilic monosubstitution of a tetrazine of formula (VI):

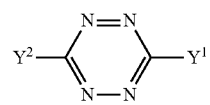

(VI)

where $Y^1$ and $Y^2$ are each independently a halogen or leaving group selected from the group consisting of mesylate, tosylate, triflate and 3,5-dimethyl-1H-pyrazol-1yl groups;

in the presence of a nucleophile of formula (VII)

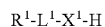

$R^1$-$L^1$-$X^1$-H (VII)

where:

$X^1$ is S, NH, or O; and $L^1$ is a single bond or spacer selected from the group consisting of alkyl, alkoxy, aryl, arylalkyl, alkylaryl, heteroaryl, heteroarylalkyl, alkylheteroaryl, alkenyl and alkynyl groups, wherein the alkyl groups optionally contain in the alkyl chain one or more groups selected from the group consisting of —O—, —NH—, —S—, —C(O)—, —C(O)NH— and —NHC(O)—, wherein the heteroaryl is an aromatic ring having 5 to 15 carbon atoms or cyclic systems containing 1 to 3 rings that are fused together or covalently bound; wherein one or more carbon atoms in one or more of these rings are replaced by oxygen, nitrogen and/or sulfur atoms; the nitrogen and sulfur atoms optionally being oxidized and the nitrogen atoms optionally being quaternized.

7. The compound of claim 1, wherein the detectable group is a fluorophore being a cyanine derivative selected from the group consisting of: Cyanine3, Cyanine5, Cyanine5.5, Cyanine7, and Sulfonated Cyanines.

8. The compound of claim 1, wherein $L^1$, $L^2$ and $L^3$ are each independently selected from the group consisting of —CH$_2$CH$_2$NH—, —NHCH$_2$CH$_2$NH—, —CH$_2$OCONH—CH$_2$CH$_2$NHCOCH$_2$CH$_2$—, —CH$_2$OCO—, —COCH$_2$CH$_2$NH—, —CH$_2$CH$_2$NHCO—CH$_2$CH$_2$— and —CH$_2$CH$_2$NHCO-p-Ph-.

9. The method according to claim 5, wherein $Y^2$ is chlorine.

10. The method according to claim 5, wherein $L^1$ and $L^2$ are each independently selected from the group consisting of —CH$_2$CH$_2$NH—, —NHCH$_2$CH$_2$NH—, —CH$_2$OCONH—CH$_2$CH$_2$NHCOCH$_2$CH$_2$—, —CH$_2$OCO—, —COCH$_2$CH$_2$NH—, —CH$_2$CH$_2$NHCO—CH$_2$CH$_2$— and —CH$_2$CH$_2$NHCO-p-Ph-.

11. The method according to claim 6, wherein $Y^1$ and $Y^2$ are chlorine.

12. The method according to claim 6, wherein $L^1$ is selected from the group consisting of —CH$_2$CH$_2$NH—, —NHCH$_2$CH$_2$NH—, —CH$_2$OCONH—CH$_2$CH$_2$NHCOCH$_2$CH$_2$—, —CH$_2$OCO—, —COCH$_2$CH$_2$NH—, —CH$_2$CH$_2$NHCO—CH$_2$CH$_2$— and —CH$_2$CH$_2$NHCO-p-Ph-.

13. The compound of claim 1, having the following formula (I-a):

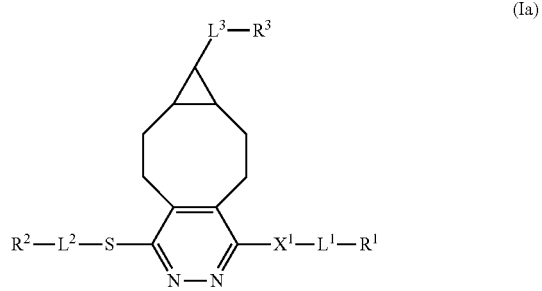

(Ia)

or one of the tautomers thereof.

* * * * *